US012742153B2

(12) United States Patent
Bollard et al.

(10) Patent No.: US 12,742,153 B2
(45) Date of Patent: Sep. 22, 2026

(54) FIXED RATIO EX VIVO ACTIVATED MIXED LYMPHOCYTE PRODUCTS FOR USE IN THE TREATMENT OF CANCER

(71) Applicant: Children's National Medical Center, Washington, DC (US)

(72) Inventors: Catherine Bollard, Bathesda, MD (US); Conrad Russell Cruz, Bathesda, MD (US); Patrick Hanley, Washington, DC (US)

(73) Assignee: Children's National Medical Center, Washington, DC (US)

( * ) Notice: Subject to any disclaimer, the term of this patent is extended or adjusted under 35 U.S.C. 154(b) by 1471 days.

(21) Appl. No.: 17/049,307

(22) PCT Filed: Apr. 22, 2019

(86) PCT No.: PCT/US2019/028589
§ 371 (c)(1),
(2) Date: Oct. 20, 2020

(87) PCT Pub. No.: WO2019/204831
PCT Pub. Date: Oct. 24, 2019

(65) Prior Publication Data

US 2021/0046119 A1 Feb. 18, 2021

Related U.S. Application Data

(60) Provisional application No. 62/660,878, filed on Apr. 20, 2018.

(51) Int. Cl.

| | |
|---|---|
| ***A61K 40/11*** | (2025.01) |
| ***A61K 40/42*** | (2025.01) |
| ***A61P 35/00*** | (2006.01) |
| ***A61P 37/04*** | (2006.01) |
| ***C12N 5/0783*** | (2010.01) |
| ***C12N 5/0784*** | (2010.01) |

(52) U.S. Cl.

CPC ............ *C12N 5/0638* (2013.01); *A61K 40/11* (2025.01); *A61K 40/424* (2025.01); *A61K 40/4243* (2025.01); *A61K 40/4268* (2025.01); *A61K 40/427* (2025.01); *A61K 40/428* (2025.01); *A61P 35/00* (2018.01); *A61P 37/04* (2018.01); *C12N 5/0636* (2013.01); *C12N 5/0637* (2013.01); *C12N 5/0639* (2013.01); *C12N 5/0646* (2013.01); *A61K 2239/31* (2023.05); *A61K 2239/38* (2023.05); *C12N 2501/22* (2013.01); *C12N 2501/2302* (2013.01); *C12N 2501/2304* (2013.01); *C12N 2501/40* (2013.01); *C12N 2501/48* (2013.01); *C12N 2501/60* (2013.01)

(58) Field of Classification Search

CPC ............ A61K 35/17; A61K 39/464453; A61K 39/464489; A61K 39/46445; A61K 39/464486; A61K 2239/38; A61P 35/00; A61P 37/04; C12N 5/0637; C12N 5/0638; C12N 5/0646

See application file for complete search history.

(56) References Cited

U.S. PATENT DOCUMENTS

| | | | |
|---|---|---|---|
| 4,690,915 | A | 9/1987 | Rosenberg |
| 2003/0170238 | A1 | 9/2003 | Gruenberg et al. |
| 2009/0098095 | A1 | 4/2009 | Zhang et al. |
| 2016/0045550 | A1 | 2/2016 | Zhang et al. |
| 2017/0037369 | A1 | 2/2017 | Ramsborg et al. |

FOREIGN PATENT DOCUMENTS

| | | | | |
|---|---|---|---|---|
| WO | WO-2016/087871 A1 | 6/2016 | | |
| WO | WO-2016/154112 A1 | 9/2016 | | |
| WO | WO-2017117418 A1 * | 7/2017 | ............. | A61K 35/17 |
| WO | 2020/146434 A2 | 7/2020 | | |

OTHER PUBLICATIONS

Peng et al. Altered phenotypic and functional characteristics of CD3+CD56+ NKT-like cells in human gastric cancer. Oncotarget. Aug. 23, 2016;7(34):55222-55230. doi: 10.18632/oncotarget.10484. PMID: 27409423; PMCID: PMC5342413 (Year: 2016).*

Alonso-Camino V et al. The profile of tumor antigens which can be targeted by immunotherapy depends upon the tumor's anatomical site. Mol Ther. Nov. 2014;22(11):1936-48. doi: 10.1038/mt.2014.134. Epub Jul. 25, 2014. PMID: 25059678; PMCID: PMC4429729 (Year: 2014).*

Vonderheide RH. The Immune Revolution: A Case for Priming, Not Checkpoint. Cancer Cell. Apr. 9, 2018;33(4):563-569. doi: 10.1016/j.ccell.2018.03.008. PMID: 29634944; PMCID: PMC5898647 (Year: 2018).*

Yewdall AW. et al. CD8+ T cell priming by dendritic cell vaccines requires antigen transfer to endogenous antigen presenting cells. PLoS One. Jun. 16, 2010;5(6):e11144. doi: 10.1371/journal.pone.0011144. PMID: 20585396; PMCID: PMC2886840 (Year: 2010).*

(Continued)

*Primary Examiner* — Maria G Leavitt
*Assistant Examiner* — Vyoma Shubham Tiwari
(74) *Attorney, Agent, or Firm* — McCarter & English, LLP; Yu Lu

(57) ABSTRACT

The present invention provides isolated cell compositions for the treatment of cancer, including hematological and solid tumors, comprising a selected, fixed ratio of multiple ex vivo activated lymphocytic cell subsets, including specific immune effector cells directed to specific tumor associated antigens (TAAs), viral associated tumor antigens (VATA), glycolipids, or a combination thereof. By selecting specific fixed ratios of different lymphocytic cell subsets, an immune response which is comprehensive and broad pin biological and immune effector function is provided, enhancing the ability of the administered cells to mount an effective and robust immune response.

5 Claims, 10 Drawing Sheets

Specification includes a Sequence Listing.

(56) References Cited

OTHER PUBLICATIONS

Yu, S., et al., Chimeric antigen receptor T cells: A novel therapy for solid tumors, J. Hematol. Oncol., 2017, 10(1):78.
Kalos, M., et al., T cells with chimeric antigen receptors have potent antitumor effects and can establish memory in patients with advanced leukemia, Sci. Transl. Med., 2011, 3(95):95ra73.
Weber, G., et al., Generation of tumor antigen-specific T cell lines from pediatric patients with acute lymphoblastic leukemia—implications for immunotherapy, Clin. Cancer Res., 2013, 19(18):5079-5091.
Verma, R., et al., Lymphocyte depletion and repopulation after chemotherapy for primary breast cancer, Breast Cancer Res., 2016, 18(1): 10.
Turtle, C. J., et al., CD19 CAR-T cells of defined $CD4^+$:$CD8^+$ composition in adult B cell ALL patients, J. Clin. Invest., 2016, 126(6):2123-2138.
Turtle, C. J., et al., Immunotherapy of non-Hodgkin's lymphoma with a defined ratio of $CD8^+$ and $CD4^+$ CD19-specific chimeric antigen receptor-modified T cells, Sci. Transl. Med., 2016, 8(355):355ra116.
Ngo, M. C., et al., Complementation of antigen-presenting cells to generate T lymphocytes with broad target specificity, J. Immunother., 2014, 37(4):193-203.
Henikoff, S., et al., Amino acid substitution matrices from protein blocks, Proc. Natl. Acad. Sci. USA, 1992, 89(22):10915-10919.
Karlin, S., et al., Applications and statistics for multiple high-scoring segments in molecular sequences, Proc. Natl. Acad. Sci. USA, 1993, 90(12):5873-5787.
Del Prete, G., Human Th1 and Th2 lymphocytes: their role in the pathophysiology of atopy, Allergy, 1992, 47(5):450-455.
Murray, H. W., et al., Human mononuclear phagocyte antiprotozoal mechanisms: Oxygen-dependent vs oxygen-independent activity against intracellular *Toxoplasma gondii*, J. Immunol., 1985, 134(3):1982-1988 (Abstract only).
Boehm, U., et al., Cellular responses to interferon-γ, Annu. Rev. Immunol., 1997, 15:749-795 (Abstract only).
Kim, H. P., et al., Both integrated and differential regulation of components of the IL-2/IL-2 receptor system, Cytokine Growth Factor Rev., 2006, 17(5):349-366 (Abstract only).
Gattinoni, L., et al., Acquisition of full effector function in vitro paradoxically impairs the in vivo antitumor efficacy of adoptively transferred $CD8^+$ T cells, J. Clin. Invest., 2005, 115(6):1616-1626.
Williams, M. A., et al., Interleukin-2 signals during priming are required for secondary expansion of CD8+ memory T cells, Nature, 2006, 441(7095):890-893.
Geissmann, F., et al., Blood monocytes consist of two principal subsets with distinct migratory properties, Immunity, 2003, 19(1):71-82.
Cheever, M. A., et al., The prioritization of cancer antigens: A national cancer institute pilot project for the acceleration of translational research, Clin. Cancer Res., 2009, 15(17):5323-5337.
Shafer, J. A., et al., Antigen-specific cytotoxic T lymphocytes can target chemoresistant side-population tumor cells in Hodgkin lymphoma, Leuk. Lymphoma, 2010, 51(5):870-880.
Cruz, C. R., et al., Improving T-cell therapy for relapsed EBV-negative Hodgkin lymphoma by targeting upregulated MAGE-A4, Clin. Cancer Res., 2011, 17(22):7058-7066.
Quintarelli, C., et al., High-avidity cytotoxic T lymphocytes specific for a new PRAME-derived peptide can target leukemic and leukemic-precursor cells, Blood, 2011, 117(12):3353-3362.
Chapuis, A. g., et al., Transferred WT1-reactive CD8+ T cells can mediate antileukemic activity and persist in post-transplant patients, Sci. Transl. Med., 2013, 5(174):174ra27.
East, J. E., et al., Artificial antigen presenting cell (aAPC) mediated activation and expansion of natural killer T cells, J. Vis. Exp., 2012, (70):e4333.
Webb, T. J., et al., Ex vivo induction and expansion of natural killer T cells by CD1d1-Ig coated artificial antigen presenting cells, J. Immunol. Methods, 2009, 346(1-2):38-44.
Osada, T., et al., Ex vivo expanded human $CD4^+$ regulatory NKT cells suppress expansion of tumor antigen-specific CTLs, Int. Immunol., 2005, 17(9):1143-1155.
Fernandez, C. S., et al., Ex-vivo a-galactosylceramide activation of NKT cells in humans and macaques, J. Immunol. Methods, 2012, 382(1-2):150-159 (Abstract only).
Kondo, M., et al., Zoledronate facilitates large-scale ex vivo expansion of functional gamma delta T cells from cancer patients for use in adoptive immunotherapy, Cytotherapy. 2008, 10(8):842-856 (Abstract only).
Nicol, A. J., et al., Clinical evaluation of autologous gamma delta T cell-based immunotherapy for metastatic solid tumors, Br. J. Cancer, 2011, 105(6):778-786.
Godfrey, H. P., et al., Separation by column chromatography of cells active in delayed-onset hypersensitivities, Immunology, 1976, 30(5):695-703.
Xiao, F., et al., Cell column chromatography: A new research tool to quantify cerebral cell volume changes following chemically-induced anoxia/re-oxygenation, Acta Neurochir. Suppl., 2005, 95:411-414 (Abstract only).
Sugita, N., et al., Optimization of human mesenchymal stem cell isolation from synovial membrane: Implications for subsequent tissue engineering effectiveness, Regenerative Therapy, 2016, 5:79-85.
Syverud, B. C., et al., Isolation and purification of satellite cells for skeletal muscle tissue engineering, J. Regen. Med., 2014, 3(2):117.
Lange, V., et al., Cost-efficient high-throughput HLA typing by MiSeq amplicon sequencing, BMC Genomics, 2014, 15:63.
Erlich, H., HLA DNA typing: past, present, and future, Tissue Antigens, 2012, 80(1):1-11.
Bontadini, A., HLA techniques: typing and antibody detection in the laboratory of immunogenetics, Methods, 2012, 56(4):471-476 (Abstract only).
Dunn, P. P. J, Human leucocyte antigen typing: techniques and technology, a critical appraisal, Int. J. Immunogenet., 2011, 38(6):463-473.
Rosenberg, S. A., Cell transfer immunotherapy for metastatic solid cancer—what clinicians need to know, Nat. Rev. Clin. Oncol., 2011, 8(10):577-585.
Themeli, M., et al., Generation of tumor-targeted human T lymphocytes from induced pluripotent stem cells for cancer therapy, Nat. Biotechnol., 2013, 31(10):928-933.
Tsukahara, T., et al., CD19 target-engineered T-cells accumulate at tumor lesions in human B-cell lymphoma xenograft mouse models, Biochem. Biophys. Res. Commun., 2013, 438(1):84-89.
Davila, M. L., et al., CD19 CAR-targeted T cells induce long-term remission and B cell aplasia in an immunocompetent mouse model of B cell acute lymphoblastic leukemia, PLoS One, 2013, 8(4):e61338.
Kochenderfer, J. N., et al., Construction and preclinical evaluation of an anti-CD19 chimeric antigen receptor, J. Immunotherapy, 2009, 32(7):689-702.
Hermans, I. F., et al., The VITAL assay: A versatile fluorometric technique for assessing CTL- and NKT-mediated cytotoxicity against multiple targets in vitro and in vivo, J. Immunol. Methods, 2004, 285(1):25-40 (Abstract only).
Cruz, C. R., et al. Adverse events following infusion of T cells for adoptive immunotherapy: A 10-year experience, Cytotherapy, 2010, 12(6):743-749.
Eisenhauer, E. A., et al., New response evaluation criteria in solid tumors: Revised RECIST guideline (version 1.1), Eur. J. Cancer, 2009, 45(2):228-247.
Leen, A. M., et al., Monoculture-derived T-lymphocytes specific for multiple viruses expand and produce clinically relevant effects in immunocompromised individuals, Nature Medicine, 2006, 12(10):1160-1166 (Abstract only).
Salot, S., et al., Large scale expansion of Vγ9Vδ2 T lymphocytes from human peripheral blood mononuclear cells after a positive selection using MACS γ/δ T cell isolation kit, J. Immunol. Methods, 2009, 347(1-2):12-18 (Abstract only).
Kondo, M., et al., Expansion of human peripheral blood γδ T cells using zoledronate, J. Vis. Exp., 2011, (55):3182.

(56) References Cited

OTHER PUBLICATIONS

Deniger, D. C., et al., Activating and propagating polyclonal gamma delta T cells with broad specificity for malignancies, Clin. Cancer Res., 2014, 20(22):5708-5719.
Watarai, H., et al., Methods for detection, isolation and culture of mouse and human invariant NKT cells, Nature Protocols, 2008, 3(1):70-78 (Abstract only).
Lapteva, N., et al., Large-scale ex vivo expansion and characterization of natural killer cells for clinical applications, Cytotherapy, 2012, 14(9):1131-1143.
Merims, S., et al., Anti-leukemia effect of ex vivo expanded DNT cells from AML patients: a potential novel autologous T-cell adoptive immunotherapy, Leukemia, 2011, 25(9):1415-1422.
International Search Report and Written Opinion of the International Searching Authority for PCT/US2019/028589 Mailed Sep. 17, 2019.
International Preliminary Report on Patentability for PCT/US2019/028589 Issued Oct. 20, 2020.
Sutlu et al., Natural killer cell-based immunotherapy in cancer: current insights and future prospects. J Intern Med. Aug. 2009;266(2):154-81.

* cited by examiner

FIXED RATIO EX VIVO ACTIVATED MIXED LYMPHOCYTE PRODUCTS FOR USE IN THE TREATMENT OF CANCER

RELATED APPLICATIONS

This application is a National Stage application filed under 35 U.S.C. § 371 of International Application No. PCT/US2019/028589, filed on Apr. 22, 2019, which claims the benefit of provisional U.S. Application No. 62/660,878, filed Apr. 20, 2018. The content of each of the aforementioned applications is hereby incorporated by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 37921_0010U2_SL. The size of the text file is 10 KB and the text file was created on Oct. 19, 2020.

FIELD OF THE INVENTION

The present invention is in the field of adoptive lymphocytic therapies for the treatment of hematological and solid malignancies.

BACKGROUND OF THE INVENTION

Preliminary data from early-phase clinical trials utilizing engineered T-cell therapeutics are promising. Specifically, the development of CD19-directed chimeric antigen receptor (CAR) T cells has revolutionized the treatment of $CD19^+$ B-cell malignancies, including lymphomas, and has elicited some profound clinical regressions. CAR-T therapy, however, is not without its limitations.

One challenge of CAR-T therapies is that the engineered CAR-T cell targets a particular antigen on the surface of the cell; thus, tumors that down-regulate or mutate this protein will successfully evade the CAR-T cells, abrogating the anti-tumor effect. Second, few antigens have been used to generate the CAR-T cells, which restricts this therapy to target a limited number of tumors expressing currently available CAR (see Yu et al., Chimeric antigen receptor T cells: a novel therapy for solid tumors, J. Hem. Onc. (2017) 10:78). Therefore, many patients with non-targeted cancers, for example solid tumors, are unable to benefit from this therapy. Additionally, CAR-T cells have been associated with significant inflammatory toxicities, limiting patient eligibility and timing of administration. Finally, these cells have limited persistence in vivo and may not lead to durable lasting immunity, which is currently accepted as a requirement to prevent high-risk hematopoietic and solid tumor relapse (see Kalos et al. T cells with Chimeric Antigen Receptors have Potent Antitumor Effects and can Establish Memory in Patients with Advanced Leukemia. Science Translational Medicine. Aug. 10 2011; 3(95):95ra73).

In an attempt to circumvent the limitations associated with CAR-T therapies, several strategies have also been developed using non-cell-engineering methods to target cancers, including refractory and relapsed hematological and solid tumors. These non-gene modified approaches rely on the infusion of tumor-specific T cells which specifically target tumor cells expressing specific proteins or tumor associated antigens, and provide several potential advantages including that: 1) T cell responses are specific and can thus potentially distinguish between healthy and cancerous tissue; 2) T cell responses are robust, undergoing up to 1,000-fold clonal expansion after activation; 3) T cell responses may be able to traffic to the site of antigen, suggesting a mechanism for eradication of distant metastases; 4) T cell responses have memory, potentially allowing for the maintenance of therapeutic effect for many years after initial treatment, and 5) the therapies have shown to be relatively safe so far.

One strategy used to develop targeted non-engineered T-cells involves the ex vivo expansion of T-cells by antigen-specific stimulation of patient-derived (autologous) or donor-derived (allogeneic) T cells ex vivo. These strategies generally involve the isolation of peripheral blood mononuclear cells (PBMCs) and exposure of the cells to one or more tumor associated antigens.

For example, WO 2016/154112, assigned to Children's National Medical Center, describes the generation of cytotoxic T-lymphocytes (CTLs) reactive against multiple tumor antigens simultaneously by stimulation with dendritic cells pulsed with mixtures of overlapping peptides (PepMixes) spanning the antigens of interest as a stimulus in the presence of a cytokine cocktail.

While tremendous progress has been made using the ex vivo expansion of T-cells, the broader application and success of this approach for tumor therapy can be improved. Challenges encountered using this therapeutic approach include the fact that certain tumors do not induce strong responses from T cells because of inefficient antigen presentation and/or the presentation of tumor-associated antigens that are mostly self-proteins, which are not usually immunogenic. Furthermore, tumors use multiple immune evasion strategies to dampen or shut off the activity of the T cells that are capable of mounting a response to the tumor, and can modulate antigen presentation (by downregulation of tumor antigen, MHC, or costimulatory molecule expression) and the immune environment (by secreting immunosuppressive cytokines) to counteract the T cell response.

Accordingly, it is an object of the present invention to provide improved therapeutic modalities using non-engineered adoptive lymphocyte therapies capable of treating cancers, including hematological and solid tumors.

SUMMARY OF THE INVENTION

The present invention provides isolated cell compositions for the treatment of cancer, including hematological and solid tumors, comprising a standardized, non-naturally occurring fixed ratio of multiple ex vivo activated non-engineered lymphocytic cell subsets, including specific immune effector cells directed to specific tumor associated antigens (TAAs), viral associated tumor antigens (VATA), glycolipids, or a combination thereof. By selecting specific fixed ratios of different lymphocytic cell subsets, an immune response which is more comprehensive and broad in biological and immune effector function is provided, enhancing the ability of the administered cells to mount an effective and robust immune response.

Prior strategies employed in the ex vivo expansion of non-engineered T-cells by repeated antigen-specific stimulation can result in highly heterogeneous end products, which can vary from one sample or batch to another due to the great variability in starting materials. For example, Weber et al. describe the generation of lymphocytic cell lines wherein autologous peripheral blood mononuclear cells were stimulated ex vivo with autologous dendritic cells pulsed with complete peptide libraries of WT1, Survivin, MAGE-A3 and PRAME. Phenotyping of the ex vivo expanded lymphocytic cell lines showed a mean CD3$^+$ content of 97.2% (range 80.3-99.9%) and varying distribution of CD4$^+$ (mean 38.4% range 8.3-89.4%) and CD8$^+$ (mean 42.6% range 7.9-82.1%) T cells, few NK cells (mean 1.3% range 0-10.9%) and rare residual B cells (mean 0.2% range 0-5.8%) (See Weber et al., Generation of Tumor Antigen-Specific T Cell Lines from Pediatric Patients with Acute Lymphoblastic Leukemia—Implications for Immunotherapy, Clin Cancer Res. 2013 Sep. 15; 19(18): 5079-5091 (FIG. 1B)). Accordingly, while T-cell populations produced by these methods may provide potent and durable responses in certain patients, the variability of the process makes deriving consistently reproducible products challenging. This variability may account for the limitation in efficacy seen in some patients due to an unfavorable or ineffective ratio of T-cell subsets and/or other immune effector cells.

Unlike the non-selected, non-fixed ratio of adoptive T-cell compositions, for example as exemplified in FIG. 1B of Weber et al. (provided herein as FIG. 1), the present invention reduces the significant variability of these compositions. Furthermore, as shown herein, it has been discovered that lymphocytic cell compositions which show efficacy in treating tumors, for example solid tumors, are comprised of multi-lymphocytic cell subsets (see, e.g., Example 4, FIG. 4A; Table 1). Importantly, as further described herein, patients receiving cell compositions comprised of multi-lymphocytic cell subsets show enhanced tumor associated epitope spreading (see, e.g., Example 4, FIG. 7) following administration.

The different non-engineered lymphocytic cell subsets within the cell composition are selected from a combination of activated CD4$^+$ T-cells (T-helper cells), CD8$^+$ T-cells (Cytotoxic T-Lymphocytes), CD3$^+$/CD56$^+$ Natural Killer T-cells (CD3$^+$ NKT), and TCR γδ T-cells (γδ T-cells) to derive at the fixed ratios described herein. In particular, the cell population includes CD4$^+$ T-cells and CD8$^+$ T-cells that have been primed and are capable of targeting one or more specific antigens for tumor killing and/or cross presentation. The cell composition optionally further comprises activated γδ T-cells and/or activated CD3$^+$ NKT-cells capable of mediating anti-tumor responses. By providing a standardized, non-naturally occurring ratio of multiple activated immune effector cells with differing in vivo immune effector and biological functions, long lasting and durable responses to multiple tumor-types are possible, increasing the ability of the administered cell composition to induce tumor specific epitope spreading, and reducing tumor immune surveillance avoidance. The inclusion of activated CD3$^+$ NKT-cells and/or γδ T-cells results in the additional release of cytokines that may induce bystander T-cell activation and thus recruit other lymphocytes, including CD8$^+$ T-cells, to aid in tumor cytolysis, including in epitope spreading. Furthermore, by producing fixed ratios of activated immune effector cells, consistent and reproducible cell compositions are provided, reducing the variability of administered product received by different patients. In some embodiments, the cell compositions further comprise activated CD3$^-$, CD56$^+$, CD16$^+$ Natural Killer cells (CD3$^-$ NK cells) and/or CD14$^+$ monocytes. The cells are not engineered cells, for example, the cells do not contain an exogenous chimeric antigen receptor.

In one aspect of the present invention, the composition provides non-engineered T-cell compositions that include a fixed ratio of a population of different lymphocytic cell subsets comprising CD4$^+$ T-cells, CD8$^+$ T-cells, and CD3$^+$ NKT-cells useful in treating disorders or diseases such as an infection or cancer. In some embodiments, the different lymphocytic cell subsets of the composition have been exposed ex vivo to one or more specific target antigens or peptide segments of one or more antigens, for example in an antigenic peptide library. In some embodiments, only the CD4$^+$ T-cells and CD8$^+$ T-cells have been exposed ex vivo to one or more specific antigens. The CD4$^+$ T-cells and CD8$^+$ T-cells have been primed and expanded and are capable of targeting one or more specific target antigens. The CD4$^+$ T-cells and CD8$^+$ T-cells can be primed and expanded in the same reaction, or separately and recombined in a fixed ratio described herein. In some embodiments, the CD4$^+$ T-cells and CD8$^+$ T-cells prior to priming and expansion, are naïve to the specific target antigens. In some embodiments, the CD4$^+$ T-cells and CD8$^+$ T-cells are naïve cells, and are selected for prior to priming and expansion, for example through the selection of CD45RA$^+$ cells. The CD3$^+$ NKT-cells in the composition may be activated during the manufacturing process of the CD4$^+$ T-cells and CD8$^+$ T-cells, or activated separately and recombined with the CD4$^+$ T-cells and CD8$^+$ T-cells in a fixed ratio described herein. In some embodiments, the composition comprises about a 1:1:1 ratio (+/−5-10%) of CD4$^+$ T-cells: CD8$^+$ T-cells: CD3$^+$ NKT-cells. In some embodiments, the composition comprises between about 15% and 25% CD4$^+$ T-cells, between about 45% and 55% CD8$^+$ T-cells, and between about 25% and 35% CD3$^+$ NKT-cells. In some embodiments, the composition comprises about 20% (+/−3-5%) CD4$^+$ T-cells, about 50% (+/−3-5%) CD8$^+$ T-cells, and about 30% (+/−3-5%) CD3$^+$ NKT-cells, resulting in a cell composition comprising about a 0.2:0.5:0.3 ratio of CD4$^+$ T-cells:CD8$^+$ T-cells:CD3$^+$ NKT-cells. In some embodiments, the composition comprises between about 30% and 40% CD8$^+$ T-cells, between about 5% and 15% CD4$^+$ T-cells, and between about 7.5% and 15% CD3$^+$ NKT-cells. In some embodiments, the composition comprises between at least about 30% CD8$^+$ T-cells, at least about 10% CD4$^+$ T-cells, and at least about 10% CD3$^+$ NKT-cells. In some embodiments, the composition comprises about 35% CD8$^+$ T-cells (+/−3%), about 10% CD4$^+$ T-cells (+/−3-5%), and about 10% CD3$^+$ NKT-cells (+/−3-5%). In some embodiments, the composition comprises CD8$^+$ T-cells, CD4$^+$ T-cells, and CD3$^+$ NKT-cells in about a 3.5:1:1 ratio (+/−5-10%). In some embodiments, the cells have been exposed to and/or primed against one or more targeted antigens selected from a TAA, a VATA, a glycolipid, or a combination thereof. In some embodiments, the cells are exposed to one or more TAAs, VATAs, or a combination thereof, and further exposed to one or more glycolipids, for example one or more gangliosides. In some embodiments, the CD3$^+$ NKT-cells are exposed to one or more TAAs, VATAs, or a combination thereof, and further exposed to one or more glycolipids, for example one or more gangliosides. In some embodiments, the CD3$^+$ NKT-cells are exposed to one or more glycolipids, for example one or more gangliosides. In some embodiments, the lymphocytic cell subsets are naïve to the targeted antigen to which it is exposed and/or primed. In some embodiments, the cell compositions further comprise activated CD3$^-$ NK cells and/or CD14$^+$ monocytes. In some embodiments, the cell compositions further comprise at least about 5% activated CD3$^-$ NK cells. In some embodiments, the cell compositions further comprise at least about 10% activated CD3$^-$ NK cells. In some embodiments, the cell compositions further comprise activated TCR γδT-cells. In some embodiments, the cell compositions further comprise at least about 5% activated TCR γδT-cells. In some embodiments, the cell compositions further comprise at least about 10% activated TCR γδT-cells In an alternative aspect of the present invention, the composition provides non-engineered T-cell compositions that include a fixed ratio of a population of different lymphocytic cell subsets comprising TCR αβ T-cells (αβ T-cells) and γδ T-cells useful in treating disorder or disease such as an infection or cancer. In some embodiments, the αβ T-cells and γδ T-cells have been exposed ex vivo to one or more specific target antigens or peptide segments of one or more antigens, for example in an antigenic peptide library. In some embodiments, only the αβ T-cells have been exposed ex vivo to one or more specific antigens. The αβ T-cells of the composition, which include $CD4^+$ and $CD8^+$ T-cells, have been primed and are capable of targeting one or more specific antigens. In some embodiments, the $CD4^+$ T-cells and $CD8^+$ T-cells prior to priming and expansion, are naïve to the specific target antigens. In some embodiments, the $CD4^+$ T-cells and $CD8^+$ T-cells are naïve cells, and are selected for prior to priming and expansion, for example through the selection of $CD45RA^+$ cells. The γδ T-cells in the composition may be activated during the manufacturing process of the αβ T-cells, or activated separately and recombined with the αβ T-cells in a fixed ratio described herein. In some embodiments, the composition comprises about a 1:1 ratio (+/−5-10%) of αβ T-cells: γδ T-cells. In some embodiments, the composition comprises from about 55% to about 65% αβ T-cells and from about 35% to about 45% γδ T-cells. In some embodiments, the composition comprises about 60% (+/−3%) αβ T-cells and about 40% (+/−3-5%) γδ T-cells. In some embodiments, the αβ T-cells comprise about a 1:1 ratio (+/−5-10%) of $CD8^+$ T-cells: $CD4^+$ T-cells. In some embodiments, the cell composition comprising as T-cells and γδ T-cells includes αβ T-cells that are from about 55% to about 65% of $CD8^+$ T-cells and from about 35% to about 45% of $CD4^+$ T-cells. In some embodiments, the cell composition comprising αβ T-cells and γδ T-cells includes αβ T-cells that are between about 60% (+/−3-5%) $CD8^+$ T-cells and about 40% (+/−3-5%) of $CD4^+$ T-cells, resulting in a cell composition comprising about a 0.36:0.24:0.4 ratio of $CD8^+$ T-cells:$CD4^+$ T-cells: γδ T-cells. In some embodiments, the γδ T-cells are predominantly Vγ9Vδ2 T-cells, for example, at least about 70%, 75%, 80%, 85%, 90% or more of the γδ T-cells are Vγ9Vδ2 T-cells. In some embodiments, the cells have been exposed to one or more targeted antigens selected from a TAA, a VATA, or a combination thereof. In some embodiments, the lymphocytic cell subsets are naïve to the targeted antigen to which it is exposed and/or primed. The $CD4^+$ T-cells and $CD8^+$ T-cells comprising the αβ T-cells portion of the composition can be primed and expanded in the same reaction, or separately and recombined in a fixed ratio described herein. In some embodiments, the γδ T-cells are activated in the presence of zoledronic acid and IL-2. In some embodiments, the cell compositions further comprise activated $CD3^-$ NK cells and/or $CD14^+$ monocytes. In some embodiments, the cell compositions further comprise at least about 5% activated $CD3^-$ NK cells. In some embodiments, the cell compositions further comprise at least about 10% activated CD3-NK cells.

In still other alternative aspects, the composition provides non-engineered T-cell compositions that include a fixed ratio of a population of different lymphocytic cell subsets comprising αβ T-cells, γδ T-cells, and $CD3^+$ NKT-cells useful in treating disorder or disease such as an infection or cancer. In some embodiments, the lymphocytic cell subsets of the composition have been exposed ex vivo to one or more specific target antigens or peptide segments of one or more antigens, for example in an antigenic peptide library. In some embodiments, only the αβ T-cells have been exposed ex vivo to one or more specific target antigens. The αβ T-cells of the composition, which include $CD4^+$ and $CD8^+$ T-cells, are primed ex vivo to one or more specific target antigens. In addition, the γδ T-cells and $CD3^+$ NKT-cells may be activated during the manufacturing process of the αβ T-cells, or each activated separately and recombined with the as T-cells in a fixed ratio described herein. Likewise, the $CD4^+$ T-cells and $CD8^+$ T-cells comprising the αβ T-cells portion of the composition can be primed and expanded in the same reaction, or separately and recombined in a fixed ratio described herein. In some embodiments, the αβ T-cells prior to priming and expansion, are naïve to the specific target antigens. In some embodiments, the αβ T-cells are naïve cells, and are selected for prior to priming and expansion, for example through the selection of $CD45RA^+$ cells. In some embodiments, the composition comprises about a 1:1:1 ratio (+/−5-10%) of αβ T-cells: γδ T-cells: $CD3^+$ NKT-cells. In some embodiments, the composition comprises between about 25% and 35% αβ T-cells, between about 25% and 35% γδ T-cells, and between about 35% and 45% $CD3^+$ NKT-cells. In some embodiments, the composition comprises about 30% (+/−3-5%) αβ T-cells, about 30% (+/−3%) 6 T-cells, and about 40/(+/−3-5%) $CD3^+$ NKT-cells, resulting in a cell composition comprising about a 0.3:0.3:0.4 ratio of αβ T-cells: γδ T-cells: $CD3^+$ NKT-cells. In some embodiments, the αβ T-cells are comprised of a 1:1 ratio (+/−5-10%) of $CD8^+$ T-cells: $CD4^+$ T-cells, resulting in a cell composition comprising about a 0.15:0.15:0.3:0.4 ratio of $CD8^+$ T-cells:$CD4^+$ T-cells: γδ T-cells:$CD3^+$ NKT-cells. In some embodiments, the αβ T-cells are comprised of between about 55% to about 65% of $CD8^+$ T-cells and between about 35% to about 45% of $CD4^+$ T-cells. In some embodiments, the αβ T-cells are comprised of about 60% (+/−3%) $CD8^+$ T-cells and about 40% (+/−3%) of $CD4^+$ T-cells, resulting in a cell composition comprising about a 0.18:0.12:0.3:0.4 ratio of $CD8^+$ T-cells:$CD4^+$ T-cells: γδ T-cells:$CD3^+$ NKT-cells. In some embodiments, the γδ T-cells are predominately Vγ9Vδ2 T-cells, for example, at least about 70%, 75%, 80%, 85%, 90% or more of the γδ T-cells are Vγ9Vδ2 T-cells. In some embodiments, the cells have been exposed to and/or primed against one or more targeted antigens selected from a TAA, a VATA, a glycolipid, or a combination thereof. In some embodiments, the cells are exposed to one or more TAAs, VATAs, a combination thereof and further exposed to one or more glycolipids, for example one or more gangliosides.

The disclosure also relates to a method of making or priming a lymphocytic cell composition comprising exposing one or a plurality of T-cell subsets to one or more glycolipids, for example one or more gangliosides. In some embodiments, the $CD3^+$ NKT-cells are exposed to one or more TAAs, VATAs, or combination thereof, and further exposed to one or more glycolipids, for example one or more gangliosides. In some embodiments, the $CD3^+$ NKT-cells are exposed to one or more glycolipids, for example one or more gangliosides. In some embodiments, the γδ T-cells are activated in the presence of zoledronic acid and IL-2. In some embodiments, the lymphocytic cell subsets are naïve to the targeted antigen to which it is exposed and/or primed. In some embodiments, the cell compositions further comprise activated $CD3^-$ NK cells and/or $CD14^+$ monocytes. In some embodiments, the cell compositions further comprise at least about 5% activated $CD3^-$ NK cells. In some embodiments, the cell compositions further comprise at least about 10% activated $CD3^-$ NK cells.

In still other alternative aspects, compositions are disclosed comprising the fixed ratio of a population of different non-engineered lymphocytic cell subsets comprising αβ T-cells, γδ T-cells, and $CD3^+$ NKT-cells comprises at least about 35% αβ T-cells, at least about 30% γδ T-cells, and at least about 10% $CD3^+$ NKT-cells. In some embodiments, the composition further comprises at least about 5% $CD3^-$, $CD56^+$, $CD16^+$ Natural Killer cells ($CD3^-$ NK cells). In some embodiments, the lymphocytic cell subsets of the composition have been exposed ex vivo to one or more specific target antigens or peptide segments of one or more antigens, for example in an antigenic peptide library. In some embodiments, only the αβ T-cells of the composition have been exposed ex vivo to one or more specific target antigens. The αβ T-cells of the composition, which include $CD4^+$ and $CD8^+$ T-cells, are primed ex vivo to one or more specific target antigens. In addition, the γδ T-cells and $CD3^+$ NKT-cells, and optionally $CD3^-$ NK cells, may be activated during the manufacturing process of the αβ T-cells, or each activated separately and recombined with the as T-cells in a fixed ratio described herein. Likewise, the $CD4^+$ T-cells and $CD8^+$ T-cells comprising the αβ T-cells portion of the composition can be primed and expanded in the same reaction, or separately and recombined in a fixed ratio described herein. In some embodiments, the αβ T-cells are naïve cells, and are selected for prior to priming and expansion, for example through the selection of $CD45RA^+$ cells. In some embodiments, the composition comprises between about 35% and 45% αβ T-cells, between about 30% and 40% S T-cells, and from about 10% to about 20% $CD3^+$ NKT-cells, and optionally between about 5% and 10% $CD3^-$ NK cells. In some embodiments, the composition comprises about 40% (+/−3-5%) αβ T-cells, about 35% (+/−3-5%) γδ T-cells, and about 15% (+/−3-5%) $CD3^+$ NKT-cells, and optionally about 8% (+/−3-5%) $CD3^-$ NK cells. In some embodiments, the αβ T-cells are comprised of a 1:1 ratio (+/−5-10%) of $CD8^+$ T-cells: $CD4^+$ T-cells. In some embodiments, the αβ T-cells are comprised of between about 55% to about 65% of $CD8^+$ T-cells and between about 35% to about 45% of $CD4^+$ T-cells. In some embodiments, the αβ T-cells are comprised of about 60% (+/−3-5%) $CD8^+$ T-cells and about 40% (+/−3-5%) of $CD4^+$ T-cells. In some embodiments, the αβ T-cells are comprised of less than about 55% of $CD4^+$ T-cells. In some embodiments, the γδ T-cells are predominantly Vγ9Vδ2 T-cells, for example, at least about 70%, 75%, 80%, 85%, 90% or more of the γδ T-cells are Vγ9Vδ2 T-cells. In some embodiments, the cells have been exposed to and/or primed against one or more targeted antigens selected from a TAA, a VATA, a glycolipid, or a combination thereof. In some embodiments, the cells are exposed to one or more TAAs, VATAs, a combination thereof and further exposed to one or more glycolipids, for example one or more gangliosides. In some embodiments, the $CD3^+$ NKT-cells are exposed to one or more TAAs, VATAs, or combination thereof, and further exposed to one or more glycolipids, for example one or more gangliosides. In some embodiments, the $CD3^+$ NKT-cells are exposed to one or more glycolipids, for example one or more gangliosides. In some embodiments, the γδ T-cells are activated in the presence of zoledronic acid and IL-2. In some embodiments, the γδ T-cells are activated in the presence of zoledronic acid and human IL-2. In some embodiments, the lymphocytic cell subsets are naïve to the targeted antigen to which it is exposed and/or primed. In some embodiments, the cell compositions further comprise activated $CD3^-$ NK cells and/or $CD14^+$ monocytes. In some embodiments, the cell compositions further comprise at least about 5% activated $CD3^-$ NK cells. In some embodiments, the cell compositions further comprise at least about 10% activated CD3-NK cells.

In certain aspects of the invention, the fixed ratio of different lymphocytic cell subsets can be administered to a patient as a single combined product, for example a pre-mixed population of cells comprising the fixed ratios described herein, or in a fixed ratio wherein each specific lymphocytic cell subset is maintained as a single homogenous cell composition and individually administered to the patient in the fixed ratio as described herein. In embodiments described herein, the total number of cells administered to the patient is between about $1\times10^6$ cells/$m^2$ to about $5\times10^8$ cells/$m^2$. In certain subsets, the composition of cells described herein can be administered one or more times, for example, as a maintenance dose or as residual disease begins to progress.

The αβ T-cell subsets, including the $CD4^+$ T-cells and $CD8^+$ T-cells of the compositions described herein, are primed ex vivo against a specific antigen or group of antigens of interest, for example one or more TAAs, one or more VATAs, or a combination thereof, by exposing the cells under priming conditions during expansion to the antigenic peptide or protein of interest. For example, the αβ T-cell subsets can be primed against one or more epitopes from a single TAA and/or VATA, or one or more epitopes from multiple TAAs and/or VATAs, or a combination thereof. In some embodiments, the αβ T-cells, including the $CD4^+$ T-cells and $CD8^+$ T-cells, are primed against multiple epitopes of a targeted antigen, for example via exposure to an overlapping peptide pools from a viral or tumor antigen under priming conditions. In some embodiments, the αβ T-cells cells are primed against multiple epitopes of multiple targeted antigens, for example via exposure to overlapping peptide pools from several viral and/or tumor antigens under priming conditions. The specific combination of antigens the αβ T-cell population is primed against will be dependent on the specific antigenic makeup of the targeted cell or virus.

In some embodiments, the γδ T-cells and/or $CD3^+$ NKT-cells of the compositions described herein are similarly exposed to a specific antigen or group of antigens of interest, for example one or more TAAs, one or more VATAs, or a combination thereof, during the priming of the αβ T-cells. By culturing and expanding the γδ T-cells and/or $CD3^+$ NKT-cells with the αβ T-cells, it has been found that these cells can be activated during the manufacturing process. In some embodiments, the one or more antigens the cells are exposed to include one or more glycolipids, for example but not limited to, a ganglioside. In some embodiments, the $CD3^+$ NKT-cells are exposed to only one or more glycolipids, for example but not limited to a ganglioside. In some embodiments, the γδ T-cells are activated in the presence of zoledronic acid and IL-2.

In some embodiments, the γδ T-cells and/or $CD3^+$ NKT-cells and/or $CD3^-$ NK-cells of the compositions are activated separately from the αβ T-cells. The separately activated lymphocytic subsets can then either be recombined prior to administration to derive the specific ratios described herein, or, in an alternative embodiment, kept separate and administered as discrete subsets in the ratios defined herein.

In some embodiments, the γδ T-cells and/or CD3+ NKT-cells and/or $CD3^-$ NK-cells of the compositions may be activated with the αβ T-cells, and then separated. Following separation, the activated lymphocytic subsets can then either be recombined prior to administration to derive the specific ratios described herein, or, in an alternative embodiment, kept separate and administered as discrete subsets in the ratios defined herein.

In some embodiments, the cells of the lymphocytic cell composition described herein are exposed and/or primed against one or more TAAs, VATAs, glycolipids, or combinations thereof. In some embodiments, the fixed ratios of lymphocytic cell subsets in the cell compositions described herein may contain a fixed ratio of cells exposed to and/or primed against each antigen. For example, if more than one antigen is targeted, each lymphocytic cell subset that makes up the cell composition may include cells exposed to and/or primed against each antigen in a fixed ratio within that lymphocytic cell subset. For example, if three antigens are being targeted, each lymphocytic cell subset that makes up the cell composition is provided in the ratios described herein, and the cells within each subset are in a fixed ratio of cells that have been exposed to and/or primed against the three targeted antigens, for example in a 1:1:1 (+/−5-10%) ratio. In an alternative embodiment, the ratio of antigen specific cells is reflective of the expression pattern of antigens in a patient's tumor sample.

In some aspects of the present invention, the cells of the lymphocytic cell compositions described herein are directed to one or more TAAs, VATAs, glycolipids, or combination thereof that is associated with the underlying disease of the patient to which the cell composition will be administered, as further described herein. TAAs and VATAs include, but are not limited to, for example, PRAME, Survivin, WT-1, NY-ESO-1, MAGE A3, CMVpp65, HPVE6, HPVE7, EBV-associated antigens, HTLV-associated antigens, HBV-associated antigens, and HCV-associated antigens. In some embodiments, the cells of the lymphocytic cell composition can be further exposed to one or more glycolipids. In some embodiments, lymphocytic cell compositions containing $CD3^+$ NKT-cells are exposed to one or more glycolipids. In some embodiments, only the $CD3^+$ NKT-cells of the lymphocytic cell compositions are exposed to one or more glycolipids. In some embodiments, the glycolipid is a ganglioside selected from N-glycolyl-GM3, GD2, GD3, and GM2. In some embodiments, the antigens are PRAME, Survivin, and WT-1.

Also provided herein are methods for isolating, selecting, expanding, culturing and/or enriching the different lymphocytic cell subsets to arrive at the isolated fixed ratio cell population provided herein starting from an initial starting sample, for example an apheresis sample, leukapheresis sample, or sample containing peripheral blood mononuclear cells (PBMCs). Alternatively, the fixed ratio cell population provided herein can be arrived at by combining the cells separately following initial isolation or selection of each lymphocytic cell subset and exposing them to and/or priming them against a targeted antigen.

The initial lymphocyte population expanded ex vivo for inclusion in the cell compositions described herein can be allogeneic or autologous. In the case of an allogeneic sample, the sample can be derived from a donor whose lymphocytes are naïve to the associated target antigen, a healthy donor who may have lymphocytes previously primed to one or more targeted antigens (e.g., a donor seropositive to an antigen), or a cord-blood sample. In some embodiments, the initial lymphocyte cells which are expanded and primed ex vivo are from a naïve allogeneic donor. To the extent that an allogeneic sample is used as the starting material, the lymphocytes and patient recipient may be HLA matched at one or more HLA alleles in order to minimize graft versus host disease and maximize activity.

In some embodiments, the cells are selected for prior to combining into the specific ratios provided herein through immunoaffinity-based selection, such as binding to antibodies or other binding molecules recognizing surface markers on the cells. For example, following expansion and activation of a heterogenous population of lymphocytes, a first selection can be performed by enriching from the cell population one of the desired cell-types, for example $CD4^+$ T-cells, or $CD8^+$ T-cells, or $CD3^+$ NKT-cells to generate a first selected population and a non-selected population, and from the non-selected population performing a second selection by enriching for the other of $CD4^+$ T-cells, or $CD8^+$ T-cells, or $CD3^+$ NKT-cells to generate a second selected population and a non-selected population, wherein the method produces a composition of cells containing cells enriched for $CD4^+$ cells, cells enriched for $CD8^+$, and cells enriched for $CD3^+$ NKT-cells. Similar selection procedures can be performed with respect to any of the desired population of enriched cells described herein.

In some embodiments, the second selection is carried out by enriching for the other of the lymphocytic cell subtypes from the non-selected population generated by the first selection. For example, the negative fraction from a first selection is not discarded but rather is used as the basis for a further selection to enrich for another cell type. In general, where the cell subset enriched for in the first selection is, for example a $CD4^+$ T-cell subset (or where the first selection enriches for $CD4^+$ T-cells), it will follow that the first selection is designed such that it does not enrich for cells of the other subtype to be enriched for in the subsequent selections. For example, in some embodiments, the first selection enriches for $CD4^+$ T-cells and does not enrich for $CD8^+$ T-cells or $CD3^+$ NKT-cells, the second selection enriches for $CD8^+$ T-cells from the negative fraction recovered from the first selection, and the third selection enriches for $CD3^+$ NKT cells recovered from the second selection. Likewise, in general, where the T cell subset enriched for in the first selection is a $CD8^+$ T-cell subset (or where the first selection enriches for $CD8^+$ T-cells), it will follow that the first selection is designed such that it does not enrich for cells of the other subtype to be enriched for in subsequent selections. For example, in some embodiments, the first selection enriches for $CD8^+$ T-cells and does not enrich for $CD4^+$ T-cells, the second selection enriches for $CD4^+$ T-cells from the negative fraction recovered from the first selection, and the third selection enriches for $CD3^+$ NKT-cells from the negative fraction recovered from the second selection.

Certain methods of selecting specific cell types are generally known in the art. For example, in some embodiments, selections are performed by immunoaffinity-based selection, such as by contacting cells with an antibody on a solid support that specifically binds a cell surface marker, such as CD4, CD8, CD56, or other cell surface marker specific for the desired cell. The solid support can be, for example, a sphere, such as a bead, such as a microbead or nanobead. In some embodiments, the bead can be a magnetic bead. In some embodiments, the solid support can be a column or other vessel to effect column chromatography. In some embodiments, the antibody contains one or more binding partners capable of forming a reversible bond with a binding reagent immobilized on the solid surface, such as a sphere or chromatography matrix. In some embodiments, the antibody is reversibly immobilized to the solid surface. In some embodiments, cells expressing a cell surface marker bound by the antibody on said solid surface are capable of being recovered from the matrix by disruption of the reversible binding between the binding reagent and binding partner.

Binding reagents are generally known in the art, for example streptavidin, biotin, or analogs thereof.

In an alternative embodiment, lymphocytic cell subsets can be isolated first by specific subset, then exposed to and/or primed against one or more specific antigens and expanded to generate a population of a specific cell subset. For example, δγ T-cells can be initially isolated, activated, and expanded separately from, e.g., αβ T-cells. Each separate cell subset can then be combined in a fixed ratio to provide a single composition as described herein or administered to a patient as separate cell subsets in the fixed ratios described herein.

In an alternative embodiment, lymphocytic cell subsets can be exposed to and/or primed against an antigen and expanded separately based on a specific protocol and then purified. For example, δγ T-cells can be primed and expanded separately from, e.g., αβ T-cells. Each separate cell subset can then be combined in a fixed ratio to provide a single composition as described herein or administered with the separate cell subset in the fixed ratios described herein.

The non-engineered cells of the described compositions described herein can be subjected to further selection. For example, a particular lymphocytic cell for inclusion in the fixed ratios described herein can undergo further selection through depletion or enriching for a sub-population. For example, following priming, expansion, and selection, the cells can be further selected for other cluster of differentiation (CD) markers, either positively or negatively. For example, following selection of for example $CD4^+$ T-cells, the $CD4^+$ T-cells can be further subjected to selection for, for example, central memory T-cells ($T_{cm}$). For example, the enrichment for $CD4^+$ $T_{cm}$ cells comprises negative selection for cells expressing a surface marker present on naïve T cells, such as CD45RA, or positive selection for cells expressing a surface marker present on $T_{cm}$ cells and not present on naïve T-cells, for example CD45RO, CD62L, CCR7, CD27, CD127, and/or CD44. Likewise, following selection of γδ T-cells, the γδ T-cells can be subject to further selection for Vγ9Vδ2 T-cells. In addition, as described further herein, the cell populations described herein can be further selected to eliminate cells expressing certain exhaustion markers, for example, programmed cell death-1 (PD-1), CTLA-4/CD152 (Cytotoxic T-Lymphocyte Antigen 4), LAG-3 (Lymphocyte activation gene-3; CD223), TIM-3 (T cell immunoglobulin and mucin domain-3), 2B4/CD244/SLAMF4, CD160, and TIGIT (T cell Immunoreceptor with Ig and ITIM domains). In some embodiments, the lymphocytic cell compositions described herein have less than about 1%, 0.5%, or 0.1% $CD223^+$ cells.

The non-engineered cell compositions described herein can be administered to a patient to treat an abnormal cellular proliferation such as a tumor or malignancy, for example in certain embodiments the patient has a hematological malignancy such as, but not limited to, leukemia such as acute lymphocytic leukemia (ALL)—also known as acute lymphoblastic leukemia or acute lymphoid leukemia (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)).

Alternatively, the cell compositions described herein can be administered to a patient with a solid tumor, for example but not limited to, a carcinoma, sarcoma, or blastoma. In some embodiments, the solid tumor is selected from Wilms tumor, rhabdomyosarcoma, neuroblastoma, soft tissue sarcoma, Ewing sarcoma, and osteosarcoma. In other embodiments, the solid tumor is, for example but not limited to, breast, prostate, lung, pancreatic, colon, or brain tumors. The cell compositions described herein can also be administered to a patient to treat viral-induced tumors, for example but not limited to: hepatitis B or hepatitis C virus induced cirrhosis or liver cancer; papillomavirus induced cervical, anogenital, and head and neck cancers; Epstein-Barr virus induced Burkitt's lymphoma and nasopharyngeal carcinoma; herpesvirus associated Kaposi's sarcoma; human T-cell lymphotropic virus associated adult T-cell leukemia; and HIV-related cancers.

Also provided herein are kits comprising pharmaceutical and therapeutic compositions containing the isolated cells and populations in a fixed ratio as described herein. In some embodiments, the kit may contain one or more vials or infusion bags of a fixed ratio of multiple ex vivo primed lymphocytic cell subsets described herein. For example, the kit may contain a single dose unit of a population of different lymphocytic cell subsets according to the fixed ratios described herein. Alternatively, the kit may contain multiple vials or infusion bags, wherein each vial or infusion bag comprises a single lymphocytic cell subset, and wherein the collective vials or infusion bags in the kit provide, upon administration, a fixed ratio of multiple ex vivo primed lymphocytic cell subsets described herein. For example, the kit may contain multiple vials or infusion bags, wherein each vial or infusion bag contains, for example but not limited to αβ T-cells, 76 T-cells, or $CD3^+$ NKT-cells for administration to a patient, and wherein each vial or infusion bag contains a population of the respective lymphocytic cell subset in a concentration representative of a specific ratio in relation to the other cell subsets contained in the kit, for example, 1:1:1 (+/−5-10%) or 0.3:0.3:0.4 (+/−5-10%).

DETAILED DESCRIPTION OF THE INVENTION

Prior strategies for ex vivo expansion of non-engineered T-cells have generally focused on the priming and expansion of limited subsets of T-cell populations, primarily and predominantly $CD8^+$ or $CD8^+/CD4^+$ T-cells. Thus, the repertoire of activated effector cells targeting tumors introduced to the patient during treatment may be limited and focused, and may require further in vivo mechanisms to recruit additional immune effector cells in establishing a more complete immune response. This reliance on in vivo mechanisms is challenging, especially given that many patients receiving T-cell therapies have previously undergone rigid chemotherapeutic regimens, altering the levels and, often times effectiveness, of effector cells. For example, breast cancer patients receiving chemotherapy had significant changes in pre- and post-chemotherapy lymphocytic cell populations and function. Within 2 weeks of receiving chemotherapy, B-cells, T-cells and NK-cells were significantly reduced ($p<0.001$). B-cells demonstrated particularly dramatic depletion, falling to 5.4% of pre-chemotherapy levels. Levels of all effector cells recovered to some extent, although B and $CD4^+$ T cells remained significantly depleted even 9 months post-chemotherapy ($p<0.001$). Phenotypes of repopulating B and $CD4^+$ T cells were significantly different from, and showed no sign of returning to, pre-chemotherapy profiles (see Verma et al., Lymphocyte depletion and repopulation after chemotherapy for primary breast cancer, Breast Cancer Res. 2016; 18:10).

The prior strategies employed in the ex vivo expansion of non-engineered T-cells by antigen-specific stimulation of autologous or allogeneic T-cells may result in heterogeneous end products, which can vary from one sample or batch to another due to the significant variability in starting materials. Unlike traditional pharmaceutical drugs that can be produced and rigidly controlled, non-engineered T-cell therapies, whether autologous or allogeneic, are composed of highly complex mixtures of hundreds of millions to billions of cells, with variable populations of T-cell subsets, for example widely varying populations of $CD4^+$ and $CD8^+$ T-cells.

Figure 1:
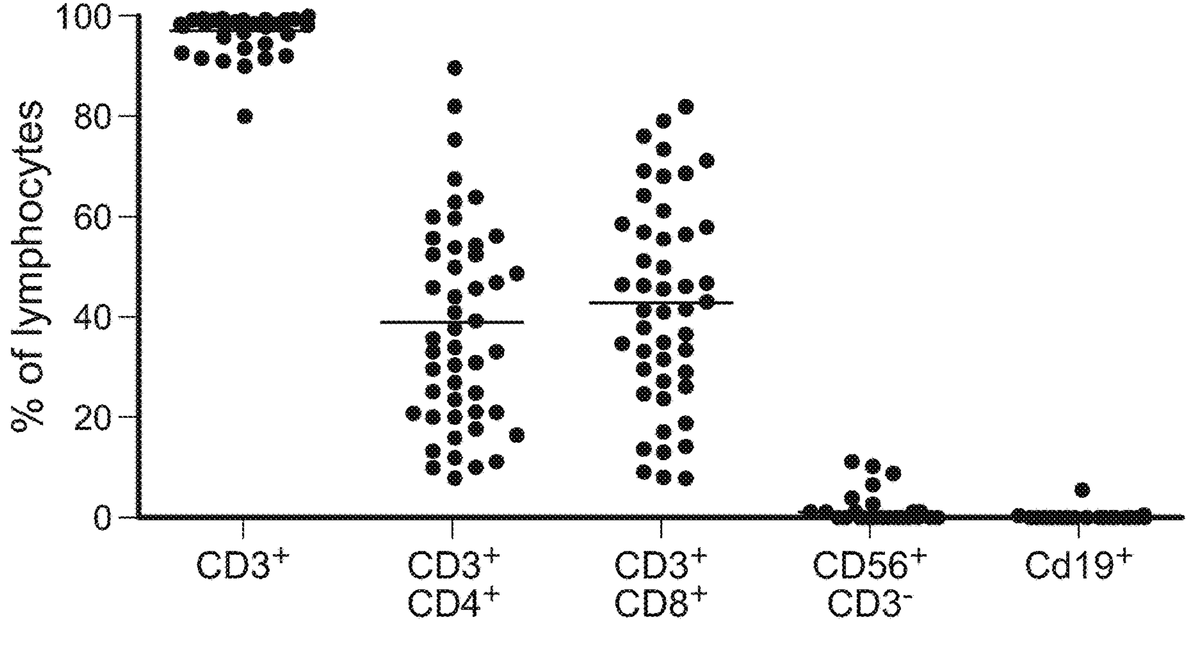
FIG. 1: Phenotyping of the ex vivo expanded non fixed ratio cell lines according to the prior art showed a mean $CD3^+$ content of 97.2% (range 80.3-99.9%) and varying distribution of $CD4^+$ (mean 38.4% range 8.3-89.4%) and $CD8^+$ (mean 42.6% range 7.9-82.1%) T cells, few NK cells (mean 1.3% range 0-10.9%) and rare residual B cells (mean 0.2% range 0-5.8%). The x-axis shows the cell type and the y-axis shows the percentage of lymphocytes. See Weber et al., Generation of Tumor Antigen-Specific T Cell Lines from Pediatric Patients with Acute Lymphoblastic Leukemia—Implications for Immunotherapy, Clin Cancer Res. 2013 Sep. 15; 19(18):5079-5091 (FIG. 1B).

For example, Weber et al. describe the generation of lymphocytic cell lines wherein autologous peripheral blood mononuclear cells were stimulated ex vivo with autologous dendritic cells pulsed with complete peptide libraries of WT1, Survivin, MAGE-A3 and PRAME. Phenotyping of the ex vivo expanded lymphocytic cell lines showed a mean $CD3^+$ content of 97.2% (range 80.3-99.9%) and varying distribution of $CD4^+$ (mean 38.4% range 8.3-89.4%) and $CD8^+$ (mean 42.6% range 7.9-82.1%) T cells, few NK cells (mean 1.3% range 0-10.9%) and rare residual B cells (mean 0.2% range 0-5.8%) (See Weber et al., Generation of Tumor Antigen-Specific T Cell Lines from Pediatric Patients with Acute Lymphoblastic Leukemia—Implications for Immunotherapy, Clin Cancer Res. 2013 Sep. 15; 19(18): 5079-5091 (FIG. 1)).

Accordingly, while engineered T-cell populations produced by these methods may provide potent and durable responses in certain patients, the variability of the process makes deriving consistently reproducible products challenging. This variability may account for the limitation in efficacy seen in some patients due to an unfavorable or ineffective ratio of T-cell subsets and/or other immune effector cells.

Efforts have been made to provide more homogenous or fixed ratios of engineered CAR-T-cell subset populations. For example, Turtle et al. describe the use of an autologous CD-19 CAR-T product having fixed ratios of $CD4^+/CD8^+$ cells at 1:1 for the treatment of B-ALL (Turtle et al., CD19 CAR-T cells of defined $CD4^+$:$CD8^+$ composition in adult B cell ALL patients, JCI 2016 126(6):2123-2138) and non-Hodgkin's lymphoma (Turtle et al., Immunotherapy of non-Hodgkin's lymphoma with a defined ratio of $CD8^+$ and $CD4^+$ CD19-specific chimeric antigen receptor-modified T cells, Sci. Transl. Med. 2016 8(355):355ra116). While these efforts result in a more consistent CAR-T cell subset population, the resultant population of expanded T-cells is narrowly homogeneous and may lack other critical immune effector cell subsets necessary to provide a more efficacious immune response applicable from patient to patient.

The present invention provides isolated, non-engineered cell compositions for the treatment of abnormal cellular proliferation such as cancer, including hematological and solid tumors, comprising an optimized, standardized, non-naturally occurring fixed ratio of multiple ex vivo activated lymphocytic cell subsets, including specific immune effector cells directed to specific tumor associated antigens (TAAs), viral associated tumor antigens (VATA), glycolipids, or a combination thereof. By selecting specific fixed ratios of different lymphocytic cell subsets, an immune response which is comprehensive and broad in biological and immune effector function is provided, enhancing the ability of the administered cells to mount an effective and robust immune response.

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. The term "about" as used herein when referring to a measurable value such as an amount, a temporal duration, and the like, is meant, in some embodiments, to encompass variations of ±20%, ±10%, ±5%, ±1%, ±0.5%, or ±±0.1% from the specified value, as such variations are appropriate to perform the disclosed methods.

The term "allogeneic" as used herein refers to medical therapy in which the donor and recipient are different individuals of the same species.

An "antigen" includes molecules, such as polypeptides, peptides, or glyco- or lipo-peptides that are recognized by the immune system, such as by the cellular or humoral arms of the human immune system. The term "antigen" includes antigenic determinants, such as peptides with lengths of 6, 7, 8, 9, 10, 11, 12, 13, 14, 15, 16, 17, 18, 19, 20, 21, 22 or more amino acid residues that bind to MHC molecules, form parts of MHC Class I or II complexes, or that are recognized when complexed with such molecules. In some embodiments, cells described herein have been primed with selected peptides that are known to be highly antigenic. In other embodiments, cells have been primed with a library of peptides, including commercially available overlapping peptides such as pepmixes. In some embodiments, As used herein an "antigen" is meant to refer to any substance that elicits an immune response.

An "antigen presenting cell (APC)" refers to a class of cells capable of presenting one or more antigens in the form of peptide-MHC complex recognizable by specific effector cells of the immune system, and thereby inducing an effective cellular immune response against the antigen or antigens being presented. Examples of professional APCs are dendritic cells and macrophages, though any cell expressing MHC Class I or II molecules can potentially present peptide antigen.

The term "autologous" as used herein refers to medical therapy in which the donor and recipient are the same person.

"Cord blood" has its normal meaning in the art and refers to blood that remains in the placenta and umbilical cord after birth and contains hematopoietic stem cells, cord blood may be fresh, cryopreserved or obtained from a cord blood bank.

The term "effector cell" describes cells that can bind to or otherwise recognize an antigen and mediate an immune response.

The term "isolated" means separated from components in which a material is ordinarily associated with, for example, an isolated lymphocytic cell can be separated from red blood cells, plasma, and other components of blood.

A "naïve" T-cell or other immune effector cell is one that has not been exposed to or primed by an antigen or to an antigen-presenting cell presenting a peptide antigen capable of activating that cell.

A "non-engineered cell" is a cell free of exogenous DNA or RNA.

A "peptide library" or "overlapping peptide library" is a complex mixture of peptides which in the aggregate covers the partial or complete sequence of a protein antigen, especially those of tumor associated antigens, viral associated tumor antigens, and opportunistic viruses. Successive peptides within the mixture overlap each other, for example, a peptide library may be constituted of peptides, for example but not limited to 15 amino acids in length which overlap adjacent peptides in the library by 11 amino acid residues and which span the entire length of a protein antigen. Peptide libraries are commercially available and may be custom-made for particular antigens. Methods for contacting, pulsing or loading antigen-presenting cells are well known and incorporated by reference to Ngo, et al (2014), Peptide libraries may be obtained from, for example, JPT and are incorporated by reference in their entireties from the website at https://www.jpt.com/products/peptrack/peptide-libraries. Peptide libraries may be used with the present invention, or alternatively, selected peptides that are known to be highly antigenic may be used with the present invention.

The term "precursor cell" refers to a cell which can differentiate or otherwise be transformed into a particular kind of cell. For example, a "T-cell precursor cell" can differentiate into a T-cell and a "dendritic precursor cell" can differentiate into a dendritic cell.

A "patient" is a vertebrate, preferably a mammal, more preferably a human. Mammals include, but are not limited to humans, simians, equines, bovines, porcines, canines, felines, murines, other farm animals, sport animals, or pets. Patients include those in need of tumor, virus, or other antigen-specific T-cells, such as those with lymphocytopenia, those who have undergone immune system ablation, those undergoing transplantation and/or immunosuppressive regimens, those having naïve or developing immune systems, such as neonates, or those undergoing cord blood or stem cell transplantation.

The term "pharmaceutically acceptable excipient, carrier or diluent" as used herein is meant to refer to an excipient, carrier or diluent that can be administered to a subject, together with an agent, and which does not destroy the pharmacological activity thereof and is nontoxic when administered in doses sufficient to deliver a therapeutic amount of the agent.

As used herein, "depleting" when referring to one or more particular cell type or cell population, refers to decreasing the number or percentage of the cell type or population, e.g., compared to the total number of cells in or volume of the composition, or relative to other cell types, such as by negative selection based on markers expressed by the population or cell, or by positive selection based on a marker not present on the cell population or cell to be depleted. The term does not require complete removal of the cell, cell type, or population from the composition.

As used herein, the terms "subject," "individual," "host," and "patient," are used interchangeably herein and refer to any mammalian subject for whom diagnosis, treatment, or therapy is desired, particularly humans. The methods described herein are applicable to both human therapy and veterinary applications. In some embodiments, the subject is a mammal, and in other embodiments the subject is a human.

As used herein, a "therapeutically effective amount" of a compound or composition or combination refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered.

The terms "treat," "treated," "treating," "treatment," and the like as used herein are meant to refer to reducing or ameliorating a disorder and/or symptoms associated therewith (e.g., a viral infection or a cancer). "Treating" may refer to administration of the cell compositions described herein to a subject after the onset, or suspected onset, of a viral infection or cancer. "Treating" includes the concepts of "alleviating", which refers to lessening the frequency of occurrence or recurrence, or the severity, of any symptoms or other ill effects related to cancer and/or the side effects associated with cancer or a viral infection. The term "treating" also encompasses the concept of "managing" which refers to reducing the severity of a particular disease or disorder in a patient or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

For any therapeutic agent described herein the therapeutically effective amount may be initially determined from preliminary in vitro studies and/or animal models. A therapeutically effective dose may also be determined from human data. The applied dose may be adjusted based on the relative bioavailability and potency of the administered agent. Adjusting the dose to achieve maximal efficacy based on the methods described above and other well-known methods is within the capabilities of the ordinarily skilled artisan. General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference in its entirety, are summarized below. Pharmacokinetic principles provide a basis for modifying a dosage regimen to obtain a desired degree of therapeutic efficacy with a minimum of unacceptable adverse effects. In situations where the drug's plasma concentration can be measured and related to the therapeutic window, additional guidance for dosage modification can be obtained. Drug products are considered to be pharmaceutical equivalents if they contain the same active ingredients and are identical in strength or concentration, dosage form, and route of administration. Two pharmaceutically equivalent drug products are considered to be bioequivalent when the rates and extents of bioavailability of the active ingredient in the two products are not significantly different under suitable test conditions.

As used herein, a statement that a cell or population of cells is "positive" for or "expresses" a particular marker refers to the detectable presence on or in the cell of a particular marker, typically a surface marker, for example a cluster of determination (CD) marker. When referring to a surface marker, the term refers to the presence of surface expression, for example, as detected by flow cytometry, for example, by staining with an antibody that specifically binds to the marker and detecting said antibody, wherein the staining is detectable by flow cytometry at a level substantially above the staining detected carrying out the same procedure with an isotype-matched control or fluorescence minus one (FMO) gating control under otherwise identical conditions and/or at a level substantially similar to that for cell known to be positive for the marker, and/or at a level substantially higher than that for a cell known to be negative for the marker.

The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters. "Identical" or "identity" as used herein in the context of two or more nucleic acids or amino acid sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may he performed manually or by using a computer sequence algorithm such as BLAST or BLAST 2.0. Briefly, the BLAST algorithm, which stands for Basic Local Alignment Search Tool is suitable for determining sequence similarity. Software for performing BLAST analyses is publicly available through the National Center for Biotechnology Information (http://www.ncbi.nlm.nih.gov). This algorithm involves first identifying high scoring sequence pair (HSPs) by identifying short words of length Win the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, less than about 0.1, less than about 0.01, and less than about 0.001. Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

As used herein, a statement that a cell or population of cells is "negative" for a particular marker refers to the absence of substantial detectable presence on or in the cell of a particular marker, typically a surface marker, for example a cluster of determination (CD) marker. When referring to a surface marker, the term refers to the absence of surface expression, for example, as detected by flow cytometry, for example, by staining with an antibody that specifically binds to the marker and detecting said antibody, wherein the staining is not detected by flow cytometry at a level substantially above the staining detected carrying out the same procedure with an isotype-matched control or fluorescence minus one (FMO) gating control under otherwise identical conditions, and/or at a level substantially lower than that for cell known to be positive for the marker, and/or at a level substantially similar as compared to that for a cell known to be negative for the marker.

Disclosed herein are ex vivo systems comprising a cell population disclosed herein and a column in fluid communication with the cell population, the column comprising one or a plurality of antibodies against CD3, CD4, CD8, CD56 or any combination of the aforementioned. CD markers. In some embodiments, the system comprises (i) an inlet in fluid communication with a reservoir of cells (e.g. a patient or a tissue culture dish) aligned with a column comprising antibodies against CD3, CD4, CD8, CD56 or any combination of the aforementioned; and an ex vivo collection vessel (e.g. a bag enclosing a sterile cavity) in fluid communication with column, such that cell populations disclosed herein are in the collection vessel. In some embodiments, the system further comprises a heating element capable of maintaining temperature of at least a portion of the system at 37 degrees Celsius. In some embodiments, the collection vessel, the column and the cell reservoir are a closed system such that the interior fluid channel among each component is sterile. In some embodiments, the collection vessel comprises one or a plurality of cell populations disclosed herein and one or a plurality of pharmaceutically acceptable carriers.

Cell Populations

The present invention provides isolated, non-engineered lymphocytic cell compositions for the treatment of cancer, including solid tumors and hematological malignancies, comprising a fixed ratio of multiple ex vivo primed and/or activated lymphocytic cell subsets directed to specific tumor associated antigens (TAAs), viral associated tumor antigens (VATA), glycolipids, or a combination thereof. The isolated cell compositions provided herein include fixed ratios of different lymphocytic cell subsets, wherein the different lymphocytic cell subsets within the cell composition are selected from a combination of $CD4^+$ T-cells, $CD8^+$ T-cells, $CD3^+/CD56^+$ Natural Killer T-cells ($CD3^+$ NKT-cells), TCR 76 T-cells, and or CD3-/$CD56^+$ Natural Killer Cells ($CD3^-$ NK cells).

$CD4^+$ T-Cells

The non-engineered cell compositions of the present invention include $CD4^+$ T-cells in ratios described herein. The $CD4^+$ T-cells are primed against one or more specific targets, for example one or more TAAs, VATAs, or a combination thereof.

$CD4^+$ T-cells are the primary orchestrators of the adaptive immune response, mediating a variety of cellular and humoral responses against pathogens and cancer. Although $CD4^+$ T-cells are thought to lack the capacity to directly kill or engulf pathogens, they are powerful activators of effector cells such as macrophages, cytotoxic T cells, and B cells. $CD4^+$ T-cells generally do not express or are negative for CD8, CD25, CD44, CD117, CD127, or TCR $\gamma/\delta$.

$CD4^+$ T-cells are crucial in achieving a regulated effective immune response to pathogens and tumors. Naive $CD4^+$ T-cells are activated after interaction with antigen-MHC complex and differentiate into specific subtypes depending mainly on the cytokine milieu of the microenvironment. Besides the classical T-helper 1 ($T_{h1}$) and T-helper 2 ($T_{h2}$), other $CD4^+$ T-cell subsets have been identified, including T-helper 17 ($T_{h17}$), regulatory T cell ($T_{reg}$), follicular helper T-cell ($T_{fh}$), and T-helper 9 ($T_{h9}$), each with a characteristic cytokine profile. For a particular phenotype to be differentiated, a set of cytokine signaling pathways coupled with activation of lineage-specific transcription factors and epigenetic modifications at appropriate genes are required. The effector functions of these cells are mediated by the cytokines secreted by the differentiated cells.

The $CD4^+$ T-cells included in the fixed ratios described herein are preferably of the T-helper 1 ($T_{h1}$)-type. $T_{h1}$ cells are involved with the elimination of intracellular pathogens and are associated with organ-specific autoimmunity (G. del Prete, "Human Th1 and Th2 lymphocytes: their role in the pathophysiology of atopy," Allergy, vol. 47, no. 5, pp. 450-455, 1992). They mainly secrete IFN-γ, lymphotoxin α (Lfα), and IL-2. IFN-γ is essential for the activation of mononuclear phagocytes, including macrophages, microglial cells, thereby resulting in enhanced phagocytic activity (H. W. Murray, B. Y. Rubin, and S. M. Carriero, "Human mononuclear phagocyte antiprotozoal mechanisms: Oxygen-dependent vs oxygen-independent activity against intracellular *Toxoplasma gondii*," Journal of Immunology, vol. 134, no. 3, pp. 1982-1988, 198). IFNγ is believed to exert its effect through the activation of IFNγ-responsive genes (U. Boehm, T. Klamp, M. Groot, and J. C. Howard, "Cellular responses to interferon-γ," Annual Review of Immunology, vol. 15, pp. 749-795, 1997). Cell markers typically associated with $CD4^+$ Th1-cells include CD3, CD4, CD119 (IFN-γ Rα), CD183 (CXCR3), CD195 (CCR5), CD218a (IL-18Rα), LT-βR, and CD366 (Tim-3).

Regulatory T cells ($T_{reg}$) are a subpopulation of $CD4^+$ T-cells that maintain homeostasis and tolerance within the immune system. $FOXP3^+CD25^+CD4^+$ regulatory T ($T_{reg}$) cells, which suppress aberrant immune response against self-antigens, also suppress anti-tumor immune responses. Infiltration of a large number of $T_{reg}$ cells into tumor tissues is often associated with poor prognosis. In some embodiments, the $CD4^+$ T-cells of the present invention are depleted of $T_{reg}$ cells. Various cell surface molecules, including chemokine receptors such as CCR4, that are specifically expressed by effector $T_{reg}$ cells can be targeted for the negative selection of $T_{regs}$ as provided herein. Cell markers typically associated with $CD4^+$ $T_{reg}$-cells include CD3, CD4, CD25 (IL-2Rα), CD39, CD73, CD103, CD152 (CTLA-4), GARP, GITR, and LAP (TGF-β).

$CD8^+$ T-Cells

The non-engineered cell compositions of the present invention include $CD8^+$ T-cells in ratios described herein. The $CD8^+$ T-cells are primed against one or more specific target antigens, for example one or more TAAs, VATAs, or a combination thereof.

$CD8^+$ T-cells are a subset of T-cells that express an αβ T-cell receptor (TCR) and are responsible for the direct killing of infected, damaged, and dysfunctional cells, including tumor cells. $CD8^+$ T cells, like $CD4^+$ Helper T cells, are generated in the thymus. However, rather than the CD4 molecule, cytotoxic T cells express a dimeric co-receptor—CD8—usually composed of one CD8α and one CD8β chain. $CD8^+$ T-cells recognize peptides presented by MHC Class I molecules, found on all nucleated cells. The CD8 heterodimer binds to a conserved portion (the α3 region) of MHC Class I during T cell/antigen presenting cell interactions.

$CD8^+$ T cells (often called cytotoxic T lymphocytes, or CTLs) are very important for immune defense against intracellular pathogens, including viruses and bacteria, and for tumor surveillance. When a $CD8^+$ T cell recognizes its antigen and becomes activated, it has three major mechanisms to kill infected or malignant cells. The first is secretion of cytokines, primarily TNF-α and IFN-γ, which have anti-tumor and anti-viral microbial effects.

The second major function is the production and release of cytotoxic granules. These granules, also found in NK cells, contain two families of proteins-perforin, and granzymes. Perforin forms a pore in the membrane of the target cell, similar to the membrane attack complex of complement. This pore allows the granzymes also contained in the cytotoxic granules to enter the infected or malignant cell. Granzymes are serine proteases which cleave the proteins inside the cell, shutting down the production of viral proteins and ultimately resulting in apoptosis of the target cell.

The cytotoxic granules are released only in the direction of the target cell, aligned along the immune synapse, to avoid non-specific bystander damage to healthy surrounding tissue. $CD8^+$ T-cells are able to release their granules, kill an infected cell, then move to a new target and kill again, often referred to as serial killing.

The third major function of $CD8^+$ T-cells is destruction of infected cells via Fas/FasL interactions. Activated $CD8^+$ T-cells express FasL on the cell surface, which binds to its receptor, Fas, on the surface of the target cell. This binding causes the Fas molecules on the surface of the target cell to trimerize, which pulls together signaling molecules. These signaling molecules result in the activation of the caspase cascade, which also results in apoptosis of the target cell. Because $CD8^+$ T-cells can express both molecules, Fas/FasL interactions are a mechanism by which $CD8^+$ T-cells can kill each other, called fratricide, to eliminate immune effector cells during the contraction phase at the end of an immune response.

IL-2 promotes proliferation of CD8+ T cells with acquisition of cytolytic phenotype (H. P. Kim, J. Imbert, and W. J. Leonard, "Both integrated and differential regulation of components of the IL-2/IL-2 receptor system," Cytokine and Growth Factor Reviews, vol. 17, no. 5, pp. 349-366, 2006; L. Gattinoni, C. A. Klebanoff, D. C. Palmer et al., "Acquisition of full effector function in vitro paradoxically impairs the in vivo antitumor efficacy of adoptively transferred $CD8^+$ T cells," Journal of Clinical Investigation, vol. 115, no. 6, pp. 1616-1626, 2005). Besides its role as T cell growth factor, IL-2 also promotes the development of CD8+ memory cells after antigen priming, and thus participating in ensuring a robust secondary immune response (M. A. Williams, A. J. Tyznik, and M. J. Bevan, "Interleukin-2 signals during priming are required for secondary expansion of CD8+ memory T cells," Nature, vol. 441, no. 7095, pp. 890-893, 2006).

Cell markers typically expressed by $CD8^+$ T-cells (or which $CD8^+$ T-cells are positive for) include $CD3^+$, $CD8^+$, and TCR $\alpha/\beta^+$, and which $CD8^+$ T-cells are negative for are CD25, CD44, CD117, CD127, and TCR γ/δ.

$CD3^+/CD56^+$ Natural Killer T-Cells ($CD3^+$ NKT-Cells)

In certain aspects of the present invention, the non-engineered cell compositions described herein include $CD3^+$ NKT-cells. The $CD3^+$ NKT-cells are activated. In certain embodiments, the $CD3^+$ NKT-cells can be primed against one or more specific glycolipid antigens, for example one or more gangliosides. In certain embodiments, the $CD3^+$ NKT-cells are exposed to one or more specific antigens. In certain embodiments, the $CD3^+$ NKT-cells are exposed to one or more specific antigens and cultured in the same culture as the αβ T-cells, $CD4^+$ T-cells, $CD8^+$ T-cells, and/or γδ T-cells, or combination thereof, wherein they are activated during culturing. In some embodiments, the $CD3^+$ NKT-cells are activated separately from other cells of the composition. In some embodiments, the CD3$^+$ NKT-cells are separately activated.

Natural killer T (NKT) cells are a specialized population of T cells that express a semi-invariant T cell receptor (TCR αβ) and surface antigens typically associated with natural killer cells. In humans, the TCRs of NKT cells almost always contain Vα24/Jα18 paired with a TCRs chain containing Vβ11. The TCR on NKT cells is unique in that it recognizes glycolipid antigens presented by the MHC I-like molecule CD1d. Most NKT cells, known as type I NKT cells, express an invariant TCR α-chain and one of a small number of TCR β-chains. The TCRs present on type I NKT cells is capable of recognizing the antigen α-galactosylceramide (α-GalCer). Within this group, distinguishable subpopulations have been identified, including CD4$^+$CD8$^-$ NKT-cells, CD4$^-$CD8$^-$ NKT-cells, and CD4$^-$CD8$^+$ T-cells.

NKT-cells also include a smaller population of NKT cells, known as type II NKT-cells (or noninvariant NKT-cells), which express a wider range of TCR α-chains, but do not recognize the α-GalCer antigen.

NKT-cells contribute to antibacterial and antiviral immune responses and promote tumor-related immunosurveillance or immunosuppression. Like natural killer cells, NKT-cells can also induce perforin-, Fas-, and TNF-related cytotoxicity. Activated NKT-cells are capable of producing IFN-γ and IL-4.

Cell markers typically expressed by NKT-cells (or which NKT-cells are positive for) include CD16, CD94, NKG2D, CD3, and CD56. NKT-cells generally do not express or are negative for CD14 and CD33.

αβ T-Cells

The non-engineered cell compositions of the present invention include αβ T-cells in ratios described herein. The αβ T-cells, which include CD4$^+$ and CD8$^+$ T-cells, are primed against one or more specific targets, for example one or more TAAs, VATAs, or a combination thereof.

There are two types of T-cell receptors: α/β and γ/δ. The dominant type is α/β which is associated with the two main T-cell populations: CD4$^+$ helper T cells and CD8$^+$ cytotoxic T cells. The αβ TCR can only recognize short linear peptides in association with molecules from the major histocompatability complex (MHC). Cells with the as TCR generally express CD4 or CD8 subset markers and mostly fall into helper or cytotoxic/effector subsets. Cell markers typically associated with αβ T-cells or which αβ T-cells are positive for include TCR α/β, CD2, CD3, CD7, CD16, CXCR4, NKG2D, and are TCR γδ−.

γδ T-Cells

In certain aspects of the present invention, the non-engineered cell compositions described herein include γδ T-cells. The γδ T-cells are activated. In certain embodiments, the γδ T-cells are exposed to one or more specific antigens. In certain embodiments, the γδ T-cells are exposed to one or more specific antigens and cultured in the same culture as the CD3$^+$ NKT-cells, CD4$^+$ T-cells, and/or CD8$^+$ T-cells, or combinations thereof, wherein they are activated during culturing. In some embodiments, the γδ T-cells are activated separately from other cells of the composition. In some embodiments, the γδ T-cells cells are separately activated.

γδ T-cells are a subset of T-cells defined by the genetic composition of their T Cell Receptor (TCR). γδ T-cells account for up to 10% of circulating lymphocytes and operate at the interface between innate and adaptive immunity. γδ T-cells recognize genomic, metabolic, and signaling perturbations associated with the transformed state. γδT-cells release perforin and granzymes, express both FAS and TRAIL, engage in Fc receptor-dependent effector functions and produce a range of immunomodulatory cytokines, including tumor necrosis factor (TNF) and interferon (IFN)-γ. γδ T-cells act as efficient antigen-presenting cells, enabling the perpetuation of immune attack through adaptive mechanisms. Finally, since these cells are not HLA-restricted, they do not elicit graft versus host disease.

Vγ9Vδ2 cells have endogenous cytotoxicity against various tumors; following activation, they can acquire phenotypic characteristics of professional antigen-presenting cells (γδ-APCs), including capacity for cross presentation of tumor-associated antigens. γδ T cells of the Vδ1 subtype have a naturally more naive memory ($T_{naive}$) phenotype, a reduced susceptibility to activation-induced cell death, and their natural residency in tissues.

Unlike ββ T-cells, most γδ T cells lack CD4 and CD8 and share a number of markers associated with natural killer cells or antigen-presenting cells such as Fc gamma RIII/CD16 and Toll-like receptors. Cell markers typically associated with γδ T-cells or which γδ T-cells are positive for include TCR γ/δ, CD2, CD3, CD7, CD16, CXCR4, and NKG2D. γδ T-cells do not express, or are negative, for TCR α/β.

CD3$^-$/CD56$^+$/CD16$^+$ NK Cells

CD3−/CD56+/CD16+ Natural Killer cells recognize and kill target cells in the absence of prior sensitization and are able to defend the host from infection or prevent the progression of a disease. NK cells are innate lymphoid cells (ILC) and contribute to innate immunity. Their activities are regulated through the biological modulation of a large array of both inhibitory and activating receptors, including killer cell immunoglobulin-like receptors (KIR), NKp44, and NKp46. These receptors do not bind specific antigens on target cells as do T cells, but rather molecules induced by cellular stress that provide an activating signal, or human leukocyte antigen (HLA) molecules that predominantly provide inhibitory signals.

NK cells do not express T-cell antigen receptors (TCR) or pan T marker CD3 or surface immunoglobulins (Ig) B cell receptors, but express the surface markers CD16 (FcγRIII) and CD56.

Monocytes

Monocytes are a type of leukocyte, and can differentiate into macrophages and myeloid lineage dendritic cells. Monocytes and their macrophage and dendritic-cell progeny serve three main functions in the immune system. These are phagocytosis, antigen presentation, and cytokine production. In vitro, monocytes can differentiate into dendritic cells by adding the cytokines granulocyte macrophage colony-stimulating factor (GM-CSF) and interleukin 4. Cell markers typically associated with monocytes include CD14, lack lineage markers for T cells, B cells, NK cells and DC cells, such as: NK1.1, CD90, CD45R and CD11c (see Geissmann F. et al. (2003). Blood Monocytes Consist of Two Principal Subsets with Distinct Migratory Properties. Immunity. 19:71-82).

Fixed Ratios of Different Lymphocytic Cell Subsets

The isolated cell compositions provided herein include fixed ratios of different non-engineered lymphocytic cell subsets, wherein the different lymphocytic cell subsets within the cell composition are selected from a combination of CD4$^+$ T-cells, CD8$^+$ T-cells, CD3$^+$/CD56$^+$ Natural Killer T-cells (CD3$^+$ NKT), and TCR γδ T-cells. In some embodiments, the cell compositions further comprise CD3$^-$ NK cells and/or CD14$^+$ monocytes. By providing a balanced ratio of multiple primed and/or activated immune effector cells with differing biological functions, long lasting and durable responses to multiple tumor-types are possible, increasing the ability of the administered cell composition to induce tumor specific-epitope spreading, and reducing tumor immune surveillance avoidance. Furthermore, by producing fixed ratios of primed and/or activated immune effector cells, consistent and reproducible homogeneous compositions are provided, reducing the variability of administered product received by different patients.

The ratios and percentages of cells as described herein are with reference to cell numbers. For example, a ratio of about 1:1:1 (+/−5-10%) provides for about an equal number of cells (+/−5-10%) from each identified cell subset contained in the cell composition.

CD4$^+$ T-Cell, CD8$^+$ T-Cell, and CD3$^+$ NKT-Cell Composition

In one aspect of the present invention, the composition provides a fixed ratio of a population of different non-engineered lymphocytic cell subsets comprising CD4$^+$ T-cells, CD8$^+$ T-cells, and CD3$^+$ NKT-cells exposed ex vivo to one or more specific target antigens. The CD4$^+$ T-cells and CD8$^+$ T-cells of the cell composition are primed against the one or more specific target antigens, while the CD3$^+$ NKT-cells are activated. In certain embodiments, the cells have been further exposed to one or more glycolipids, for example one or more gangliosides. In some embodiments, the CD3$^+$ NKT-cells are primed against one or more glycolipids, for example, a ganglioside.

In some embodiments, the composition comprises about a 1:1:1 ratio (+/−5-10%) of CD4$^+$ T-cells:CD8$^+$ T-cells: CD3$^+$ NKT-cells.

In some embodiments, the composition comprises between about 15% and 25% CD4$^+$ T-cells, between about 45% and 55% CD8$^+$ T-cells, and between about 25% and 35% CD3$^+$ NKT-cells. For example, in some embodiments, the composition comprises about 15%, 16%, 17%, 18%, 19%, 20%, 21%, 22%, 23%, 24%, or 25% CD4$^+$ T-cells; about 25%, 26%, 27%, 28%, 29%, 30%, 31%, 32%, 33%, 34%, or 35% CD8$^+$ T-cells; and about 45%, 46%, 47%, 48%, 49%, 50%, 51%, 52%, 53%, 54%, or 55% CD3$^+$ NKT-cells.

In some embodiments, the composition comprises about 20% CD4$^+$ T-cells, about 50% CD8$^+$ T-cells, and about 30% CD3$^+$ NKT-cells, resulting in a cell composition comprising about a 0.2:0.5:0.3 ratio of CD4$^+$ T-cells:CD8$^+$ T-cells:CD3$^+$ NKT-cells.

In an alternative embodiment, the cell composition comprises at least about 30% CD8$^+$ T-cells, at least about 15% CD4$^+$ T-cells, and at least about 10% CD3$^+$ NKT-cells. In some embodiments, the cell composition comprises between about 30% and 40% CD8$^+$ T-cells, about 15% to 25% CD4$^+$ T-cells, and from about 10% to about 20% CD3$^+$ NKT-cells. In some embodiments, the cell composition comprises about 35% CD8$^+$ T-cells, about 20% CD4$^+$ T-cells, and about 15% CD3$^+$ NKT-cells.

In an alternative embodiment, the cell composition comprises between about 30% and 40% CD8$^+$ T-cells, between about 5% and 15% CD4$^+$ T-cells, and between about 7.5% and 15% CD3$^+$ NKT-cells. In some embodiments, the composition comprises between at least about 30% CD8$^+$ T-cells, at least about 10% CD4$^+$ T-cells, and at least about 10% CD3$^+$ NKT-cells. In some embodiments, the composition comprises about 35% CD8$^+$ T-cells (+/−3-5%), about 10% CD4$^+$ T-cells (+/−3-5%), and about 10% CD3$^+$ NKT-cells (+/−3-5%). In some embodiments, the composition comprises CD8$^+$ T-cells, CD4$^+$ T-cells, and CD3$^+$ NKT-cells in about a 3.5:1:1 ratio (+/−5-10%).

In some embodiments, the CD4$^+$ T-cells of the composition are primarily CD4$^+$ $T_{h1}$-cells. For example, the CD4$^+$ $T_{h1}$-cells of the composition make up about 60%, 70%, 80%, or 90% of the total of CD4$^+$ T-cells in the composition.

In some embodiments, the composition is comprised of little or minimal CD4$^+$ $T_{reg}$-cells. For example, CD4$^+$ $T_{reg}$-cells make up less than 5%, 4%, 3%, 2%, or 1% of the population of CD4$^+$ T-cells.

The CD3$^+$ NKT-cells of the composition can be CD8$^+$, CD4$^+$, or CD8$^-$/CD4$^-$, or a mixture thereof. In some embodiments, the CDK3$^+$ NKT-cells are primarily type I NKT-cells. For example, in some embodiments, type I NKT-cells comprise about 60%, 70%, 80%, 90% or greater type I NKT-cells.

In some embodiments, the cell composition consists of only CD4$^+$ T-cells, CD8$^+$ T-cells, and CD3$^+$ NKT-cells.

In some embodiments, the cell composition comprises primarily CD4$^+$ T-cells, CD8$^+$ T-cells, and CD3$^+$ NKT-cells.

In some embodiments, the cells have been exposed to and/or primed against one or more targeted antigens selected from a TAA, a VATA, glycolipid, or a combination thereof. In some embodiments, the CD8$^+$ and CD4$^+$ T-cells can be primed to one or more specific antigens, for example one or more TAAs, and the CD3$^+$ NKT-cells are exposed to the same antigens. In some embodiments, the CD8$^+$ and CD4$^+$ T-cells can be primed to one or more specific antigens, for example one or more TAAs, and the CD3$^+$ NKT-cells are exposed to the same antigens, while all of the cells are further exposed to one or more glycolipids. In an alternative embodiment, the CD8$^+$ and CD4$^+$ T-cells can be primed to one or more specific antigens, for example one or more TAAs, and the CD3$^+$ NKT-cells are exposed to the same antigens, and the CD3$^+$ NKT-cells are further exposed and/or primed to one or more glycolipids. In some embodiments, the CD3$^+$ NKT-cells are further exposed and/or primed to one or more glycolipids.

In some embodiments, the lymphocytic cell subsets are naïve to one or more of the targeted antigens to which they are exposed. In some embodiments, the lymphocytic cell subsets are naïve to all of the targeted antigens to which they are exposed.

In some embodiments, the composition is comprised of little or minimal CD223$^+$ T-cells. For example, CD223$^+$ T-cells make up less than 5%, 4%, 3%, 2%, 1%, 0.5% or 0.1% of the population of T-cells.

TCR αβ T-Cell and TCR γδ T-Cell Composition

In an alternative aspect of the present invention, the composition provides a fixed ratio of a population of different non-engineered lymphocytic cell subsets comprising TCR αβ T-cells and TCR γδ T-cells. In some embodiments, the cells have been exposed ex vivo against one or more specific target antigens. In some embodiments, only the αβ T-cells are exposed to the one or more specific target antigens. The αβ T-cells of the cell composition are primed against the one or more specific target antigens, while the γδ T-cells are activated.

In some embodiments, the composition comprises about a 1:1 ratio (+/−5-10%) of αβ T-cells: γδ T-cells.

In some embodiments, the composition comprises between about 55% and 65% αβ T-cells and between about 35% and 45% γδ T-cells. For example, in some embodiments the composition comprises about 55%, 56%; 57%; 58%, 59%, 60%, 61%, 62%, 63%, 64%, or 65% αβ T-cells and about 35%, 36%, 37%, 38%, 39%, 40%, 41%, 42%, 43%, 44%, or 45% γδ T-cells.

In some embodiments, the composition comprises about 60% αβ T-cells and about 40% S T-cells.

In an alternative embodiment, the cell composition comprises at least about 40% αβ T-cells, and at least about 35%

γδ T-cells. In some embodiments, the composition comprises between about 35% and 45% αβ T-cells, and between about 30% and 40% S T-cells. In some embodiments, the composition comprises about 40% αβ T-cells and about 35% γδ T-cells.

The αβ T-cells of the composition may comprise varying ratios of $CD8^+$ and $CD4^+$ T-cells. For example, the αβ T-cells of the composition may comprise fixed ratios of $CD8^+$ and $CD4^+$ T-cells for example about a 1:1 ratio (+/−5-10%) of $CD8^+$ T-cells: $CD4^+$ T-cells; about 1.5:1 ratio (+/−5-10%) of $CD8^+$ T-cells: $CD4^+$ T-cells; about a 2:1 ratio (+/−5-10%) of $CD8^+$ T-cells: $CD4^+$ T-cells; about 2.5:1 ratio (+/−5-10%) of $CD8^+$ T-cells: $CD4^+$ T-cells; about 3:1 ratio (+/−5-10%) of $CD8^+$ T-cells: $CD4^+$ T-cells; about 3.5:1 ratio (+/−5-10%) of $CD8^+$ T-cells: $CD4^+$ T-cells; about 4:1 ratio (+/−5-10%) of $CD8^+$ T-cells: $CD4^+$ T-cells.

In some embodiments, the cell composition comprising αβ T-cells and γδ T-cells includes αβ T-cells that are between about 55% to about 65% of $CD8^+$ T-cells and between about 35% to about 45% of $CD4^+$ T-cells. For example, in some embodiments the composition comprises about 55%, 56; 57; 58%, 59%, 60%, 61%, 62%, 63%, 64%, or 65% $CD8^+$ T-cells and about 35%, 36%, 37%, 38%, 39%, 40%, 41%, 42%, 43%, 44%, or 45% $CD4^+$ T-cells.

In some embodiments, the cell composition comprising αβ T-cells and γδ T-cells includes αβ T-cells that are between about 60% $CD8^+$ T-cells and about 40% of $CD4^+$ T-cells.

In some embodiments, the $CD4^+$ T-cells of the composition are primarily $CD4^+$ Ti-cells. For example, the $CD4^+$ $T_{h1}$-cells of the composition make up about 60%, 70%, 80%, or 90% of the total $CD4^+$ T-cells in the composition.

In some embodiments, the composition is comprised of little or minimal $CD4^+$ $T_{reg}$-cells. For example, $CD4^+$ $T_{reg}$-cells make up less than about 5%, 4%, 3%, 2%, or 1% of the population of $CD4^+$ T-cells.

In some embodiments, the γδ T-cells are predominately Vγ9Vδ2 T-cells, for example, at least about 70%, 75%, 80%, 85%, 90% or more of the γδ T-cells are Vγ9Vδ2T-cells.

In some embodiments, the cell composition consists of only αβ T-cells and γδ T-cells.

In some embodiments, the cell composition comprises primarily αβ T-cells and γδ T-cells.

In some embodiments, the cells are exposed to one or more targeted antigens selected from a TAA, a VATA, or a combination thereof, and the αβ T-cells are primed against the same target antigens. In some embodiments, the lymphocytic cell subsets are naïve to one or more of the targeted antigens to which they are exposed. In some embodiments, the lymphocytic cell subsets are naïve to all of the targeted antigens to which they are exposed. In some embodiments, the γδ T-cells are activated by exposing them to zoledronic acid and IL-2.

In some embodiments, the composition is comprised of little or minimal $CD223^+$ T-cells. For example, $CD223^+$ T-cells make up less than 5%, 4%, 3%, 2%, 1%, 0.5% or 0.1% of the population of T-cells.

αβ T-Cells, γδ T-Cells, and $CD3^+$ NKT-Cells

In still other alternative aspects, the composition provides a fixed ratio of a population of different non-engineered lymphocytic cell subsets comprising αβ T-cells, γδ T-cells, and $CD3^+$ NKT-cells. In some embodiments, all of the cells are exposed to one or more specific target antigens. In some embodiments, only the αβ T-cells are exposed to one or more specific target antigens. The αβ T-cells of the cell composition are primed against the one or more specific target antigens, while the $CD3^+$ NKT-cells and γδ T-cells are activated.

In some embodiments, the composition comprises about a 1:1:1 ratio (+/−5-10%) of αβ T-cells: γδ T-cells: $CD3^+$ NKT-cells.

In some embodiments, the composition comprises between about 25% and 35% αβ T-cells, between about 25% and 35% γδ T-cells, and between about 35% and 45% $CD3^+$ NKT-cells. For example, in some embodiments the composition comprises about 25%, 26%, 27%, 28%, 29%, 30%, 31%, 32%, 33%, 34%, or 35% αβ T-cells; about 25%, 26%, 27%, 28%, 29%, 30%, 31%, 32%, 33%, 34%, or 35% γδ T-cells; and about 35%, 36%, 37%, 38%, 39%, 40%, 41%, 42%, 43%, 44%, or 45% of $CD3^+$ NKT-cells. In some embodiments, the composition consists of only αβ T-cells, γδ T-cells, and $CD3^+$ NKT-cells In some embodiments, the composition comprises about 30% αβ T-cells, about 30% S T-cells, and about 40% $CD3^+$ NKT-cells, resulting in a cell composition comprising about a 0.3:0.3:0.4 ratio of αβ T-cells: γδ T-cells: $CD3^+$ NKT-cells. In some embodiments, the αβ T-cells are comprised of a 1:1 ratio (+/−5-10%) of $CD4^+$ T-cells:$CD8^+$ T-cells, resulting in a cell composition comprising about a 0.15:0.15:0.3:0.4 ratio of $CD8^+$ T-cells: $CD4^+$ T-cells: γδ T-cells: $CD3^+$ NKT-cells.

In some embodiments, the αβ T-cells are comprised of between about 55% to about 65% of $CD8^+$ T-cells and between about 35% to about 45% of $CD4^+$ T-cells. For example, the composition is comprised of about 55%, 56%, 57%, 58%, 59%, 60%, 61%, 62%, 63%, 64%, or 65% $CD8^+$ T-cells, and about 35%, 365, 37%, 38%, 39%, 40%, 41%, 42%, 43%, 44%, or 45% $CD4^+$ T-cells.

In some embodiments, the αβ T-cells are comprised of about 60% $CD8^+$ T-cells and about 40% of $CD4^+$ T-cells, resulting in a cell composition comprising about a 0.18:0.12:0.3:0.4 ratio of $CD8^+$ T-cells: $CD4^+$ T-cells: γδ T-cells: $CD3^+$ NKT-cells.

The αβ T-cells of the composition may comprise varying ratios of $CD8^+$ and $CD4^+$ T-cells. For example, the αβ T-cells of the composition may comprise fixed ratios of $CD8^+$ and $CD4^+$ T-cells for example about a 1:1 ratio (+/−5-10%) of $CD8^+$ T-cells: $CD4^+$ T-cells; about 1.5:1 ratio (+/−5%) of $CD8^+$ T-cells: $CD4^+$ T-cells; about a 2:1 ratio (+/−5-10%) of $CD8^+$ T-cells: $CD4^+$ T-cells; about 2.5:1 ratio (+/−5-10%) of $CD8^+$ T-cells: $CD4^+$ T-cells; about 3:1 ratio (+/−5-10%) of $CD8^+$ T-cells: $CD4^+$ T-cells; about 3.5:1 ratio (+/−5-10%) of $CD8^+$ T-cells: $CD4^+$ T-cells; about 4:1 ratio (+/−5-10%) of $CD8^+$ T-cells: $CD4^+$ T-cells.

In some embodiments, the cell composition comprising αβ T-cells and γδ T-cells includes αβ T-cells that are between about 55% to about 65% of $CD8^+$ T-cells and between about 35% to about 45% of $CD4^+$ T-cells. For example, in some embodiments the composition comprises about 55%, 56%; 57%; 58%, 59%, 60%, 61%, 62%, 63%, 64%, or 65% $CD8^+$ T-cells and about 35%, 36%, 37%, 38%, 39%, 40%, 41%, 42%, 43%, 44%, or 45% $CD4^+$ T-cells.

In some embodiments, the cell composition comprising αβ T-cells and γδ T-cells includes αβ T-cells that are between about 60% $CD8^+$ T-cells and about 40% of $CD4^+$ T-cells, resulting in a cell composition comprising about a 0.6:0.4:1 ratio of $CD8^+$ T-cells: $CD4^+$ T-cells: γδ T-cells.

In an alternative embodiment, the cell composition comprises at least about 35% αβ T-cells, at least about 30% S T-cells, and at least about 10% $CD3^+$ NKT-cells. In some embodiments, the composition comprises between about 35% and 45% αβ T-cells, between about 30% and 40% S T-cells, and between about 10% and 20% $CD3^+$ NKT-cells. In some embodiments, the composition comprises about 40% αβ T-cells, about 35% γδ T-cells, and about 15% $CD3^+$ NKT-cells. In some embodiments, the αβ T-cells are comprised of a 1:1 ratio (+/−5-10%) of $CD8^+$ T-cells: $CD4^+$ T-cells. In some embodiments, the αβ T-cells are comprised of between about 55% to about 65% of $CD8^+$ T-cells and between about 35% to about 45% of $CD4^+$ T-cells. In some embodiments, the αβ T-cells are comprised of about 60% $CD8^+$ T-cells and about 40% of $CD4^+$ T-cells.

In some embodiments, the $CD4^+$ T-cells of the composition are primarily $CD4^+$ $T_{h1}$-cells. For example, the $CD4^+$ $T_{h1}$-cells of the composition make up about 60%, 70%, 80%, or 90% of the total $CD4^+$ T-cells in the composition.

In some embodiments, the composition is comprised of little or minimal $CD4^+$ $T_{reg}$-cells. For example, $CD4^+$ $T_{reg}$-cells make up less than 5%, 4%, 3%, 2%, or 1% of the population of $CD4^+$ T-cells.

In some embodiments, the γδ T-cells are predominately Vγ9Vδ2 T-cells, for example, at least about 70%, 75%, 80%, 85%, 90% or more of the γδ T-cells are Vγ9Vδ2T-cells.

The $CD3^+$ NKT-cells of the composition can be $CD8^+$ NKT-cells, $CD4^+$ NKT-cells, or $CD8^-/CD4^-$ NKT-cells, or a mixture thereof. In some embodiments, the CDK3+ NKT-cells are primarily type I NKT-cells. For example, in some embodiments, type I NKT-cells comprise about 60%, 70%, 80%, 90% or greater of the NKT-cells of the composition.

In some embodiments, the cell composition consists of only αβ T-cells, γδ T-cells, and $CD3^+$ NKT-cells.

In some embodiments, the cell composition consists of primarily αβ T-cells, γδ T-cells, and $CD3^+$ NKT-cells.

In some embodiments, the αβ T-cells can be primed to one or more specific antigens, for example one or more TAAs, and the $CD3^+$ NKT-cells and γδ T-cells are exposed to the same antigens. In some embodiments, the αβ T-cells can be primed to one or more specific antigens, for example one or more TAAs, and the $CD3^+$ NKT-cells and γδ T-cells are exposed to the same antigens, while all of the cells are further exposed to one or more glycolipids. In an alternative embodiment, the αβ T-cells can be primed to one or more specific antigens, for example one or more TAAs, the $CD3^+$ NKT-cells and γδ T-cells are exposed to the same antigens, and the $CD3^+$ NKT-cells are further exposed and/or primed to one or more glycolipids. In some embodiments, the $CD3^+$ NKT-cells are exposed and/or primed to one or more glycolipids. In some embodiments, the γδ T-cells are activated by exposing them to zoledronic acid and IL-2.

In some embodiments, the lymphocytic cell subsets are naïve to one or more of the targeted antigens to which they are exposed. In some embodiments, the lymphocytic cell subsets are naïve to all of the targeted antigens to which they are exposed.

In some embodiments, the composition is comprised of little or minimal $CD223^+$ T-cells. For example, $CD223^+$ T-cells make up less than about 5%, 4%, 3%, 2%, 1%, 0.5% or about 0.1% of the population of T-cells.

Exhaustion Markers

In one aspect of the invention, the cell compositions of the present invention may be further selected (or conditioned) for the presence or lack of one or more markers associated with, for example, maturation or exhaustion.

T cell exhaustion ($T_{ex}$) is a state of dysfunction that results from persistent antigen and inflammation, both of which commonly occur in cancer tissue. The reversal or prevention of exhaustion is a major area of research for cancer immunotherapy. $T_{ex}$ cell populations can be analyzed using multiple phenotypic parameters, either alone or in combination.

In one aspect, the cell composition in the fixed ratios described herein has less than 15% of cells expressing a marker associated with $T_{ex}$. In some embodiments, the cell compositions have less than 10% of cells expressing a marker associated with $T_{ex}$. In some embodiments, the cell composition has less than 5% of cells expressing a marker associated with $T_{ex}$. In some embodiments, the cell composition has less than about 5%, 4%, 3%, 2%, 1% or less of cells expressing a marker associated with $T_{ex}$.

Hallmarks commonly used to monitor T cell exhaustion are known in the art and include, but are not limited to, programmed cell death-1 (PD-1), CTLA-4/CD152 (Cytotoxic T-Lymphocyte Antigen 4), LAG-3 (Lymphocyte activation gene-3; CD223), TIM-3 (T cell immunoglobulin and mucin domain-3), 2B4/CD244/SLAMF4, CD160, and TIGIT (T cell Immunoreceptor with Ig and ITIM domains).

PD-1 (Programmed Death-1 receptor) is a key regulator of the threshold of immune response and peripheral immune tolerance. It is expressed on activated T cells, B cells, monocytes, and dendritic cells and binds to PD-L1 or PD-L2. PD-1 ligation induces co-inhibitory signals in T cells promoting their apoptosis, anergy, and functional exhaustion.

In one aspect of the invention, provided herein is a cell composition in the fixed ratios described herein, wherein the population has less than 15% of cells expressing PD-1. In some embodiments, the composition has less than 10% of cells expressing PD-1. In some embodiments, the composition of has less than 5% of cells expressing PD-1. In some embodiments, the composition has less than about 5%, 4%, 3%, 2%, 1% or less of cells expressing PD-1.

CTLA-4/CD152 (Cytotoxic T-Lymphocyte Antigen 4) is a transmembrane T cell inhibitory molecule that is expressed as a covalent homodimer. CTLA-4 is recruited from intracellular vesicles to the immunological synapse beginning 1-2 days after T cell activation. It forms a linear lattice with B7-1 on APC, inducing negative regulatory signals and ending CD28-dependent T cell activation. Mice deleted for CTLA-4 develop lethal autoimmune reactions due to continued T cell activation and poor control by regulatory T cells which constitutively express CTLA-4.

In one aspect of the invention, provided herein is a cell composition in the fixed ratios described herein wherein the population has less than 15% of cells expressing CTLA-4. In some embodiments, the composition has less than 10% of cells expressing CTLA-4. In some embodiments, the composition has less than 5% of cells expressing CTLA-4. In some embodiments, the composition has less than about 5%, 4%, 3%, 2%, 1% or less of cells expressing CTLA-4.

LAG-3 (Lymphocyte activation gene-3; CD223) is a transmembrane protein that binds to MHC class II molecules and negatively regulates T cell receptor signaling. It is expressed on activated T cells, NK cells, and plasmacytoid dendritic cells (pDC). LAG-3 limits the expansion of activated T cells and pDC in response to select stimuli. Proteolytic shedding of LAG-3 enables normal T cell activation by removing the negative regulation. Binding of a homodimerized soluble LAG-3/Ig fusion protein to MHC class II molecules induces maturation of immature DC as well as secretion of pro-inflammatory cytokines by cytotoxic $CD8^+$ T cells and NK cells.

In one aspect of the invention, provided herein is a cell composition in the fixed ratios described herein wherein the population of cells has less than 15% of cells expressing LAG-3. In some embodiments, the composition has less than 10% of cells expressing LAG-3. In some embodiments, the composition has less than 5% of cells expressing LAG-3.

In some embodiments, the composition has less than about 5%, 4%, 3%, 2%, 1% or less of cells expressing LAG-3.

TIM-3 (T cell immunoglobulin and mucin domain-3), also known as HAVCR2 is an immunosuppressive protein that enhances tolerance and inhibits anti-tumor immunity. It is upregulated on several populations of activated myeloid cells (macrophage, monocyte, dendritic cell, microglia, mast cell) and T cells (Th1, $CD8^+$, NK, Treg). TIM-3 ligation by Galectin-9 attenuates $CD8^+$ and Th1 cell responses and promotes the activity of Treg and myeloid derived suppressor cells. Dendritic cell-expressed TIM-3 dampens inflammation by enabling the phagocytosis of apoptotic cells and the cross-presentation of apoptotic cell antigens. TIM-3 also binds the alarmin HMGB1, thereby preventing the activation of TLRs in response to released tumor cell DNA.

In one aspect of the invention, provided herein is a cell composition in the fixed ratios described herein wherein the population s has less than 15% of cells expressing TIM-3. In some embodiments, the composition has less than 10% of cells expressing TIM-3. In some embodiments, the composition has less than 5% of cells expressing TIM-3. In some embodiments, the composition has less than about 5%, 4%, 3%, 2%, 1% or less of cells expressing TIM-3.

2B4, also known as CD244, is a cell surface glycoprotein belonging to the CD2 subgroup of the immunoglobulin superfamily. It acts as a high-affinity receptor for CD48. It is expressed by natural killer (NK) cells and $CD8^+$ T cell subsets. It can regulate killing by $CD8^+$ T cells and NK cells, and IFN-gamma secretion by NK cells. It may also regulate NK cell and T cell proliferation.

In one aspect of the invention, provided herein is a cell composition in the fixed ratios described herein, wherein the population has less than 15% of cells expressing 2B4. In some embodiments, the composition has less than 10% of cells expressing 2B4. In some embodiments, the composition has less than 5% of cells expressing 2B4. In some embodiments, the composition has less than about 5%, 4%, 3%, 2%, 1% or less of cells expressing 2B4.

CD160 is a GPI-anchored glycoprotein with one Ig-like V-type domain. On a subpopulation of cytolytic T cells and NK cells, CD160 functions as a broad specificity receptor for MHC class I and related molecules. When expressed on vascular endothelial cells, CD160 propagates anti-angiogenic signals and promotes apoptosis.

In one aspect of the invention, provided herein is a cell composition in the fixed ratios described herein, wherein the cell population has less than 15% of cells expressing CD160. In some embodiments, the composition has less than 10% of cells expressing CD160. In some embodiments, the composition has less than 5% of cells expressing CD160. In some embodiments, the composition has less than about 5%, 4%, 3%, 2%, 1% or less of cells expressing CD160.

TIGIT (T cell Immunoreceptor with Ig and ITIM domains), also called Vstm3, Vsig9, and WUCAM, is a transmembrane protein in the CD28 family of the Ig superfamily proteins. TIGIT is expressed on NK cells and subsets of activated, memory and regulatory T cells, and particularly on follicular helper T cells within secondary lymphoid organs. It binds to CD155/PVR/Necl-5 and Nectin-2/CD112/PVRL2 on dendritic cells (DC) and endothelium. Binding of TIGIT by DC induces IL-10 release and inhibits IL-12 production. Ligation of TIGIT on T cells downregulates TCR-mediated activation and subsequent proliferation, while NK cell TIGIT ligation blocks NK cell cytotoxicity. CD155 and Nectin-2 also interact with DNAM-1/CD226 and CD96/Tactile, and TIGIT binding to CD155 can antagonize the effects of DNAM-1. Soluble TIGIT is able to compete with DNAM-1 for CD155 binding and attenuates T cell responses, while mice lacking TIGIT show increased T cell responses and susceptibility to autoimmune challenges.

In one aspect of the invention, provided herein is a cell composition in the fixed ratios described herein, wherein the population has less than 15% of cells expressing TIGIT. In some embodiments, the composition has less than 10% of cells expressing TIGIT. In some embodiments, the composition has less than 5% of cells expressing TIGIT. In some embodiments, the composition has less than about 5%, 4%, 3%, 2%, 1% or less of cells expressing TIGIT.

In one aspect of the invention, provided herein is a cell composition in a fixed ratio as described herein, wherein the cell population has less than 15% of cells expressing a marker associated with $T_{ex}$. In some embodiments, the composition has less than 10% of cells expressing a marker associated with $T_{ex}$. In some embodiments, the composition has less than 5% of cells expressing a marker associated with $T_{ex}$. In some embodiments, the composition has less than about 5%, 4%, 3%, 2%, 1% or less of cells expressing a marker associated with $T_{ex}$. In some embodiments, the $T_{ex}$ marker is PD-1. In some embodiments, the $T_{ex}$ marking is CTLA-4. In some embodiments, the $T_{ex}$ marker is TIM3. In some embodiments, the $T_{ex}$ is Lag3. In some embodiments, the $T_{ex}$ is 2B4. In some embodiments, the $T_{ex}$ is CD160. In some embodiments, the $T_{ex}$ is TIGIT. In some embodiments, the composition comprises less than 10% of TAA-Ls expressing one of PD-1, CTLA-4, TIM3, LAG3, 2B4, CD160, TIGIT, or a combination thereof. In some embodiments, the composition comprises less than 5% of TAA-Ls expressing one of PD-1, CTLA-4, TIM3, LAG3, 2B4, CD160, TIGIT, or a combination thereof. In some embodiments, the composition comprises less than about 5%, 4%, 3%, 2%, 1% or less of the cell population expressing one of PD-1, CTLA-4, TIM3, LAG3, 2B4, CD160, TIGIT, or a combination thereof.

Methods for identifying cells having these particular markers are well known in the art.

Targeted Antigens

The present invention provides isolated cell compositions for the treatment of abnormal cell proliferation such as cancer, including hematological and solid tumors, comprising a selected, fixed ratio of multiple ex vivo activated lymphocytic cell subsets, including specific immune effector cells directed to specific tumor associated antigens (TAAs), viral associated tumor antigens (VATA), glycolipids, or a combination thereof.

The different lymphocytic cell subsets within the cell composition are selected from a combination of activated $CD4^+$ T-cells, $CD8^+$ T-cells, $CD3^+/CD16^+/CD56^+$ Natural Killer T-cells ($CD3^+$ NKT), and TCR γδ T-cells (γδ T-cells). In some embodiments, the composition may further comprise $CD3^-$ NK cells and/or $CD14^+$ monocytes. In particular, the cell population includes $CD4^+$ T-cells and $CD8^+$ T-cells that have been primed and capable of targeting one or more specific antigens for tumor killing and/or cross presentation. The cell composition further comprises activated γδ T-cells and/or activated $CD3^+$ NKT cells capable of mediating anti-tumor responses.

The cell composition can include cells primed to or exposed to one or more tumor antigens.

Tumor Associated Antigens

Tumor associated antigens can be loosely categorized as oncofetal (typically only expressed in fetal tissues and in cancerous somatic cells), oncoviral (encoded by tumorigenic transforming viruses), overexpressed/accumulated (expressed by both normal and neoplastic tissue, with the level of expression highly elevated in neoplasia), cancer-testis (expressed only by cancer cells and adult reproductive tissues such as testis and placenta), lineage-restricted (expressed largely by a single cancer histotype), mutated (only expressed by cancer as a result of genetic mutation or alteration in transcription), post-translationally altered (tumor-associated alterations in glycosylation, etc.), or idiotypic (highly polymorphic genes where a tumor cell expresses a specific "clonotype", i.e., as in B cell, T cell lymphoma/leukemia resulting from clonal aberrancies).

Examples of oncofetal tumor associated antigens include Carcinoembryonic antigen (CEA), immature laminin receptor, and tumor-associated glycoprotein (TAG) 72. Examples of overexpressed/accumulated include BING-4, calcium-activated chloride channel (CLCA) 2, Cyclin B1, 9D7, epithelial cell adhesion molecule (Ep-Cam), EphA3, Her2/neu, telomerase, mesothelin, stomach cancer-associated protein tyrosine phosphatase 1 (SAP-1), and survivin.

Examples of cancer-testis antigens include the b melanoma antigen (BAGE) family, cancer-associated gene (CAGE) family, G antigen (GAGE) family, melanoma antigen (MAGE) family, sarcoma antigen (SAGE) family and X antigen (XAGE) family, CT9, CT10, NY-ESO-1, L antigen (LAGE) 1, Melanoma antigen preferentially expressed in tumors (PRAME), and synovial sarcoma X (SSX) 2. Examples of lineage restricted tumor antigens include melanoma antigen recognized by T cells-1/2 (Melan-A/MART-1/2), Gp100/pmel17, tyrosine-related protein (TRP) 1 and 2, P.polypeptide, melanocortin 1 receptor (MCR), and prostate-specific antigen. Examples of mutated tumor antigens include β-catenin, breast cancer antigen (BRCA) 1/2, cyclin-dependent kinase (CDK) 4, chronic myelogenous leukemia antigen (CML) 66, fibronectin, p53, Ras, and TGF-βRII. An example of a post-translationally altered tumor antigen is mucin (MUC) 1. Examples of idiotypic tumor antigens include immunoglobulin (Ig) and Tcell receptor (TCR). In some embodiments, the cell populations are stimulated with a combination of PRAME, WT1 and Survivin. In some embodiments, the cell populations are stimulated with an amino acid or nucleic acid sequence encoding an amino acid sequence comprising at least about 75%, 80%, 85%, 90%, 95%, 96%, 97%, 98%, 99% or 100% sequence identity to human PRAME (SEQ ID NO:1):

```
MERRRLRGSIQSRYISMSVWTSPRRLVELAGQSLLKDEALAIAALELLPR

ELEPPLFMAAFDGRHSQTLKAMVQAWPFTCLPLGVLMKGQHLHLETFKAV

LDGLDVLLAQEVRPRRWKLQVLDLRKNSHQDFWTVWSGNRASLYSFPEPE

AAQPMTKKRKVDGLSTEAEQPFIPVEVLVDLFLKEGACDELFSYLIEKVK

RKKNVLRLCCKKLKIFAMPMQDIKMILKMVQLDSIEDLEVTCTWKLPTLA

KESPYLGQMINLRRLLLSHIHASSYISPEKEEQYIAQFTSQFLSLQCLQA

LYVDSLEFLRGRLDQLLRHVMNPLETLSITNCRLSEGDVMHLSQSPSVSQ

LSVLSLSGVMLTDVSPEPLQALLERASATLQDLVEDECGITDDQLLALLP

SLSHCSQLTTLSFYGNSISISALQSLLQHLIGLSNLTHVLYPVPLESYED

IHGTLHLERLAYLHARLRELLCELGRPSMVWLSANPCPHCGDRTFYDPEP

ILCPCFMPN
```

In some embodiments, the cell populations are stimulated with an amino acid or nucleic acid sequence encoding an amino acid sequence comprising at least about 75%, 80%, 85%, 90%, 95%, 96%, 97%, 98%, 99% or 100% a sequence identity to human survivin (SEQ ID NO:2):

```
MGAPTLPPAWQPFLKDHRISTFKNWPFLEGCACTPERMAEAGFIHCPTEN

EPDLAQWVFCFKELEGWEPDDDPIEEHKKHSSGCAFLSVKKQFEELTLGE

FLKLVRETLPPPRSFIR
```

In some embodiments, the cell populations are stimulated with an amino acid or nucleic acid sequence encoding an amino acid sequence comprising at least about 75%, 80%, 85%, 90%, 95%, 96%, 97%, 98%, 99% or 100% a sequence identity to human WT1 (SEQ ID NO:3):

```
MGSDVRDLNALLPAVPSLGGGGGCALPVSGAAQWAPVLDFAPPGASAYGS

LGGPAPPPAPPPPPPPPPHSFIKQEPSWGGAEPHEEQCLSAFTVHFSGQF

TGTAGACRYGPFGPPPPSQASSGQARMFPNAPYLPSCLESQPAIRNQGYS

TVTFDGTPSYGHTPSHHAAQFPNHSFKHEDPMGQQGSLGEQQYSVPPPVY

GCHTPTDSCTGSQALLLRTPYSSDNLYQMTSQLECMTWNQMNLGATLKGV

AAGSSSSVKWTEGQSNHSTGYESDNHTTPILCGAQYRIHTHGVFRGIQDV

RRVPGVAPTLVRSASETSEKRPFMCAYPGCNKRYFKLSHLQMHSRKHTGE

KPYQCDFKDCERRFSRSDQLKRHQRRHTGVKPFQCKTCQRKFSRSDHLKT

HTRTHTGKTSEKPFSCRWPSCQKKFARSDELVRHHNMHQRNMTKLQLAL
```

In some embodiments, the antigen associated with the disease or disorder is selected from the group consisting of orphan tyrosine kinase receptor ROR1, tEGFR, L1-CAM, CD19, CD20, CD22, hepatitis B surface antigen, anti-folate receptor, CD23, CD24, CD30, CD33, CD38, CD44, EGFR, EGP-2, EGP-4, OEPHa2, ErbB2, 3, or 4, FBP, fetal acetylcholine receptor, HMW-MAA, IL-22R-alpha, IL-13R-alpha2, kdr, kappa light chain, Lewis Y, L-cell adhesion molecule, MAGE-A1, MUC1, MUC16, PSCA, NKG2D Ligands, oncofetal antigen, VEGF-R2, PSMA, estrogen receptor, progesterone receptor, ephrinB2, CD123, CS-1, c-Met, GD-2, and MAGE A3 and/or biotinylated molecules, and/or molecules expressed by HIV, HCV, HBV or other pathogens.

Exemplary tumor antigens include at least the following: carcinoembryonic antigen (CEA) for bowel cancers; CA-125 for ovarian cancer; MUC-1 or epithelial tumor antigen (ETA) or CA15-3 for breast cancer; tyrosinase or melanoma-associated antigen (MAGE) for malignant melanoma; and abnormal products of ras, p53 for a variety of types of tumors; alpha-fetoprotein for hepatoma, ovarian, or testicular cancer; beta subunit of hCG for men with testicular cancer; prostate specific antigen for prostate cancer; beta 2 microglobulin for multiple myeloma and in some lymphomas; CA19-9 for colorectal, bile duct, and pancreatic cancer; chromogranin A for lung and prostate cancer; TA90 for melanoma, soft tissue sarcomas, and breast, colon, and lung cancer. Examples of tumor antigens are known in the art, for example in Cheever et al., 2009, which is incorporated by reference herein in its entirety.

Specific examples of tumor antigens include at least MHC, CTLA-4, PD-L1, CD40, EGFP, Her2, TCR alpha, cdr2, 4-1BB, CT26, GITR, OX40, TGF-β. WT1, LMP2, HPV E6 E7, EGFRvII, HER-2/neu, p53 nonmutant, Ras mutant, p53 mutant, Proteinase3 (PR1), bcr-abl, Survivin, PSA, hTERT, EphA2, PAP, ML-IAP, AFP, EpCAM, ERG (TMPRSS2 ETS fusion gene), NA17, PAX3, ALK, Androgen receptor, Polysialic acid, MYCN, RhoC, TRP-2, sLe(a), CYPiB1, PLAC1, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, XAGE 1, B7H3, Legumain, Tie 2, Page4, MAD-CT-1, FAP, PDGFR-β, MAD-CT-2, Fos-related antigen 1, IL13Rα2 (Interleukin-13Ra2), GPC3 (Glypican-3), CAIX (Carbonic anhydrase IX), CD133 (Cluster of differentiation 133 (also known as prominin-1)), FAP (Fibroblast activation protein), B-cell maturation antigen (BCMA), X box Protein 1 (XBP1), CS1, and CD138 (Syndecan-1), and FR-α (Folate receptor-α).

Viral Associated Tumor Antigens

Examples of oncoviral tumor-associated antigens include human papilloma virus (HPV) L1, E6 and E7, Epstein-Barr Virus (EBV) Epstein-Barr nuclear antigen (EBNA), EBV viral capsid antigen (VCA) Igm or IgG, EBV early antigen (EA), latent membrane protein (LMP) 1 and 2, hepatitis B surface antigen (HBsAg), hepatitis B e antigen (HBeAg), hepatitis B core antigen (HBcAg), hepatitis B x antigen (HBxAg), hepatitis C core antigen (HCV core Ag), Human T-Lymphotropic Virus Type 1 core antigen (HTLV-1 core antigen), HTLV-1 Tax antigen, HTLV-1 Group specific (Gag) antigens, HTLV-1 envelope (Env), HTLV-1 protease antigens (Pro), HTLV-1 Tof, HTLV-1 Rof, HTLV-1 polymerase (Pro) antigen, Human T-Lymphotropic Virus Type 2 core antigen (HTLV-2 core antigen), HTLV-2 Tax antigen, HTLV-2 Group specific (Gag) antigens, HTLV-2 envelope (Env), HTLV-2 protease antigens (Pro), HTLV-2 Tof, HTLV-2 Rof, HTLV-2 polymerase (Pro) antigen, latency-associated nuclear antigen (LANA), human herpesvirus-8 (HHV-8) K8.1, Merkel cell polyomavirus large T antigen (LTAg), and Merkel cell polyomavirus small T antigen (sTAg).

Glycolipids

Elevated expression of certain types of glycolipids, for example gangliosides, is associated with the promotion of tumor survival in certain types of cancers. Examples of gangliosides include, for example, GM1b, GD1c, GM3, GM2, GM1a, GD1a, GT1a, GD3, GD2, GD1b, GT1b, GQ1b, GT3, GT2, GT1c, GQ1c, and GP1c. Examples of ganglioside derivatives include, for example, 9-O-Ac-GD3, 9-O-Ac-GD2, 5-N-de-GM3, N-glycolyl GM3, NeuGcGM3, and fucosyl-GM1. Exemplary gangliosides that are often present in higher levels in tumors, for example melanoma, small-cell lung cancer, sarcoma, and neuroblastoma, include GD3, GM2, and GD2. In some embodiments, the CD3+ NKT-cells of the compositions are activated using a ganglioside, for example, but not limited, to GD3, GM2, and GD2.

Targeted Disorders

The isolated, non-engineered cell composition as described herein can be administered in an effective amount to a patient that has an abnormal cellular proliferation disorder or disease, including, but not limited to, cancer such as a hematological malignancy or solid tumor.

In certain embodiments, the disorder treated is a hematological malignancy, for example but not limited to T-cell or NK-cell lymphoma, for example, but not limited to: peripheral T-cell lymphoma; anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous $CD30^+$ T-cell lymphoproliferative disorder; primary cutaneous aggressive epidermotropic $CD8^+$ cytotoxic T-cell lymphoma; primary cutaneous gamma-delta T-cell lymphoma; primary cutaneous small/medium $CD4^+$ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic $EBV^+$ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In certain embodiments, the hematological malignancy is a lymphoma or lymphocytic or myelocytic proliferation disorder or abnormality. For example, the methods as described herein can be administered to a host suffering from a Hodgkin Lymphoma or a Non-Hodgkin Lymphoma. For example, the host can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, the methods described herein can be used to treat a subject, for example a human, with a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

Alternatively, the methods described herein, can be used to treat a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus $(EBV)^+$ DLBCL of the elderly; Primary mediastinal (thymic) large B-cell lymphoma; Primary cutaneous DLBCL, leg type; $ALK^{+}$ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In some embodiments, the methods described herein can be used to treat a leukemia. For example, the subject may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); large granular lymphocytic leukemia; or Adult T-cell chronic leukemia. In some embodiments, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

Alternatively, the cancer that can be treated according to the present invention include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast, triple negative breast cancer, HER2-negative breast cancer, HER2-positive breast cancer, male breast cancer, late-line metastatic breast cancer, progesterone receptor-negative breast cancer, progesterone receptor-positive breast cancer, recurrent breast cancer), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic adenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Cell Composition Manufacture

The cell compositions of fixed ratio lymphocytic cell substypes described herein can be generated by any method known in the art. As described above, the cell compositions include as T-cells, for example $CD4^{+}$ and $CD8^{+}$ T-cells, that have been primed against one or more specific antigens. $\alpha\beta$ T-cells that recognize at least one epitope of an antigen of a cancer can be generated by any method known in the art or as described herein. Non-limiting exemplary methods of generating $\alpha\beta$ T-cells that recognize at least one epitope of an antigen of a cancer can be found in Shafer et al., Leuk Lymphoma (2010) 51(5):870-880; Cruz et al., Clin Cancer Res., (2011) 17(22): 7058-7066; Quintarelli et al., Blood (2011) 117(12): 3353-3362; Chapuis et al., Sci Transl Med (2013) 5(174):174ra27; and US 2017/0037369, all incorporated herein by reference.

As described herein, the $\gamma\delta$ T-cells and/or $CD3^{+}$ NKT-cells of the cell composition are activated. In some embodiments of the invention, the $\gamma\delta$ T-cells and/or $CD3^{+}$ NKT-cells are exposed to one or more specific antigens. In some embodiments, the S T-cells and/or $CD3^{+}$ NKT-cells are cultured alongside of the $\alpha\beta$ T-cells and become activated during the manufacturing process, for example, as described herein. In some embodiments, the 6S T-cells and/or $CD3^{+}$ NKT-cells can be separated from the $\alpha\beta$ T-cells via a selection method and expanded and activated. Methods for expanding and activation $CD3^{+}$ NKT-cells are known in the art, for example, as described in e.g., East et al., Artificial Antigen Presenting Cell (aAPC) Mediated Activation and Expansion of Natural Killer T Cells, J Vis Exp. 2012; (70): 4333; Webb et al., E vivo induction and expansion of natural killer T cells by CD1d1-Ig coated artificial antigen presenting cells, J Immunol Methods. 2009 Jul. 31; 346(1-2):38-44; Osada et al., & vivo expanded human $CD4^{+}$ regulatory NKT cells suppress expansion of tumor antigen-specific CTLs, International Immunology, Volume 17, Issue 9, 1 Sep. 2005, Pages 1143-1155; and Fernandez et al., &-vivo $\alpha$-Galactosylceramide activation of NKT cells in humans and macaques, J. Imm. Methods 382 (2012):150-159, all incorporated herein by reference. Methods for expansion and activation of $\gamma\delta$ T-cells are known in the art, for example, as described in WO2016/087871; Kondo et al., Zoledronate facilitates large-scale ex vivo expansion of functional gamma delta T cells from cancer patients for use in adoptive immunotherapy, Cytotherapy. 2008; 10(8):842-56; and Nichol et al., Clinical evaluation of autologous gamma delta T cell-based immunotherapy for metastatic solid tumors, British Journal of Cancer volume 105, pages 778-786 (6 Sep. 2011), all incorporated herein by reference. In some embodiments, the $CD3^+$ NKT-cells are exposed to a ganglioside. In some embodiments, the γδ T-cells are activated using zoledronic acid and IL-2.

The cell composition can be manufactured, for example, by (i) collecting a mononuclear cell product, for example an allogeneic sample from a donor or cord-blood or an autologous sample from a patient; (ii) separating the monocytes and the lymphocytes of the mononuclear cell product; (iii) generating and maturing dendritic cells (DCs) from the monocytes; (iv) pulsing the DCs with one or more tumor antigens; (v) optionally carrying out a $CD45RA^+$ selection to isolate naïve lymphocytes; (vi) stimulating the naïve lymphocytes with the peptide-pulsed DCs in the presence of a cytokine cocktail; (vii) repeating the T cell stimulation with fresh peptide-pulsed DCs or other peptide-pulsed antigen presenting cells in the presence of a cytokine cocktail; (viii) harvesting the cells; (ix) subjecting the cells to a selection protocol which isolates the desired specific lymphocytic cell subsets into discrete populations; (x) optionally further expanding one or more of the discrete lymphocytic cell subset populations to derive sufficient numbers to arrive at a fixed ratio described herein suitable for administration at a total cell population described herein; (xi) recombining the discrete cell populations to provide a cell composition at the fixed ratios described herein, or in an alternative embodiment, optionally keeping the discrete lymphocytic cell subsets separate wherein the population is suitable for inclusion in a kit suitable for administration to a patient, wherein each discrete lymphocytic cell subset is at a cell population corresponding to a cell composition fixed ratio described herein collectively; and (xii) optionally cryopreserving for future use.

Methods for separating mixed cell populations into discrete cell subtypes are well known in the art. For example, affinity column chromatography can be utilized to positively select desired cells by their interaction with the column media. For examples of prior positive selections by column chromatography see: Godfrey, H. P., & Gell, P. G. (1976). Separation by column chromatography of cells active in delayed-onset hypersensitivities. Immunology, 30(5), 695-703 and Xiao F. et al. (2005) Cell column chromatography: a new research tool to quantify cerebral cell volume changes following chemically-induced anoxia/re-oxygenation; in Intracranial Pressure and Brain Monitoring XII. Acta Neurochirurgica Supplementum, vol 95. Springer, Vienna; all incorporated herein by reference.

Enzymatic techniques for isolating cell populations are also useful and widely known. For examples of prior enzymatic positive selections see: Sugita, N. et. al., (2016). Optimization of human mesenchymal stem cell isolation from synovial membrane: Implications for subsequent tissue engineering effectiveness. Regenerative Therapy, 5, 79-85; incorporated herein by reference.

The cell population may also be separated by cell sorting. For a review of cell sorting and various other techniques see Syverud B C, Lee J D, VanDusen K W, et al. (2014) Isolation and purification of satellite cells for skeletal muscle tissue engineering. J Regen Med. 3(2), incorporated herein by reference. In some embodiments the cells are sorted by flow cytometry. Non-limiting examples of instruments to achieve flow cytometry include fluorescence activated cell sorters and automacs seperators with or without detection techniques associate with their use.

HLA Matching

In certain aspects of the present invention, the non-engineered cell composition to be administered to the patient is derived from an allogeneic sample, for example a donor sample or cord-blood sample. In some embodiments, the allogeneic sample is not derived from a patient's previous stem cell transplant donor. In such cases, it is important that the cell composition be compatible with the recipient patient, e.g., that human leukocyte antigen (HLA) allelic profile of the cells of the composition, most notably the $CD4^+$ T-cells and $CD8^+$ T-cells, are compatible with the HLA allelic profile of the recipient patient.

There are 7,196 HLA alleles. These are divided into 6 HLA class I and 6 HLA class II alleles for each individual (on two chromosomes). The HLA system or complex is a gene complex encoding the major histocompatibility complex (MHC) proteins in humans. HLAs corresponding to MHC Class I (A, B, or C) present peptides from within the cell and activate $CD8^+$ T-cells. HLAs corresponding to MHC Class II (DP, DM, DOA, DOB, DQ and DR) stimulate the multiplication of $CD4^+$ T-cells) which stimulate antibody-producing B-cells.

Determining HLA subtype (i.e., typing the HLA loci) can be performed by any method known in the art. Non-limiting exemplary methods for determining HLA subtype can be found in Lange, V., et al., BMC Genomics (2014)15:63; Erlich, H., Tissue Antigens (2012) 80:1-11; Bontadini, A., Methods (2012) 56:471-476; Dunn, P. P., Int J Immunogenet (2011) 38:463-473; and Hurley, C. K., "DNA-based typing of HLA for transplantation." in Leffell, M. S., et al., eds., Handbook of Human Immunology, 1997. Boca Raton: CRC Press. In some embodiments, the cell composition and recipient match one or more HLA loci. In some embodiments, the cell composition and recipient match at least 4 HLA loci, preferably HLA-A, HLA-B, HLA-C, and HLA-DRB1. In some embodiments, the cell composition and recipient match at least 6 HLA loci. In some embodiments, the cell composition and recipient match at least 8 HLA loci. In some embodiments, the step of determining HLA subtype comprises typing 8 HLA loci.

Banking

In one aspect, the invention further includes a bank or library, and methods of manufacturing a bank or library of individual non-engineered lymphocytic subsets. In some embodiments, the bank includes individual $CD8^+$ and $CD4^+$ T-cell subpopulations which have been primed and activated to one or more specific TAAs, VATAs, or combination thereof. In addition, in some embodiments, the bank includes individual $CD3^+$ NKT-cells and/or γδT-cells, and or $CD3^-$ NK cells that have been activated. The lymphocytic cell subsets can be maintained as separate aliquots in the bank and combined prior to administration, or administered to the patient as separate aliquots. Alternatively, the lymphocytic cell subsets can be recombined in a fixed ratio described herein and cryopreserved in the bank.

The lymphocytic cell subsets are derived from an allogeneic donor source, for example, the peripheral blood, apheresis product or bone marrow from a naïve, healthy donor and/or cord blood sample. In some embodiments, the allogeneic sample is not derived from a patient's previous stem cell transplant donor. The $CD4^+$ and $CD8^+$ T-cells of the lymphocytic subsets are HLA-typed and the donor source recorded. The lymphocytic cell subsets' activation response can be verified and characterized, for example, via ELISPOT IFN-γ assay, or other known indicator of activation, to quantify the activity of each of the lymphocytic cell subsets individually, or the cell composition as a whole, where applicable. Furthermore, the lymphocytic cell subsets' antigenic recognition response is further characterized through its corresponding HLA-allele where applicable, for example through an HLA restriction assay. The lymphocytic cell subsets can be cryopreserved and stored. In one embodiment, the lymphocytic cell subsets are stored by the donor source. In one embodiment, the lymphocytic cell subsets are stored by TAA specificity. In one embodiment, the lymphocytic cell subsets are stored by human leukocyte antigen (HLA) subtype and restrictions.

By characterizing each lymphocytic cell subsets' reactivity and corresponding HLA-allele, the fixed ratio cell compositions described herein can be optimized for each patient based on specific lymphocytic cell subset reactivity and HLA matching, providing a highly personalized cell therapy. In this way, the cell therapy can be tailored to evoke a maximal response against the patient's disorder.

The establishment of a lymphocytic cell subset bank comprising discrete, characterized lymphocytic cell subsets for selection and inclusion in a fixed ratio composition bypasses the need for an immediately available donor and eliminates the wait required for autologous T cell production. Preparing a lymphocytic cell subset directed to specific, known tumor antigens by using donors, for example healthy volunteers or cord blood, allows the production and banking of lymphocytic cell subsets readily available for administration. Because the lymphocytic cell subsets are characterized, the selection of suitable lymphocytic cell subset can be quickly determined based on minimal information from the patient, for example HLA-subtype and, optionally TAA or VATA expression profile.

From a single donor a fixed ratio cell composition can be generated for use in multiple patients who share HLA alleles that have activity towards a specific TAA or VATA. The lymphocytic cell subset bank of the present invention includes a population of lymphocytic cell subset which have been characterized as described herein. For example, the lymphocytic cell subset of the bank are characterized as to HLA-subtype, where applicable, and one or more of i) TAA specificity of the $CD4^+$ and $CD8^+$ T-cell subpopulations; ii) TAA epitope(s) the $CD4^+$ and $CD8^+$ T-cell subpopulations are specific to; iii) $CD4^+$ and $CD8^+$ T-cell MHC Class I and Class II restricted subsets; and iv) antigenic activity through the $CD4^+$ and $CD8^+$ T-cell's corresponding HLA-allele. In addition, the bank can include information on the activity of activated γδ T-cells, $CD3^+$ NKT-cells, and/or CD3-NK cells.

In one embodiment, the present invention is a method of generating a lymphocytic cell subset bank for use in generating fixed ratio cell compositions described herein comprising: (i) obtaining eligible donor samples; (ii) generating $CD8^+$ and $CD4^+$ T-cell subpopulations specific to one or more TAAs or VATAs; (iii) generating and characterizing activated γδ T-cells, $CD3^+$ NKT-cells, and/or $CD3^-$ NK cells; (iv) cryopreserving the lymphocytic cell subsets; and (v) generating a database of lymphocytic cell subset composition characterization data. In one embodiment, the T lymphocytic cell subsets are stored according to their donor source. In one embodiment, the lymphocytic cell subsets are stored by TAA or VATA specificity. In one embodiment, the lymphocytic cell subsets are stored by human leukocyte antigen (HLA) subtype and restrictions.

The banked T-cell subpopulations described herein are used to comprise a fixed ratio cell composition for administration to a patient following the determination of the patient's HLA subtype.

Administration

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338, each of which are incorporated by reference in their entireties.

In some embodiments, the cells and compositions are administered to a patient in an therapeutically effective amount in the form of a pharmaceutical composition, such as a composition comprising the cells or cell populations and a pharmaceutically acceptable carrier or excipient. The pharmaceutical compositions in some embodiments additionally comprise other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The choice of carrier in the pharmaceutical composition may be determined in part particular method used to administer the cell composition. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition.

In addition, buffering agents in some aspects are included in the composition. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins 21st ed. (May 1, 2005).

In some embodiments, the pharmaceutical composition comprises the cells or cell populations in an amount that is effective to treat or prevent the disease or condition, such as a therapeutically effective or prophylactically effective amount. Thus, in some embodiments, the methods of administration include administration of the cells and populations at effective amounts. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio as described herein, e.g., within a certain tolerated difference or error of such a ratio.

In some embodiments, the cells are administered at or within a tolerated difference of a desired dose of one or more of the individual populations or sub-types of cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

In some embodiments, the cells are administered at or within a tolerated difference of a desired dose of one or more of the individual populations or sub-types of cells. In some aspects, the desired dose is a desired number of cells of the sub-type or population, or a desired number of such cells per unit of body size of the subject to whom the cells are administered, e.g., cells/$m^2$. In some aspects, the desired dose is at or above a minimum number of cells of the population or sub-type, or minimum number of cells of the population or sub-type per unit of body size. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of lymphocytic cell subsets and a desired ratio thereof.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $10^4$ and at or about $10^9$ cells/kilograms (kg) body weight, such as between $10^5$ and $10^6$ cells/kg body weight, for example, at or about $1\times10^5$ cells/kg, $1.5\times10^3$ cells/kg, $2\times10^3$ cells/kg, or $1\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. In some embodiments, the cells are administered at or within a certain range of error of between at or about $10^4$ and at or about $10^9$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight.

In some embodiments, the dose of total cells and/or dose of individual sub-populations of cells is within a range of between at or about $1\times10^6$ cells/$m^2$ and at or about $5\times10^8$ cells/$m^2$. For example, in some embodiments, the cells are administered at, or within a certain range of error of, between at or about $1\times10^6$ cells/$m^2$ and $5\times10^8$ cells/$m^2$.

In some embodiments, the cells are administered at or within a certain range of error of between at or about $1\times10^6$ cells/$m^2$ and $5\times10^8$ cells/$m^2$, for example at or about $1\times10^6$ cells/$m^2$, $2\times10^6$ cells/$m^2$, $3\times10^6$ cells/$m^2$, $4\times10^6$ cells/$m^2$, $5\times10^6$ cells/$m^2$, $6\times10^6$ cells/$m^2$, $7\times10^6$ cells/$m^2$, $8\times10^6$ cells/$m^2$, $9\times10^6$ cells/$m^2$, $1\times10^7$ cells/$m^2$, $2\times10^7$ cells/$m^2$, $3\times10^7$ cells/$m^2$, $4\times10^7$ cells/$m^2$, $5\times10^7$ cells/$m^2$, $6\times10^7$ cells/$m^2$, $7\times10^7$ cells/$m^2$, $8\times10^7$ cells/$m^2$, $9\times10^7$ cells/$m^2$, $1\times10^8$ cells/$m^2$, $2\times10^8$ cells/$m^2$, $3\times10^8$ cells/$m^2$, $4\times10^8$ cells/$m^2$, or $5\times10^8$ cells/$m^2$.

Monitoring

Following administration of the cells, the biological activity of the administered cell populations in some embodiments is measured, e.g., by any of a number of known methods. Parameters to assess include specific binding of a T-cell or other immune cell to antigen, in vivo, e.g., by imaging, or ex vivo, e.g., by ELISA or flow cytometry. In certain embodiments, the ability of the administered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as IFNγ, IL-2, and TNF. In some aspects the biological activity is measured by assessing clinical outcome, such as reduction in tumor burden or load.

EXAMPLES

Example 1—Immunotherapy of Relapsed and Refractory Solid Tumors with Ex-Vivo Expanded Non-Fixed Ratio Multi-Antigen Associated Specific Cytotoxic T Lymphocytes Patients and Treatment Protocol A phase 1 dose escalation trial was conducted to determine the safety of administering non-fixed ratio tumor-associated antigen cytotoxic T cells (TAA-T) targeting WT1, PRAME, and survivin to patients with high-risk solid tumors defined as refractory, relapsed or with residual detectable disease following conventional therapy. The TAA-T products administered in this trial were manufactured as described in Example 2 below and characterized with respect to tumor antigen specificity and the in vivo cytokine and lymphocyte cellular milieu pre- and post-infusion as described in Example 3. Disease response was evaluated following TAA-T therapy within the context of a phase 1 trial. Patients with high risk solid tumors reported to express one or more target tumor antigens (WT1, PRAME, and/or survivin) were eligible. Standard performance status and organ function parameters were required prior to cell procurement and TAA-T infusion. Informed consent was obtained from each patient or guardian. This study was approved by the US Food and Drug Administration (IND 16135) and Children's National Medical Center Institutional Review Board (NCT02789228).

Three TAA-T dose levels were evaluated; 1, 2 and $4\times10^7$ cells/$m^2$, with 2 to 4 patients enrolled at each dose level and expansion up to 8 patients at the maximum tolerated dose. Dose escalation occurred when two patients completed an initial 45-day post infusion evaluation period. TAA-T were infused a minimum of 1 week following conventional tumor directed therapy. When possible, antineoplastic cytotoxic agents were held for 6 weeks following TAA-T infusion. The first and second TAA-T doses were administered a minimum of 45 days apart and subsequent doses administered every 28 days. Patients without disease progression were eligible to receive up to 8 TAA-T doses at the enrollment dose level.

TAA-T were administered intravenously (1 ml/$10\text{-}12^7$ cells) in an outpatient setting over 1 to 2 minutes according to methods previously described (Cruz et al. "Adverse Events Following Infusion of T cells for Adoptive Immunotherapy: a 10-year Experience. Cytotherapy. 2010; 12(6): 743-749). Patients were monitored for 1-hour post infusion.

Dose limiting toxicity (DLT) to assess safety and determine the recommended TAA-T dose, were defined as: grade≥3 infusion-related adverse event, grade≥4 non-hematologic adverse event not related to the patient's underlying malignancy or pre-existing co-morbidities, grade≥3 acute graft versus host disease or any unexpected toxicity of any grade attributed to the infusion of TAA-T. Toxicities were defined by the NCI Common Terminology Criteria for Adverse Events (CTCAE), Version 4.03. Response for patients with measurable disease was according to RECIST v 1.1 criteria (Eisenhauer et al., New Response Evaluation Criteria in Solid Tumors: Revised RECIST guideline (version 1.1) *Eur. J Cancer.* 2009; 45(2): 228-247). Time to progression was measured for patients without measurable disease.

Figure 3:
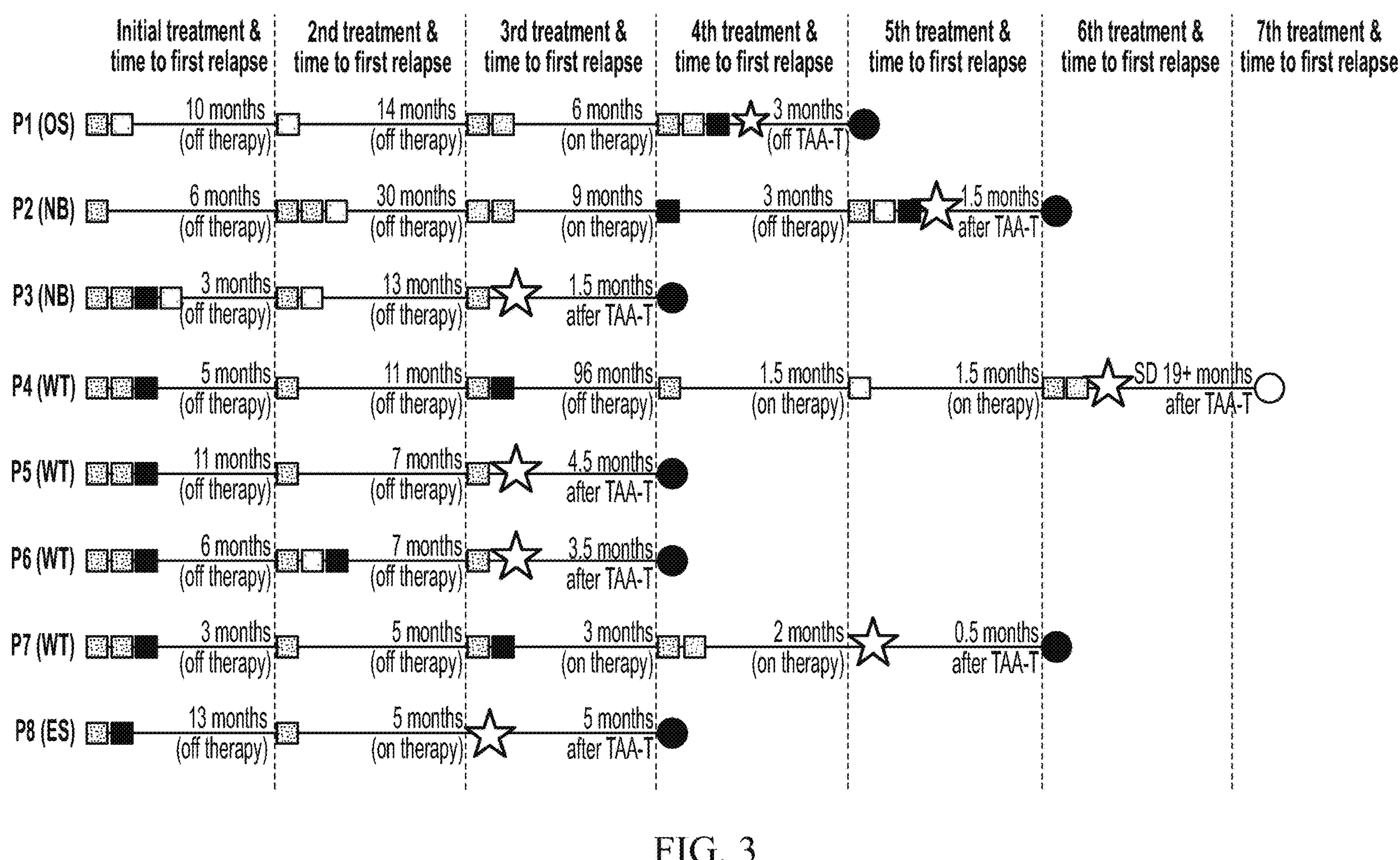
FIG. 3: Multimodality therapy administered prior to TAA-T infusion. Patients experienced relapsed disease following completion of therapy as well as disease progression while on treatment. *Targeted therapy includes: denosumab (P1), dinutuximab (P2, P3), radiolabeled I-131 MIBG (P2, P3), lorvotuzumab (P2, P4). SD=stable disease; PD=progressive disease.
Figure 3:
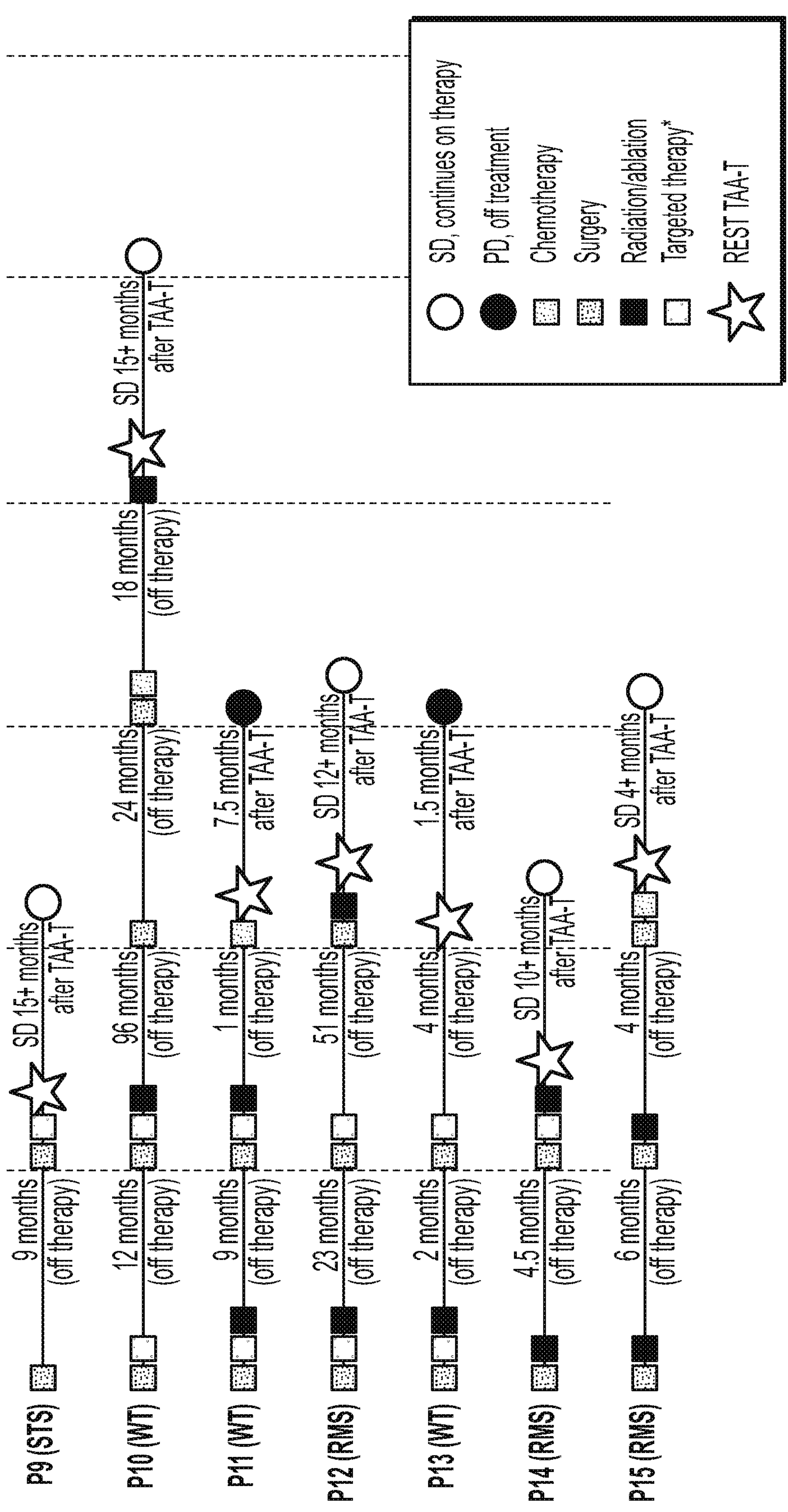

Eighteen patients (10 males, 8 females) with solid tumor malignancies including Wilms tumor (n=9), rhabdomyosarcoma (n=4), neuroblastoma (n=2), soft tissue sarcoma (n=1), Ewing sarcoma (n=1), and osteosarcoma (n=1) were enrolled. The median age at enrollment was 8.5 years (range 3-53 years). All patients had received multi-modal therapy prior to receiving TAA-T (FIG. 3). One patient underwent cell procurement without achieving an adequate cell number; one patient has a viable cryopreserved product awaiting infusion and one patient developed rapid disease progression precluding TAA-T infusion. A total of 45 TAA-T infusions were administered (median 2 infusions per patient, range 1-8). One patient did not complete the 45-day observation period following TAA-T infusion due to disease progression. The remaining 14 patients were evaluable for toxicity.

Patient response was defined as follows:

Evaluable disease: The presence of at least one lesion, with no lesion that can be accurately measured in at least one dimension. Such lesions may be evaluable by nuclear medicine techniques, immunocytochemistry techniques, tumor markers or other reliable measures. Complete response: disappearance of all evaluable disease.

Partial response: Decreased evidence of disease (in all sites) without meeting criteria for complete response.

Stable disease: Changes insufficient to qualify for other responses.

Progressive disease: The appearance of one or more new lesions or evidence of laboratory, clinical, or radiographic progression.

Non-measurable disease: All other lesions (or sites of disease), including small lesions (longest diameter<10 mm or pathological lymph nodes with ≥10 to <15 mm short axis), are considered non-measurable disease. Bone lesions, leptomeningeal disease, ascites, pleural/pericardial effusions, lymphangitis cutis/pulmonitis, inflammatory breast disease, and abdominal masses (not followed by CT or MRI), are considered as non-measurable.

Example 2: Manufacture of Non-Fixed Ratio TAA-T Products

Non-Fixed Ratio TAA-T products from patients having solid tumors were generated according to Good Manufacturing Practices appropriate for a phase I study. A total of 100-120 mL of peripheral blood was collected on 2 occasions to generate antigen-presenting cells. For patients weighing less than 25 kg, each collection volume was reduced to 3 mL/kg. Subsequent collections were permitted for patients eligible to continue on therapy but without additional cell doses.

Figure 2:
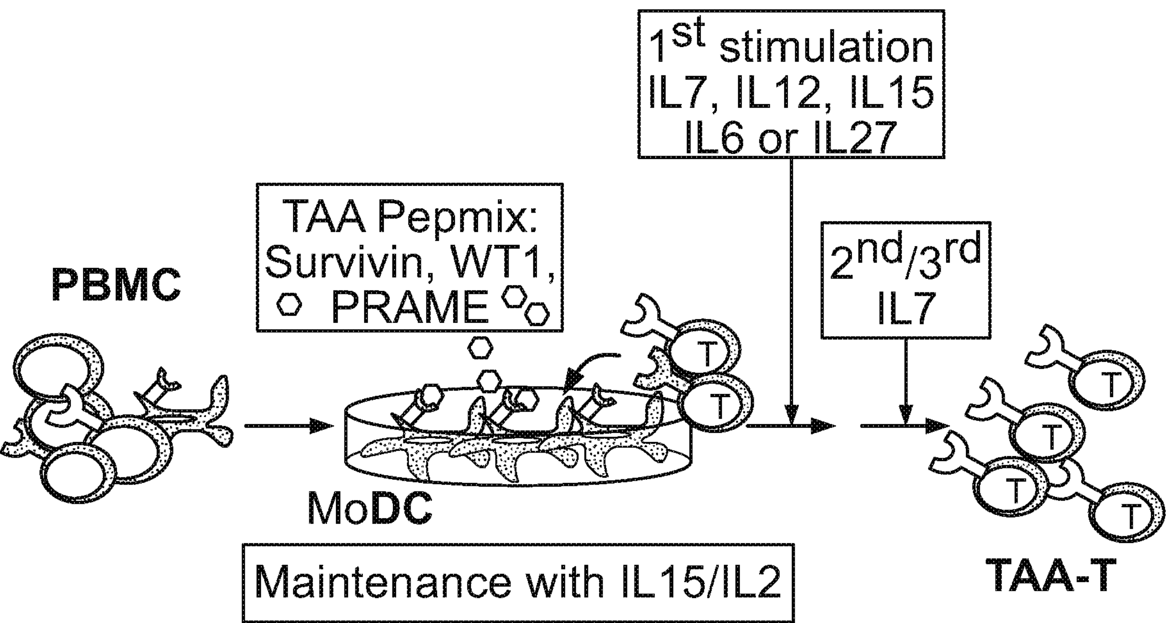
FIG. 2: Schematic of the generation of antigen-specific T-cell lines. Donor or patient PBMCs were primed with autologous dendritic cells pulsed with 3 TAAs (Survivin, WT1, and PRAME) at an effector-to-target ratio of 10:1 in the presence of a cytokine-mix containing IL-7, IL-12, IL-15, IL-6, and IL-27. For the subsequent stimulations IL7 was used. For the further maintenance of CTLs IL-15 and IL-2 was used.

Non-fixed ratio TAA-T products were generated from total human blood peripheral mononuclear cells (Step 1). Matured dendritic cells (DCs) were harvested and used as antigen presenting cells (APCs) and peptide-pulsed with a mix of three peptide libraries for WT-1, Survivin, and PRAME (Step 2). Lymphocytes were initially stimulated using a cytokine mix containing IL-7, IL-12, IL-15, IL-6, and IL-27 (Step 3). Subsequent stimulation (Steps 4 and 5) were performed using irradiated DCs or irradiated phytohemagglutinin (PHA) blasts. See generally FIG. 2. Generally applicable experimental procedures for each of these steps are provided below.

Step 1. Isolation of Mononuclear Cells

Heparinized peripheral blood was diluted in an equal volume of warm RPMI 1641 (Invitrogen) or PBS. In a 50 mL centrifuge tube, 10-15 mL of Lymphoprep (Axis-Shield) was overlayed with 20-30 mL of diluted blood. The mixture was centrifuged at 800×g for 20 minutes or 400×g for 40 minutes at ambient temperature, ensuring that acceleration and deceleration were set to "1" to prevent disrupting the interface. 1 mL of plasma aliquots were saved and stored at −80° C. The peripheral blood mononuclear cell (PBMC) interface was harvested into an equal volume of RPMI 1640, centrifuged at 450×g for 10 minutes at ambient temperature, and the supernatant was aspirated. The pellet was loosened and the cells were resuspended in a volume of RPMI 1640 or PBS that yields and estimated $10\times10^6$ cells/mL. An aliquot of cells was removed for counting using 50% red cell lysis buffer or Trypan blue and using a hemocytometer. The PBMCs were saved for DC generation using adherence (Step 2 below) and non-adherent cells were cryopreserved for use at initiation.

Step 2. Dendritic Cell (DC) Generation

PBMCs were centrifuged at 400×g for 5 minutes at ambient temperature, and the supernatant was aspirated. The cells were resuspended at approximately $5\times10^6$ cells/mL in CellGenix DC medium containing 2 mM of Glutamax (Invitrogen), and the cells were plated in a 6-well plate (2 mL/well). The PBMC non-adherent fraction was removed after 1-2 hours, and the wells were rinsed with 2-5 mL of CellGenix DC medium or PBS and added to the harvested medium/non-adherent fraction. The non-adherent fraction was saved for later cryopreservation. 2 mL of DC medium containing 1,000 U/mL of IL-4 (R&D Systems) and 800 U/mL GM-CSF (CNMC Pharmacy) was added back to the adherent cells. All surrounding wells were filled with approximately 2 mL of sterile water or PBS to maintain the humidity within the plate, and the plate was placed in the incubator at 37° C. and 5% $CO_2$. On day 3 to 4, the cells were fed with 1,000 U/mL IL-4 and 800 U/mL GM-CSF. On day 5 to 6, the DCs were matured in 2 mL/well of DC medium containing lipopolysaccharide (LPS, Sigma) (30 ng/mL), IL-4 (1,000 U/mL), GM-CSF (800 U/mL), TNF-α (10 ng/mL, R&D Systems), IL-6 (100 ng/mL, CellGenix), and IL-1p (10 ng/mL, R&D Systems). The mature DCs were harvested on day 7 to 8 by gentle resuspension. The cells were counted using a hemocytometer. The DCs were transferred to a 15 mL centrifuge tube and centrifuged for 5 minutes at 400×g at ambient temperature. The supernatant was aspirated, the pellet was resuspended by finger flicking, and 100 μL of appropriate Pepmix Mastermix (200 ng/peptide in 200 μL; PRAME, WT1, and Survivin Pepmixes; JPT Peptide Technologies) per $1\text{-}5\times10^6$ cells was added to the DCs. The DCs and Pepmixes were mixed and transferred to the incubator. The mixture was incubated for 60-90 minutes at 37° C. and 5% $CO_2$.

Step 3. Cytotoxic T Lymphocyte(CTL) Initiation

After pulsing with Pepmix, the DCs were irradiated at 25 Gy. The DCs were washed with DC medium and centrifuged at 400×g for 5 minutes at ambient temperature. The supernatant was aspirated, and the wash step was repeated twice more. The cells were counted using a hemocytometer. The DCs were resuspended at $2\text{-}4\times10^5$ cells/mL of CTL medium with 10% human serum (HS, Valley) for initiation. 1 mL of irradiated DCs/well were plated in a 24-well tissue culture treated plate.

Previously-frozen PBMCs from Step 1 were thawed at 37° C. and diluted in 10 mL of warm medium/i mL of frozen cells. The PBMCs were centrifuged at 400×g for 5 minutes at ambient temperature and resuspended in 5-10 mL of medium, and a cell count was performed using a hemocytometer. The PBMCs were resuspended at $2\times10^6$ cells/mL. DCs and PBMCs were recombined in the plate to stimulate CTL at a 1:10 to 1:5 ratio of DCs: CTL. Cytokines IL-7, IL-15, IL-6, and IL-12 were added to achieve a final concentration of IL-7 (10 ng/mL, R&D Systems), IL-15 (5 ng/mL, CellGenix), IL-6 (100 ng/mL, CellGenix), and IL-12 (10 ng/mL, R&D Systems). All surrounding wells were filled with approximately 2 mL of PBS to maintain humidity within the plate. The cells were cultured in the incubator at 37° C. and 5% $CO_2$ for 7 to 8 days. A one-half medium change was performed on day 4 to 5, with the wells being split 1:1 if nearly confluent.

Step 4. Second CTL Stimulation in 24-Well Plate

The second stimulation of CTLs was performed using either PepMix-Pulsed Autologous DCs (Procedure A) or PepMix-Pulsed Autologous Phytohemagglutinin (PHA) Blasts (Procedure B) as antigen presenting cells.

Procedure A: Stimulation Using PepMix-Pulsed Autologous DCs as Antigen Presenting Cells (APCs)

After pulsing with the appropriate Pepmix (PRAME, WT1, and Survivin Pepmixes; JPT Peptide Technologies), the DCs were irradiated at 25 Gy. The DCs were washed with DC medium and centrifuged at 400×g for 5 minutes at ambient temperature. The supernatant was aspirated, and the wash step was repeated twice more. The cells were counted using a hemocytometer. The DCs were resuspended at $0.5\text{-}2\times10^5$ cells/mL of CTL medium with 10% HS (Valley) for initiation. 1 mL of irradiated DCs/well ($0.5\text{-}2\times10^5$ cells) were plated in a 24-well tissue culture treated plate. CTLs were counted using a hemocytometer. The cells were resuspended at $1\times10^6$ cells/mL of CTL medium supplemented with IL-7 (10 ng/mL final concentration, R&D Systems)) and IL-2 (100 U/mL final concentration, Proleukin) and 1 mL was aliquoted per well of the 24-well plate. The cells were cultured in the incubator at 37° C. and 5% $CO_2$ for 3 to 4 days. The medium was changed with IL-2 (~100 U/mL final concentration, Proleukin) and cultured for another 3 to 4 days. Cells were optionally frozen after the second stimulation.

Procedure B: Stimulation Using PepMix-Pulsed Autologous Phytohemagglutinin (PHA) Blasts as APCs Autologous PHA blasts were harvested on day 7 by gentle resuspension, and cells were counted using a hemocytometer. The PHA blasts were transferred to a 15 mL centrifuge tube and centrifuged for 5 minutes at 400×g at ambient temperature. The Supernatant was aspirated and the pellet was resuspended by finger flicking. 100 μL of appropriate PepMix Mastermix (200 ng/peptide in 200 μL; PRAME, WT1, and Survivin Pepmixes; JPT Peptide Technologies) was added to PHA blasts per $1\text{-}10\times10^6$ cells. The PHA blasts were incubated for 30-60 minutes. The PHA blasts were resuspended in 5-10 mL of medium and irradiated at 50 Gy (or 100 Gy if used in G-rex). The PHA blasts were washed with CTL medium and centrifuged at 400×g for 5 minutes at ambient temperature. The supernatant was aspirated, and the washing step was repeated twice more. A cell count was performed using a hemocytometer. The PHA blasts were resuspended at 0.5×106 cells/mL of CTL medium to re-stimulate CTL at an approximate ratio of 1:1 PHA blasts: CTL. The CTLs were counted using a hemocytometer. The CTL were resuspended at $0.5\times10^6$ cells/mL of CTL medium supplemented with IL-7 (100 ng/mL final concentration; R&D Systems) and IL-2 (100 U/mL final concentration; Proleukin). One well of only PHA blasts was maintained as an irradiation control. The cells were cultured in the incubator at 37° C. and 5% $CO_2$ for 3 to 4 days. The medium was changed with IL-2 (100 U/mL final concentration; Proleukin) and the cells were cultured for another 3 to 4 days.

Step 5. Third CTL Stimulation in G-Rex10 Using PHA Blasts as APCs

Autologous PHA blasts were harvested on day 7 by gentle resuspension, and cells were counted using a hemocytometer. The PHA blasts were transferred to a 15 mL centrifuge tube and centrifuged for 5 minutes at 400×g at ambient temperature. The supernatant was aspirated, and the pellet was resuspended by finger flicking. 100 μL of appropriate PepMix Mastermix (200 ng/peptide in 200 μL; PRAME, WT1, and Survivin Pepmixes; JPT Peptide Technologies) was added to PHA blasts per 1-10×$10^6$ cells, and the PHA blasts were incubated for 30-60 minutes. The PHA blasts were resuspended in 5-10 mL of medium and irradiated at 50 Gy (or 100 Gy if used in G-Rex). The PHA blasts were washed with CTL medium and centrifuged at 400×g for 5 minutes at ambient temperature. The supernatant was aspirated, and the washing step was repeated twice more. Cells were counted using a hemocytometer. The PHA blasts were resuspended at 0.5×$10^6$ cells/mL of CTL medium to re-stimulate CTL at an approximate ratio of 1:1 PHA blasts: CTL. 10 mL of cell suspension was added in the G-Rex10 and 1 mL/well (0.5×$10^6$ PHA blasts) was the 24-well control plate. The CTLs were counted using a hemocytometer. The CTLs were resuspended at 0.5×$10^6$ cells/mL of CTL medium, and 10 mL (5×$10^6$ CTLs) was added in the G-Rex10 and 1 mL/well (0.5×$10^6$ CTLs) in the 24-well control plate. The medium was supplemented with IL-7 (10 ng/mL final concentration; R&D Systems) and IL-2 (100 U/mL final concentration; Proleukin), and the cells were cultured in the incubator at 37° C. and 5% $CO_2$ for 3 to 4 days. One well of the 24 well plate was left with PHA blasts only as an irradiation control. The medium was changed with IL-2 (100 U/mL final concentration; Proleukin), and the cells were cultured for an additional 3 to 4 days.

Final non-fixed ratio TAA-T products were evaluated for specificity, phenotype and sterility followed by cryopreservation until infusion (where applicable). Products were required to meet sterility criteria at the time of infusion and lack reactivity to autologous phytohemagglutinin (PHA) blasts with less than 10% lysis to PHA blasts. Flow cytometry defined the cell product phenotype with requirements <2% dendritic cells and <2% B cells.

Example 3: Characterization of Non-Fixed Ratio TAA-T Products

Flow Cytometry

Figures 4A, 4B, 4C, 4D:
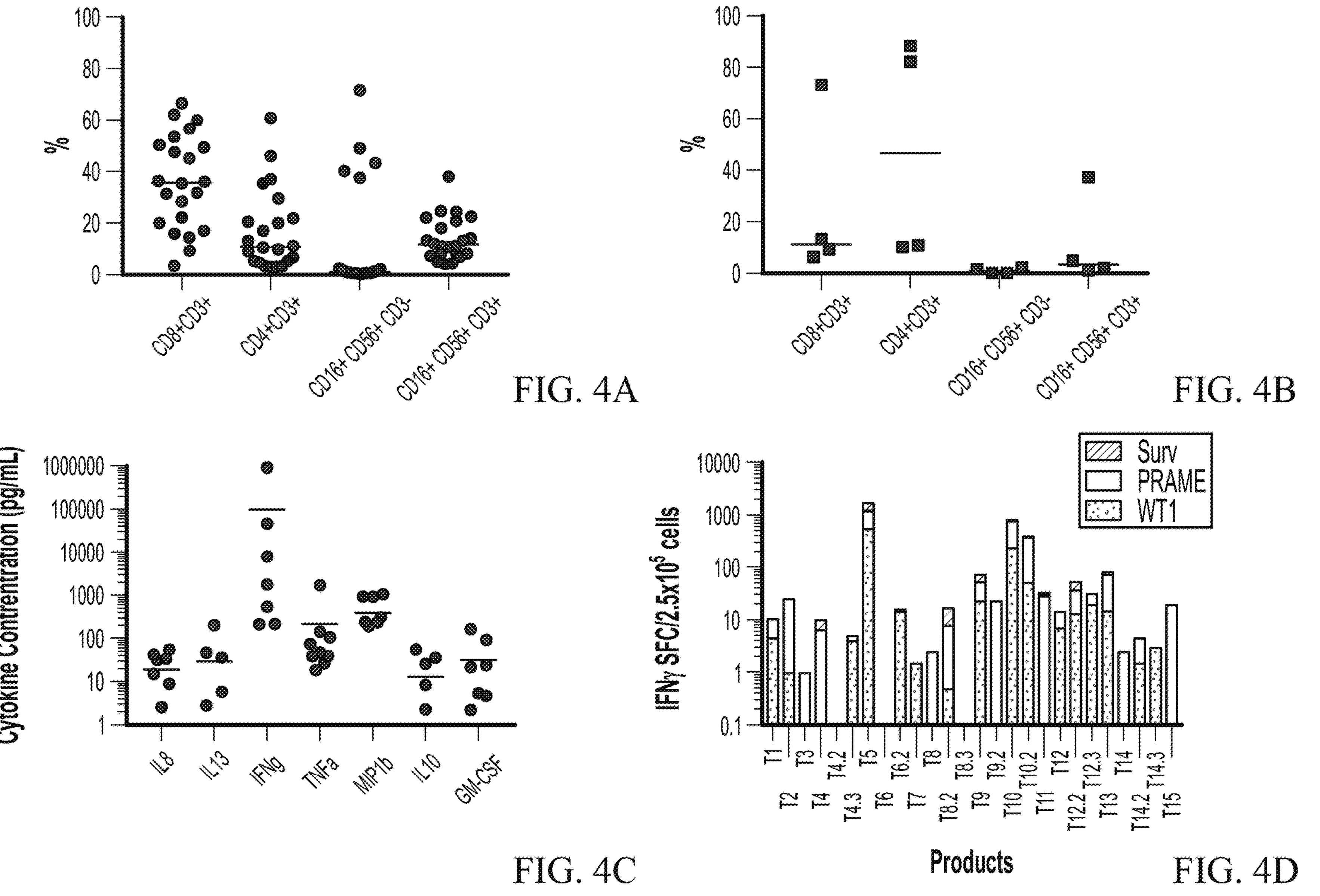
FIG. 4A: Flow cytometry demonstrates a variable phenotype of polyclonal, polyfunctional T cell products in patients in the Responding group.
FIG. 4B: Patients in the Non-responding group showed comparatively lower percentage of $CD8^+$ T cells and $CD3^+$ $CD16^+$ cells with high percentages of $CD4^+$ T cells.
FIG. 4C: Luminex assay to measure cytokine secretion by TAA-T products. IFNγ, TNFα, and MIP1b were the cytokines most commonly detected in response to antigen stimulation.
FIG. 4D: Product TAA specificity as measured by ELISpot. Number on the x-axis corresponds to patient number, and when applicable multiple products are numbered accordingly (e.g., T4, T4.2, and T4.3 are the 1st, 2nd, and 3rd products administered to P4). TAA-T products demonstrated variable specificity to the targeted antigens. PRAME was the antigen to which most products were specific, followed by WT1.

Non-fixed ratio TAA-T products derived using the procedure of Example 2 above were phenotyped by extracellular antibody staining with anti-CD3, CD4, CD8, CD45, CD19, CD16, CD56, CD14, CD45, CD83, HLA-DR, TCRαβ, TCRγδ (Miltenyi Biotec, Auburn, California) and analyzed on MACSQuant Analyzer10 Flow Cytometer. Annexin-V and PI antibodies were used as viability controls, and data analyzed with FlowJo Flow Cytometry software (Treestar, Ashland, OR, USA). The phenotyping results for the non-fixed ratio TAA-T products generated from patients are shown in FIG. 4A and FIG. 4B, which indicates a variability in lymphocytic cell types.

ELISpot

Antigen specificity of the non-fixed ratio TAA-T products derived using the procedure of Example 2 above was tested via Interferon-Enzyme-Linked Immunospot (IFNγ ELISpot) assay. See Weber G, Caruana I, Rouce R H, et al. Generation of tumor antigen-specific T cell lines from pediatric patients with acute lymphoblastic leukemia—implications for immunotherapy. Clin Cancer Res. 2013; 19(18):5079-5091.

Non-fixed ratio TAA-T products derived using the procedure of Example 2 above were tested for recognition of single antigens (WT1, PRAME, survivin) (JPT Peptide Technologies, Berlin, Germany), as compared to negative (actin) and positive controls [Staphylococcal enterotoxin B (SEB)]. IFNγ ELISpot was also performed on patient samples post infusion. $CD14^+$ cells were isolated from PBMCs cryopreserved at time of collection by MACS technology using CD14 microbeads (Miltenyi Biotec) and cultured in DC media with IL-4 and GM-CSF. Day 6-7, cells were pulsed with a peptide mixture of WT1, PRAME, survivin and used to stimulate CD14 negative cells. Cells were harvested day 14-15 and tested for specificity to the 3 targeted antigens as well as non-targeted tumor-associated antigens (melanoma-associated antigen (MAGE)-A3, MAGE-A4, SOX-2, and SSX-2) commonly identified in solid tumors.

Luminex Assay

Non-fixed ratio TAA-T products samples obtained at time of cryopreservation were characterized for cytokine production using the Bio-Plex 17-plex Luminex assay (Bio-Rad, Hercules, California). Non-fixed ratio TAA-T were placed in 4 wells of a 96-well round bottom tissue culture plate at a concentration of 1×$10^5$ cells/200 uL of CTL media. TAA pepmix (1 uL) and actin (1 uL) were added to 2 wells each. Cells were incubated overnight at 37° C., 5% $CO_2$. Supernatant was collected and frozen (−80° C.). Using T cell media for standardization, standard procedure was followed per Bio-Rad instructions. The plate was read using the default instrument settings for Bio-Plex MAGPIX System per the manufacturer's instructions. Data analyses performed using the Bio-Plex Manager software subtracting TAA-T cell response to actin. The Luminex 17-plex assay was performed on patient plasma collected on day of and post infusion. Plasma was collected by centrifugation at 1500×g for 15 minutes at 4° C. and frozen at −80° C. until time of assay. The assay was performed according to Bio-Rad instructions utilizing a standard diluent for standardization.

Example 4: Results

Twenty-seven non-fixed ratio TAA-T products were generated using the protocol of Example 2 from autologous sources for the 18 patients described in Example 1. For products infused, the median time from collection to clinical freeze was 28 days (range 22-31 days), with a median 12-fold expansion of T cells (range 3 to 65-fold) for all products.

Patients demonstrating stable disease or better at the initial day 45 evaluation time point following TAA-T infusion were deemed "responders" and those with progressive disease were classified as "non-responders". The phenotype of TAA-T products was compared between responders (FIG. 4A) versus non-responders (FIG. 4B). All products had a variable composition (median, range) of $CD8^+$ T cells (32.6%, 3.4-73.3%), $CD4^+$ T cells (11.1%, 3-88.3%), $CD16^+$ $CD56^+CD3^-$ NK cells (1.3%, 0.2-71.6%), and $CD16^+$ $CD56^+$CD3+ T cells (11%, 1.1-38%). B cells (0.17, 0-1.7%) and dendritic cells (0%, 0-1.4%) accounted for less than 2% of all final products. Responders received TAA-T cell products comprising higher $CD8^+$ $CD3^+$ T cells (median 35.7%, range 3.4-66%) compared to $CD4^+$ $CD3^+$ cells (10.8%, 3-60.9%) with variable numbers of $CD16^+$ $CD56^+$ $CD3^-$ NK cells (1.2, 0.3-71.6%) and $CD16^+$ $CD56^+$ $CD3^+$ cells (11.6%, 4.1-38). Products administered to patients defined as non-responders comprised lower $CD8^+$ $CD3^+$ T cells (11.3%, 6.4-73.3%) compared to $CD4^+$ $CD3^+$ T cells (46.5%, 10.2-88.3%), and variable $CD16^+$ $CD56^+$ $CD3^-$ NK cells (1.3%, 0.2-5%) and $CD16^+$ $CD56^+CD3^+$ cells (1.8%, 1.11-37.2%). The results are summarized in Table 1 below.

TABLE 1

| Cell Type | All Products (median) | Responders (median) | Non-Responders (median) |
|---|---|---|---|
| $CD3^+/CD8^+$ | 32.6% | 35.7% | 11.3% |
| $CD3^+/CD4^+$ | 11.1% | 10.8% | 46.5% |
| $CD3^+/CD56^+/CD16^+$ | 11% | 11.6% | 1.8% |
| $CD3^-/CD56^+/CD16^+$ | 1.3% | 1.2% | 1.3% |

The most consistent cytokine elevation in the non-fixed ratio TAA-T product as evaluated by the Luminex (17-plex) assay occurred for IFNγ (median 1157, range 0-920,110 pg/mL), TNFα (61, 0-1701 pg/mL), and MIP-1b (271, 0-1056 pg/mL) (FIG. 4C). Antigen specificity was evaluated using IFNγ ELISpot assay (FIG. 4D). All products demonstrated response to the SEB positive control with a median of 605.8 (range 152.5-939) IFNγ SFC/2.5e$^5$. The median actin response, a measure of non-specific activity, was 18.8 (0-159.5) IFNγ SFC/2.5e$^5$. A positive result for individual antigens was defined as 10 IFNγ SFC/2.5e$^5$ cells or greater following subtraction of actin. Response to specific antigens was as follows: WT1 median 1.5 (0-561) IFN SFC/2.5e$^5$ cells, PRAME median 7 (0-653.5) IFNγ SFC/2.5e$^5$ cells and survivin median 0 (0-540) IFN SFC/2.5e$^5$ cells.

Figure 5:
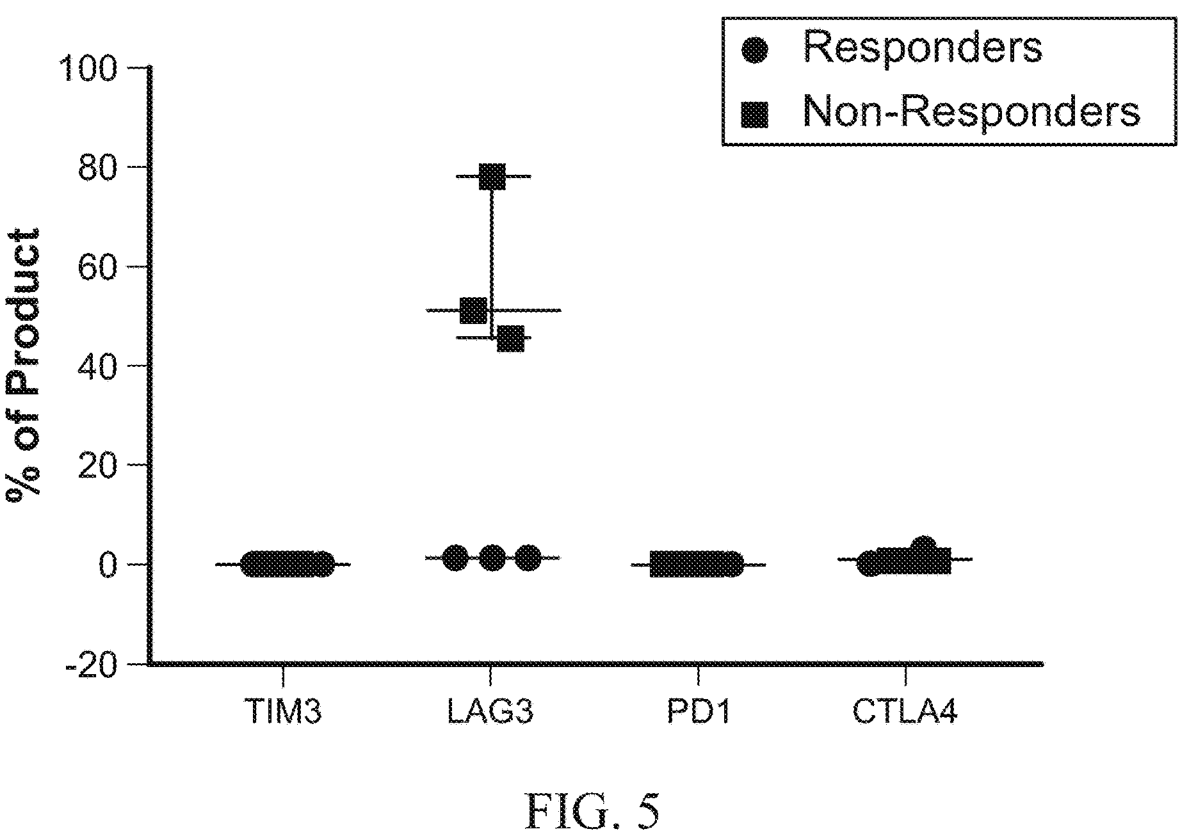
FIG. 5: Cell composition products administered to subjects responsive to therapy show low levels of exhaustion markers TIM-3, LAG-3, PD1, and CTLA-4. The x-axis represents the specifically measured $CD3^+$ exhaustion marker, and the y-axis represents the percentage of the product. Responder products had low levels of exhaustion markers, while non-responders showed increased levels of LAG-3.
Figure 6A:
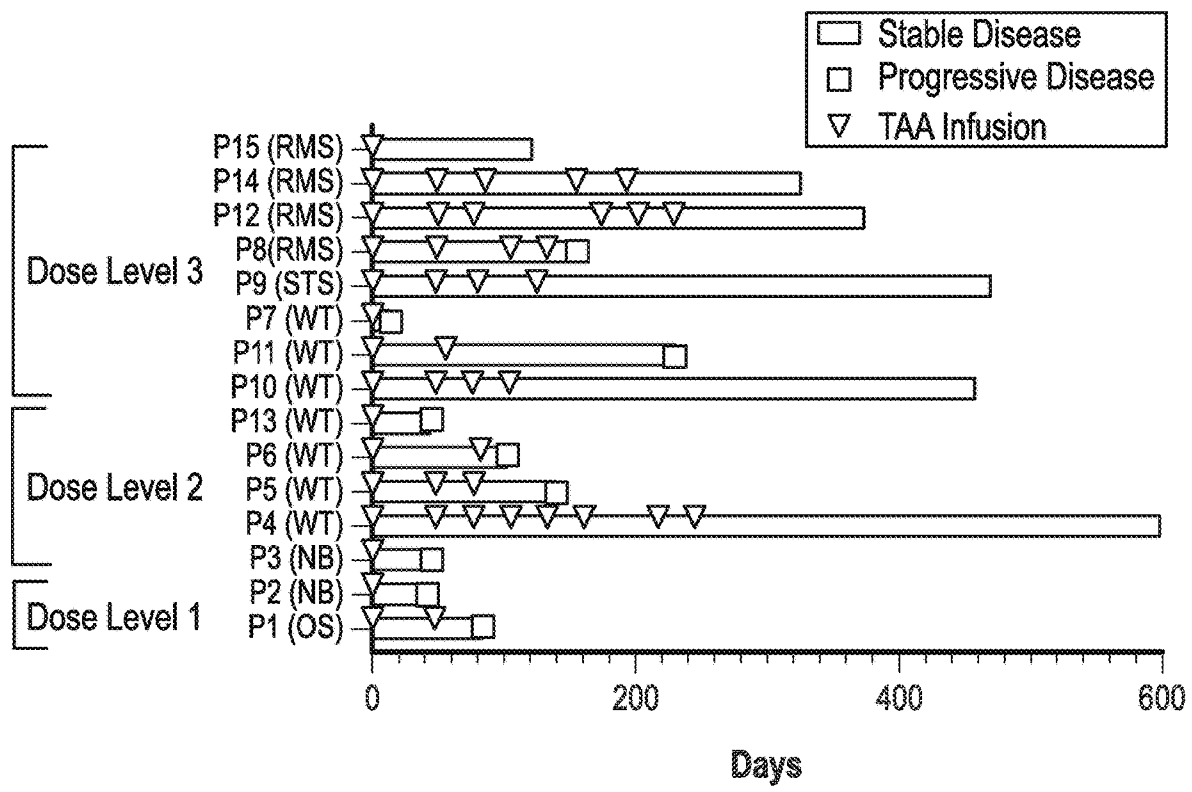
FIG. 6A: Outcome for evaluable patients who received at least one TAA-T infusion. Many patients were able to receive multiple TAA-T infusions without adverse reactions. Eleven of the 15 patients met criteria for response, which was defined as stable disease or better at the day 45 evaluation.
Figure 6B:
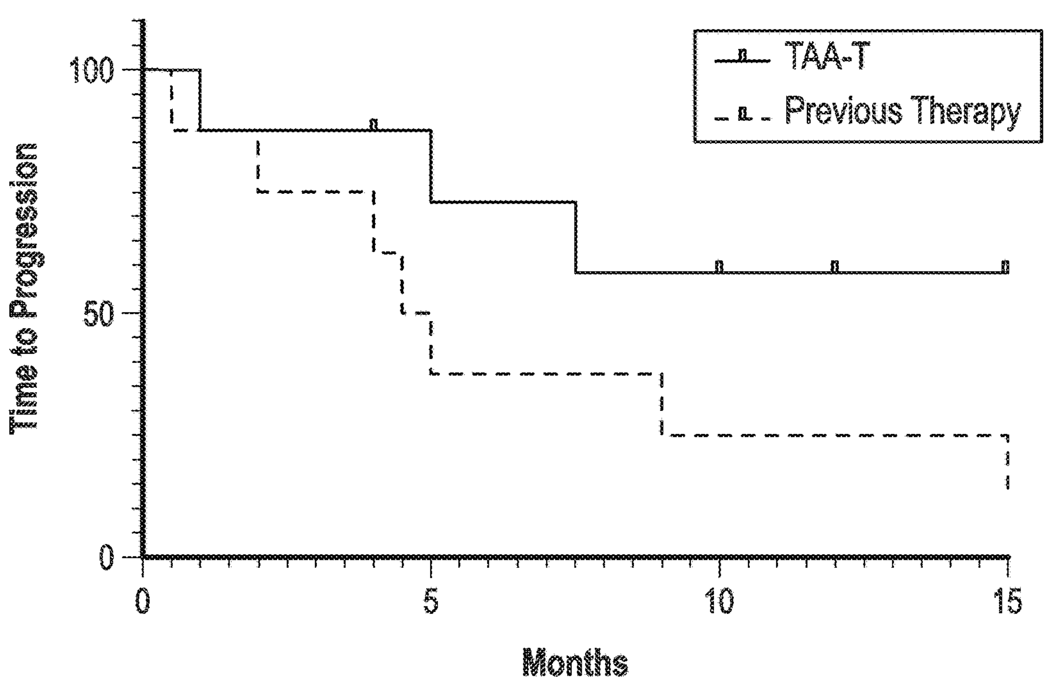
FIG. 6B: The PFS of patients following TAA-T therapy treated at the highest dose level was 73% at 6 months and 58% at 12 months as compared to their immediate prior therapy regimen, 38% and 25% respectively ($p=0.18$).

Non-fixed ratio TAA-T products demonstrated a polyclonal, polyfunctional phenotype with a small subset of $CD3^+$ $CD56^+$ $CD16^+$ T cells. There was a trend toward a lower fraction of $CD8^+$ T cells in products generated from non-responding patients (n=3). The expression of exhaustion markers PD1, CTLA4, and TIM3 was low in all the products tested but LAG3 was increased in 3 products (FIG. 5). Interestingly, these 3 products were all administered to patients defined as non-responders suggesting T cell exhaustion may have been a mechanism of product failure in vivo.

Of the 15 patients treated, 11 had evaluable disease at initial TAA-T infusion, 3 had measurable disease and 1 had an inevaluable MIBG avid lesion not amenable to confirmatory biopsy (P3). Of the 12 patients with evaluable disease/MIBG positivity, 10 patients had a best response of stable disease and 2 had progressive disease this included P3 who progressed with new metastatic disease. Of the 3 patients with measurable disease at the time of the first infusion, one of the 3 patients had a best response of stable disease and 2 patients had progressive disease.

Overall, eleven of the 15 evaluable patients (73%) responded. At dose level 1 ($1\times10^7$ cells/m$^2$), Patient 1 responded and received a second TAA-T infusion. Patient 2 had disease progression and came off protocol therapy. At dose level 2 ($2\times10^7$ cells/m$^2$), 3 of 5 patients (P4, P5, P6) responded. Patient 4 received 8 TAA-T infusions (maximum allowed per protocol), P5 received 3 infusions, and P6 2 infusions. Of the 8 patients treated on dose level 3 ($4\times10^7$ cells/m$^2$) 7 patients responded. Six of these 7 patients received multiple TAA-T infusions (median 4 doses, range 2-6). One patient (P15) had sufficient cells for a single infusion. Of the 11 responding patients, 6 patients have not progressed at a median of 13.9 (range 4.1-19.9) months post initial infusion (FIG. 9*a*). At the highest dose level 3 patients progressed (median duration of follow up 12.7 months, range 0.5-15.7). Their progression-free survival (PFS) at 6 and 12 months from the first TAA-T infusion was 73% and 58% respectively (FIG. 9*b*). This was markedly superior to the 6- and 12-month PFS observed following the therapy course immediately prior to TAA-T treatment, 38% and 25% respectively. While this difference was not statistically significant (p=0.18), there was a trend toward improved time to progression following TAA-T treatment as compared to their response to previous therapy.

Figure 7:
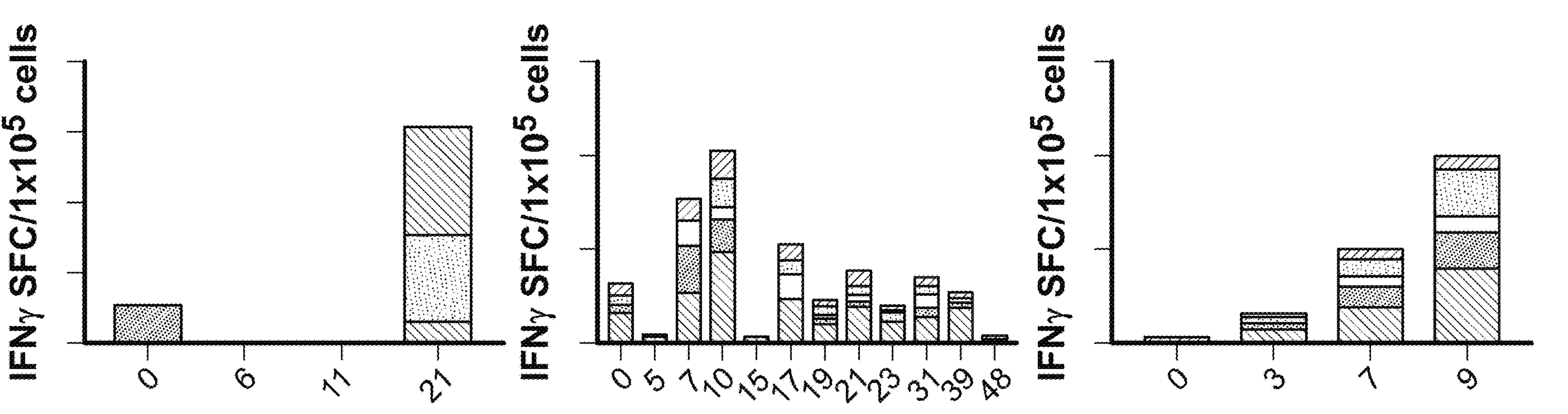
FIG. 7: IFNγ ELISpot was used to evaluate anti-tumor immunity to the targeted antigens (WT1, PRAME, survivin), as well as 4 non-targeted antigens commonly identified in solid tumors (MAGE A3, MAGE A4, SOX-2, SSX-2). Ten of 11 Responders demonstrated evidence of antigen spreading while receiving TAA-T infusions. P1 did not show increased specificity for targeted or non-targeted antigens until after disease progression at week 12.
Figure 7:
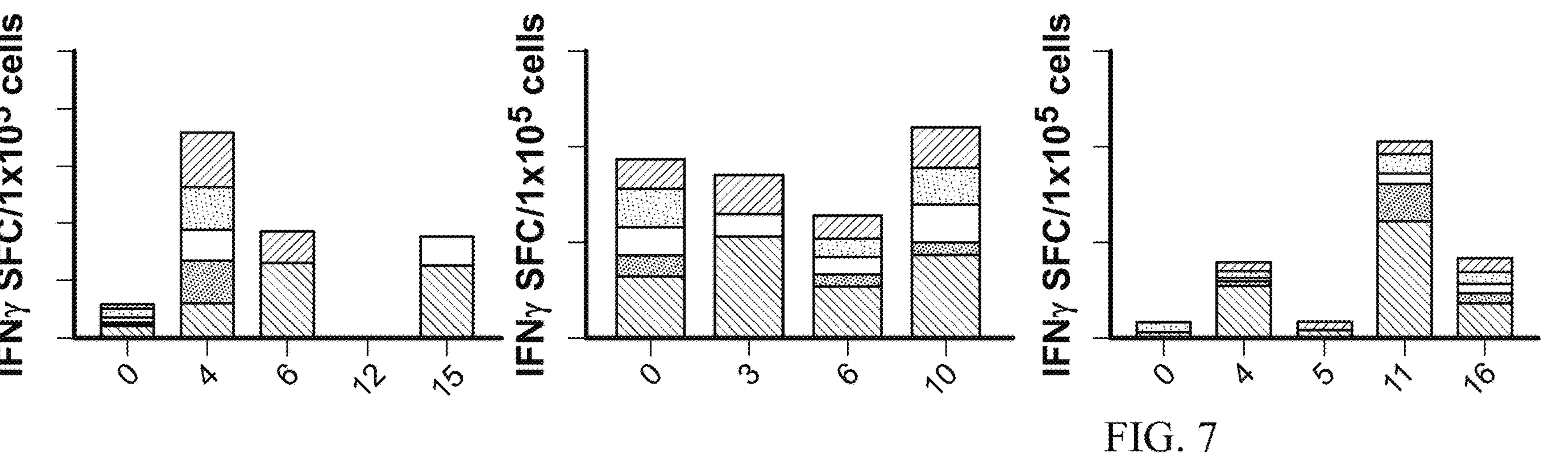
Figure 7:
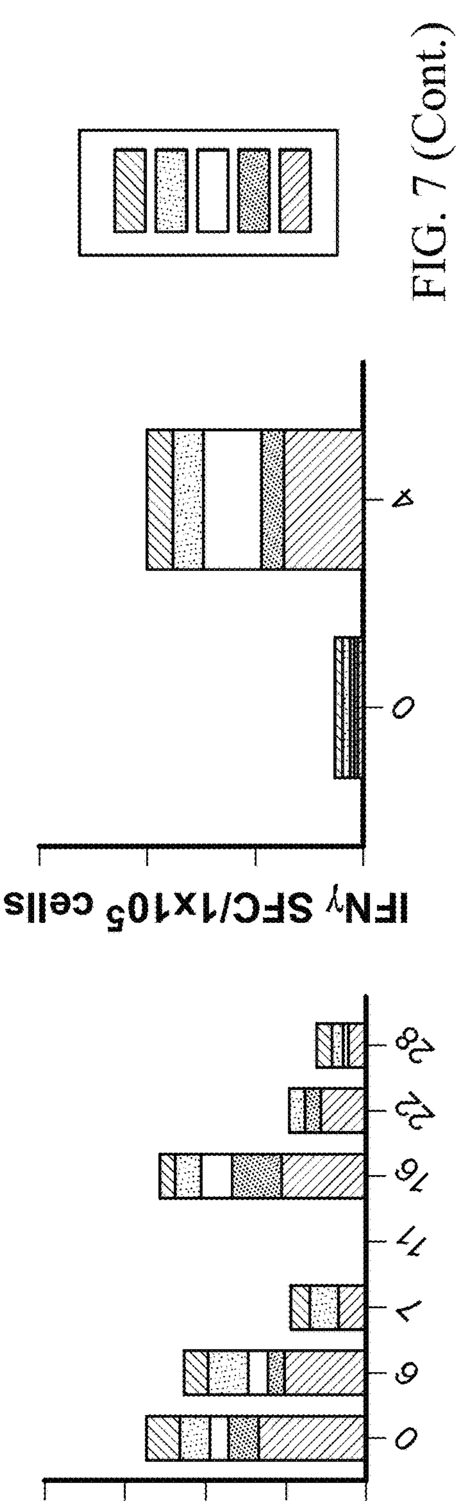

Ten of the 11 responding patients showed increased specificity for the 3 target tumor antigens as well as one or more non-targeted TAA (FIG. 7) suggesting antigen spreading following TAA-T infusion. Ten (91%) patients defined as responders demonstrated evidence of antigen spreading in contrast to 2 of 3 (67%) non-responding patients (data not shown).

Example 5. Methods to Generate Fixed Ratio TAA-T Products

General Cytometry Methods

Figure 8:
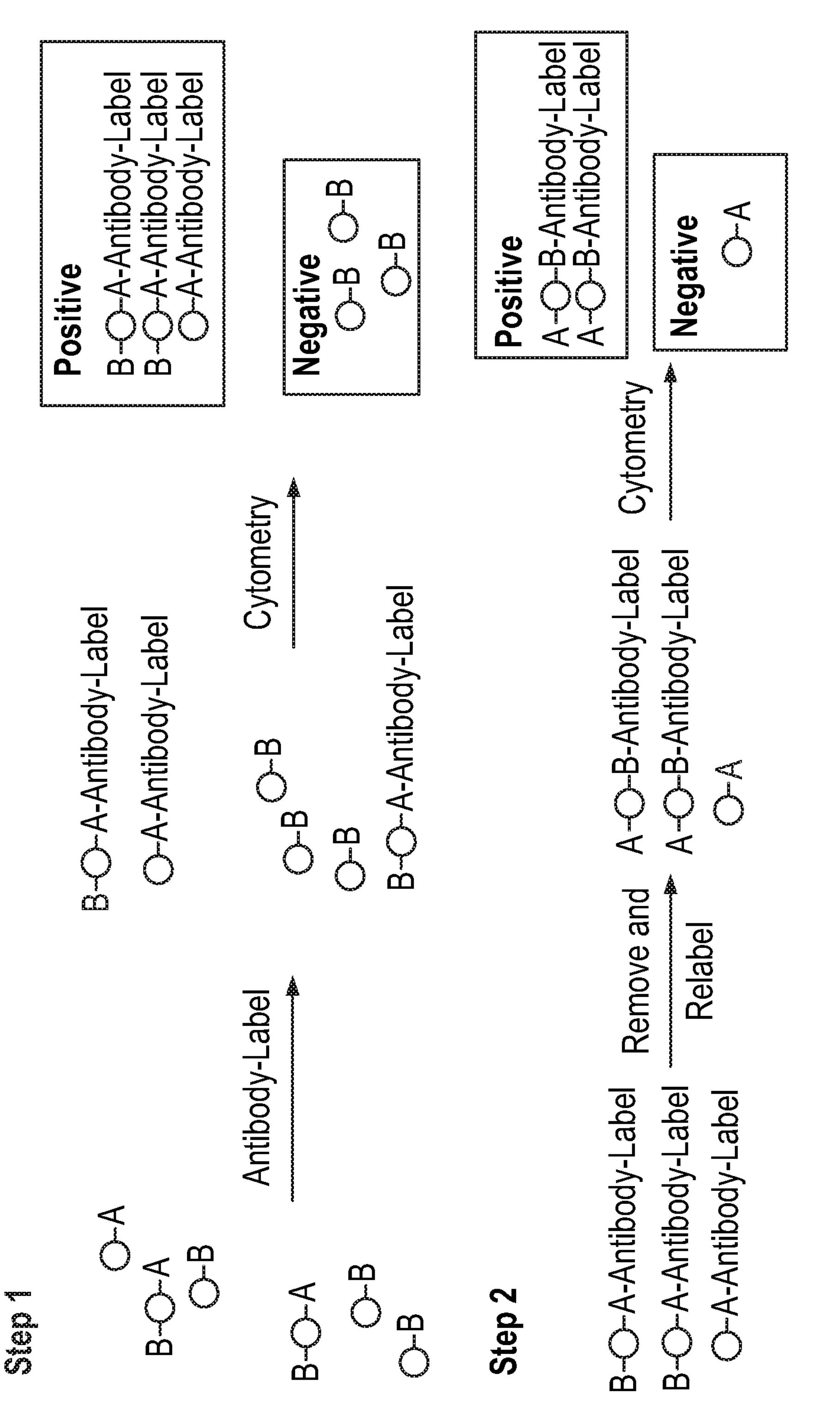
FIG. 8 is a diagram that demonstrates an embodiment on how to separate complex mixtures of cells by iterative flow cytometry. In Step 1, the cells are separated into a labeled (positive) and unlabeled (negative) fraction by contacting a labeled (typically fluorescent) antibody to the mixture that only binds to one of the cell surface proteins in the mixture. Then in Step 2, the antibody-bound cells are removed and a different antibody is used to label a different cell surface protein and thus further separate the sample. This process can be used iteratively and is described in more detail in Example 5.

To derive fixed ratio lymphocytic cell compositions described herein, the cell mixture produced by the methods described in, for example, Example 2, can be, following priming and expansion, separated by flow cytometry. The cells are first labeled with a fluorescent label or quantum dot label by targeting a specific protein expressed on the desired cells which will make up the fixed ratio cell composition with a labeled antibody. The cells are then suspended and entrained in the center of a narrow, rapidly flowing stream of liquid. The flow is engineered in such a way as to allow one cell at a time to pass through the detector which determines if the label is present. This is typically accomplished by using a commercially available cytometry unit. The drops produced by the cell are then separated into a positive and negative fraction based on whether or not the label was detected, where the sample with label is deemed "positive." The antibody is then removed by techniques known in the art. If more than one cell type is pulled from the mixture, for example $CD3^+/CD56^+$ NKT cells and $CD3^+/CD8^+$ T-cells, then another surface protein can be targeted by antibody to allow for an additional round of cytometry. For example, in FIG. 8 the first round of cytometry selects for cell marker A (CD3) and thus removes the unwanted cells. However, the resulting positive fraction still has a mixture of cells. The mixture can now be separated by cell marker B (CD8). In some embodiments the desired cell fraction is the negative fraction.

Following separation of the cells into the desired lymphocytic cell subsets of the fixed cell ratio compositions, the discrete cell populations can be further expanded, if necessary, to reach a sufficient cell population for the fixed ratio cell composition and recombined accordingly into a single product for administration, or administered separately in tandem.

Specific Cell Separations

If desired, a complex mixture of cells that contains the desired cells which comprise the fixed ratio cell compositions described herein, as well as additional cells, can be separated by iterative cytometry. First the $CD3^+$ NKT-cells can be separated from the T-cells by using a label targeting CD56. This positive fraction of $CD3^+$ NKT-cells can be further purified by iteratively targeting CD3. The $CD4^+$ T-cells can then be purified from the negative fraction by targeting CD4. Similarly, the $CD8^+$ T-cells and TCRγδ$^+$ gamma-delta T-cells can be purified from the negative fraction by targeting CD8 and TCRγδ respectively. In some embodiments, the antibodies with different labels are used to create more than two fractions per cytometry step and thus decrease the number of steps necessary. In some embodiments, instead of cytometry the purifications are conducted by chromatography or another technique known in the art. In some embodiments, the cytometer is programmed to produce fractions with the desired ratio of cells.

Initial Characterization of Relative Frequencies of Donor Cellular Subtypes

Alternative methods for arriving at the desired fixed ratios of lymphocytic subsets may also be performed. For example, prior to priming and expanding the various cell types, the relative frequencies of each peripheral blood subset from the donor can be characterized. In an initial step, mononuclear cells are separated from an initial apheresis sample using standard density gradient centrifugation and stained for cell flow cytometry as follows: 1) T-helper cells are stained for the presence of CD3 and CD4; 2) cytotoxic t-cells are stained for the presence of CD3 and CD8; 3) NK-cells are stained for the presence of CD56 and the absence of CD3; 4) γδ T-cells are stained for the present of the γδ receptor and CD3; 5) invariant NK-T cells are stained for the presence of Vα24Jα18; 6) and monocytes are stained for the presence of CD14. In order to maximize the number of cells/events analyzed, the staining is performed in a single tube. Following cell staining, the different cell subtypes are sorted on the basis of sort order, and separated into sequential, separate tubes using fluorescence activated cell sorting (FACS) (with the same antibodies). The cells with the lowest frequencies are sorted first, and the flow-through from each prior sort is used as a starting cellular population for the next sort.

In an alternative embodiment, lymphocytic cell types isolated from fresh or previously frozen human peripheral blood mononuclear cells (PBMCs) or washed leukapheresis samples can be selected using immunomagnetic positive selection. For example, $CD3^+$ cells can be targeted for positive selection with antibodies recognizing the CD3 surface marker. Desired cells are labeled with antibodies and magnetic particles, and separated without columns using a magnet. Unwanted cells are simply poured off, while desired cells remain in the tube. Isolated cells are immediately available for downstream applications such as flow cytometry, culture, or DNA/RNA extraction. The negative population of cells can be used for subsequent positive selection using alternative cell surface markers.

In an alternative embodiment, lymphocytic cell types isolated from fresh or previously frozen human peripheral blood mononuclear cells (PBMCs) or washed leukapheresis samples can be selected using immunomagnetic negative selection. For example, gamma/delta T cells can be isolated from fresh or previously frozen peripheral blood mononuclear cells by negative selection. Non-gamma/delta T cells can be removed with antibodies recognizing specific cell surface markers. Unwanted cells are labeled with antibodies and magnetic particles, and separated without columns using a magnet. Desired cells are poured off into a new tube. Isolated cells are immediately available for downstream applications such as flow cytometry, culture, or DNA/RNA extraction. The remaining cells can be used for subsequent negative selection using alternative cell surface markers.

Expansion of Lymphocytic Cell-Types

Following peripheral blood mononuclear cells isolation using density gradient centrifugation and cell sorting using the methods described above, the various isolated cell subtypes can be expanded as follows:

$CD4^+$ T-Cells

The isolated $CD4^+$ T-cells are primed and expanded as described in or as a modified protocol of, for example Leen et al., "Monoculture-derived T-lymphocytes specific for multiple viruses expand and produce clinically relevant effects in immunocompromised individuals." Nature Medicine, 12(10); 1160-1166 (2006), incorporated herein by reference in its entirety, or a modified protocol thereof.

An additional and separate blood draw is obtained to isolate monocytes for antigen presentation. These monocytes are derived from peripheral blood mononuclear cells of this separate draw following adherence in a culture plate in X-VIVO™ 15 Media (LonzaBio) without cytokines, or alternatively in the presence of GM-CSF and IL-4, at a concentration of $2\times10^6$ cells/2 mL/well of a 24 well plate. The cells are rested for 18 hours, the non-adherent fraction is collected first through collection of the media. The adherent fraction is then harvested by scraping the bottom of the wells. All fractions are then recombined to ensure sufficient cell population, and pulsed with a peptide library of 20 mers overlapping by 15 amino acids spanning the antigen of choice for at least 6 hours at 37° C. The previously sorted $CD4^+$ T-cells are resuspended in 96 well plates in T cell media (44.5% RPMI 44.5% Clicks 10% human serum 1% glutamax) at a concentration of $1\times10^6$ cells/100 μL/well. Cells are then stimulated by adding the pulsed monocytes to T cells at a concentration of $1\times10^5$ cells/100 μL/well. Cells are incubated at 37° C. for 14 hours, and then resuspended on a plate labelled with IFN-γ capture reagent. The reagent is incubated with cells for 15 minutes at 4° C., resuspended in T cell media for 1 hour at 37° C. Cells are then sorted using an IFN-γ capture reagent. The captured cells are then pooled into single wells, and stimulated weekly with 10 ng/mL IL7 and 200 U/mL 1L2, and split into larger or additional wells as the cells expand in number. Cells are expanded for 12 days.

$CD8^+$ T-Cells (αβ T-Cells)

The isolated $CD8^+$ T-cells are primed and expanded as described in or as a modified protocol of, for example Leen et al., "Monoculture-derived T-lymphocytes specific for multiple viruses expand and produce clinically relevant effects in immunocompromised individuals." Nature Medicine, 12(10); 1160-1166 (2006), incorporated herein by reference in its entirety.

An additional and separate blood draw is needed to isolate PHA blasts for antigen presentation. These PHA blasts are derived from peripheral blood mononuclear cells of this separate draw following stimulation with PHA and feed with 100 U/mL IL2 for 5 days. After 7 days, cells are irradiated at 50 Gy, pulsed with a peptide library of 9 mers spanning the antigen of choice for 1-2 hours at 37° C. $CD8^+$ T cells are resuspended in 96 well plates in T cell media (44.5% RPMI44.5% Clicks 10% human serum 1% glutamax) at a concentration of $1\times10^6$ cells/100 μL/well. Cells are then stimulated by adding the irradiated, pulsed PHA blasts to the $CD8^+$ T-cells at a concentration of $1\times10^5$ cells/100 μL/well. Cells are incubated at 37° C. for 14 hours, and then resuspended on a plate labelled with IFN-γ capture reagent. The reagent is incubated with cells for 15 minutes at 4° C., and resuspended in T cell media for 1 hour at 37° C. Cells are then sorted using an IFN-γ capture reagent. These captured cells are then pooled into single wells, and stimulated weekly with 10 ng/mL IL-7, 10 ng/mL IL-15, and split into larger or additional wells as the cells expand in number. Cells are expanded for 12 days.

γδ T-Cells

The isolated γδ T-cells can be activated and expanded as described in or as a modified protocol of, for example, Salot et al., "Large scale expansion of Vγ9Vδ2 T lymphocytes from human peripheral blood mononuclear cells after a positive selection using MACS γ/δ T cell isolation kit." J. Immunol. Methods 347 (2009) 12-18; Kondo et al., "Expansion of human peripheral blood γδ T cells using zoledronate," J Vis Exp. 2011 Sep. 9; (55); Deniger et al., "Activating and Propagating Polyclonal Gamma Delta T Cells with Broad Specificity for Malignancies," Clin Cancer Res Nov. 15 2014 (20)(22) 5708-5719; each incorporated herein by reference in its entirety.

To expand γδ T cells peripheral blood mononuclear cells (PBMC) are isolated from healthy volunteers by density gradient and centrifuged. The supernatant is discarded. Culture medium is prepared by adding human IL-2 (IL-2) and zoledronate (Zometa) to final concentrations of 1000 IU/ml and 5 μM, respectively. ALyS203 (Cell Science & Technology Institute) or OpTmizer (Invitrogen) media support good expansion of γδ T cells. Resuspend the cell pellet in culture medium and adjust to $1\times10^6$ cells/ml. Pipet 1 ml of culture medium containing $1\times10^6$ cells into each well of a 24-well plate. For large-scale cultures, cells can be seeded at $0.5\times10^6$ cells/cm$^2$ according to the surface areas of plate wells, dish, or flask. Add autologous plasma, pooled human AB sera, or FCS so that it is approximately 10% of the volume of the culture (100 μl for each well of a 24-well plate). Place the plates in a humidified 37° C., 5% $CO_2$ incubator for 24-48 hr. Maintain the culture at a cell density of $0.5\text{-}2\times10^6$ cells/ml. Add fresh medium containing human IL-2 (1000 IU/ml) only (without Zometa) every 2-3 days, and transfer cultured cells into new wells or flasks as necessary, according to the degree of cell proliferation. Supply plasma or serum to the medium so that the serum concentration can be maintained at least 1%. Harvest cells on day 12-14 and determine the frequency, phenotype, and functions of γδ T cells by flow cytometry.

To generate activated γδ T-cells, peripheral blood mononuclear cells (PBMC) are isolated from healthy volunteers by density gradient. Thawed PBMCs are initially treated with CD56 microbeads and separated on LS columns to deplete NK cells from cultures. Unlabeled cells from CD56 depletion sorting are then labeled with TCRγ/δ+ T-cell antibody and placed on LS columns to separate γδ T cells in the unlabeled fraction from other cells attached to the magnet. To activate the γδ T cells, they are cocultured at a ratio of one γδ T cell to two γ-irradiated (100 Gy) aAPCs in presence of exogenous IL-2 and IL-21 in complete media. Cells are serially re-stimulated with addition of γ-irradiated aAPCs every 7 days for 2 to 5 weeks in presence of soluble cytokines, 5 which are added three times per week beginning the day of aAPC addition. K562 cells are genetically modified to function as aAPCs. Fluorescence-activated cell sorting (FACS) is used to isolate Vδ1 (TCRδ1+TCRδ2neg), Vδ2 (TCRδ1negTCRδ2+), and Vδ1negVδ2neg (TCRδ1negTCRδ2neg) populations, which are stimulated twice as above with aAPC, phenotyped, and used for functional assays. S T cells from PBMCs are isolated by FACS from thawed mononuclear cells using anti-TCRγδ and anti-CD3 monoclonal antibodies (mAb) and are stimulated for 5 weeks on aAPCs/cytokines as per PBMCs.

CD3$^+$/CD56$^+$ NK T-Cells

The isolated CD3$^+$/CD56$^+$ NK T-cells can be activated and expanded as described in or as a modified protocol of, for example Watarai et al., "Methods for detection, isolation and culture of mouse and human invariant NKT cells." Nature Protocols (2008) Vol. 3 No. 1, pg. 70-78, incorporated herein by reference in its entirety.

Following isolation, the CD3$^+$/CD56$^+$ NK T-cells are plated in a tissue culture dish in RPMI-1640 media containing 10% FBS, HEPES, nonessential amino acids, sodium pyruvate, and 2-mercaptoethanol. CD3$^+$/CD56$^+$ NK T-cells are grown in the presence of 100 ng/mL of alpha-GalCer and 100 U/mL of IL-2. CD3$^+$/CD56$^+$ NK T-cells are re-stimulated on day 6 with alpha GalCer and IL-2. CD3$^+$/CD56$^+$ NK T-cells are split and fed when necessary, and harvested at day 12.

CD3$^-$ NK Cells

The isolated CD3$^-$ NK cells can be expanded as described in or as a modified protocol of, for example, Lapteva et al., "Large-scale ex vivo expansion and characterization of natural killer cells for clinical applications," Cytotherapy. 2012 October; 14(9): 1131-1143, incorporated herein by reference in its entirety.

Peripheral blood mononuclear cells (PBMCs) are isolated from healthy volunteers by density gradient and centrifuged. After calculating the frequency of CD56$^+$ CD3$^-$ NK cells in PBMC, they are seeded into a G-Rex (Wilson-Wolf Manufacturing, New Brighton, MN, USA) at $2\text{-}8\times10^4$ CD56$^+$ CD3$^-$NK cells/cm. K562-mb15-41BBL cells were irradiated with 100 Gy in a Cs-137 irradiator and seeded at a 10:1 ratio of K562-mb15-41BBL to NK cells in Stem Cell Growth Medium (SCGM) and HBSS for Hanks' Balanced Salt Solution (CellGenix USA, Antioch, IL, USA) supplemented with 10% heat-inactivated fetal bovine serum (FBS; Hyclone, ThermoScientific, Logan, Utah, USA) and 10 U/mL IL-2 (Chiron Corporation, Emeryville, CA, USA). Cells are co-cultured for 8-10 days in a G-Rex100 (100-cm gas-permeable surface) or G-Rex10 (10-cm$^2$ surface) in 400 or 40 mL medium, respectively.

Monocytes

Peripheral blood mononuclear cells (PBMCs) are isolated from healthy volunteers by density gradient and centrifuged. Resuspend PBMCs in MACS buffer and add CD14 beads. Incubate at room temperature for 15-20 minutes. 10 mL of MACS buffer is used to wash the cells and then spin cells at 400 g for 5 minutes. Attach the magnet to the stand and attach on LS column to the magnet. Collect the effluent underneath in a tube. Pre-wet the column by running 3 mL MACS buffer. Re-suspend the cells in 3 mL MACS buffer and allow to run through the column. Once the liquid has flowed through the column is rinsed twice with 4.5 mL MACS buffer. Cells are collected in a new 15 mL tube by adding 5 mLs MACS buffer to the column, removing the column from the magnet, and using a plunger to expel cells from the column into the collection tube.

Preparing Cell Composition

Isolated and expanded cell types from above can be cryopreserved for later use. When ready to prepare the fixed ratio cell composition, desired cell types are thawed and the cells are counted. Desired cell types are mixed in fixed ratios in percentages described herein. The fixed ratio cell composition is then provided to the human subject.

This specification has been described with reference to embodiments of the invention. The invention has been described with reference to assorted embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the invention.

What is claimed is:

1. An isolated, non-engineered lymphocytic cell composition for administration to a patient with tumor, wherein the isolated, non-engineered lymphocytic cell composition comprises a predetermined ratio of activated CD4+ T-cells, activated CD8+ T-cells, and activated CD3+ natural killer T (NKT)-cells, wherein the isolated, non-engineered lymphocytic cell composition comprises:

i) from 5% to 25% activated CD4+ T-cells;

ii) from 25% to 55% activated CD8+ T-cells; and iii) from 7.5% to 35% activated CD3+NKT-cells, and wherein the activated CD4+ T-cells and the activated CD8+ T-cells have been primed ex vivo against one or more tumor associated antigens (TAAs), and wherein the one or more tumor associated antigens (TAAs) are selected from the group consisting of Wilms Tumor 1 (WT1), preferentially expressed antigen in melanoma (PRAME), survivin, New York esophageal squamous cell carcinoma (NY-ESO), melanoma-associated antigen (MAGE)-A3, and Synovial sarcoma X chromosome (SSX).

2. The isolated, non-engineered lymphocytic cell composition of claim 1, wherein the predetermined ratio of activated CD4+ T-cells, activated CD8+ T-cells, and activated CD3+ NKT-cells is 1 (±5-10%): 1 (±5-10%): 1 (+/−±5-10%).

3. The isolated, non-engineered lymphocytic cell composition of claim 1, wherein the one or more tumor associated antigens (TAAs) are selected from the group consisting of WT1, PRAME, and survivin.

4. The isolated, non-engineered lymphocytic cell composition of claim 1, wherein at least about 60% of the activated CD4+ T cells are CD4+ T helper 1 cells (Th1-cells).

5. The isolated, non-engineered lymphocytic cell composition of claim 1, wherein less than 5% of cells of the isolated, non-engineered lymphocytic cell composition are positive for one or more cell markers associated with T-cell exhaustion.

* * * * *

SEQUENCE LISTING

<160> NUMBER OF SEQ ID NOS: 3

<210> SEQ ID NO 1
<211> LENGTH: 509
<212> TYPE: PRT
<213> ORGANISM: Homo sapiens

<400> SEQUENCE: 1

```
Met Glu Arg Arg Arg Leu Arg Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

Ser Leu Leu Lys Asp Glu Ala Leu Ala Ile Ala Ala Leu Glu Leu Leu
        35                  40                  45

Pro Arg Glu Leu Phe Pro Pro Leu Phe Met Ala Ala Phe Asp Gly Arg
    50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
        115                 120                 125

His Gln Asp Phe Trp Thr Val Trp Ser Gly Asn Arg Ala Ser Leu Tyr
    130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
            260                 265                 270

Ser Ser Tyr Ile Ser Pro Glu Lys Glu Glu Gln Tyr Ile Ala Gln Phe
        275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
        355                 360                 365
```

```
Leu Gln Ala Leu Leu Glu Arg Ala Ser Ala Thr Leu Gln Asp Leu Val
    370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
        435                 440                 445

Glu Asp Ile His Gly Thr Leu His Leu Glu Arg Leu Ala Tyr Leu His
    450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
            500                 505


<210> SEQ ID NO 2
<211> LENGTH: 117
<212> TYPE: PRT
<213> ORGANISM: HOMO

<400> SEQUENCE: 2

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Trp Val Phe Cys Phe Lys Glu Leu
    50                  55                  60

Glu Gly Trp Glu Pro Asp Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Val Arg Glu Thr Leu Pro Pro Pro
            100                 105                 110

Arg Ser Phe Ile Arg
        115


<210> SEQ ID NO 3
<211> LENGTH: 449
<212> TYPE: PRT
<213> ORGANISM: HOMO

<400> SEQUENCE: 3

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Pro Ala Pro Pro Pro Pro Pro
    50                  55                  60
```

-continued

```
Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu
```